US011718624B2

(12) United States Patent
Liu et al.

(10) Patent No.: US 11,718,624 B2
(45) Date of Patent: Aug. 8, 2023

(54) SOLID STATE FORMS OF SUBSTITUTED PYRAZOLOPYRIMIDINES AND USES THEREOF

(71) Applicant: KSQ Therapeutics, Inc., Lexington, MA (US)

(72) Inventors: Hanlan Liu, Lexington, MA (US); Jeremy Clinton Wilt, Needham, MA (US); Friedrich Blatter, Reinach (CH); Giuseppe Lapadula, Basel (CH)

(73) Assignee: KSQ Therapeutics, Inc., Lexington, MA (US)

( * ) Notice: Subject to any disclaimer, the term of this patent is extended or adjusted under 35 U.S.C. 154(b) by 0 days.

(21) Appl. No.: 17/512,802

(22) Filed: Oct. 28, 2021

(65) Prior Publication Data

US 2022/0162213 A1    May 26, 2022

Related U.S. Application Data

(60) Provisional application No. 63/107,765, filed on Oct. 30, 2020.

(51) Int. Cl.
*C07D 487/04*     (2006.01)
*A61P 35/00*      (2006.01)

(52) U.S. Cl.
CPC ............ *C07D 487/04* (2013.01); *A61P 35/00* (2018.01); *C07B 2200/13* (2013.01)

(58) Field of Classification Search
CPC ............................... C07D 487/04; A61P 35/00
See application file for complete search history.

(56) References Cited

U.S. PATENT DOCUMENTS

| 5,010,175 | A  | 4/1991  | Rutter et al.    |
|-----------|----|---------|------------------|
| 5,475,096 | A  | 12/1995 | Gold et al.      |
| 6,453,242 | B1 | 9/2002  | Eisenberg et al. |
| 7,964,356 | B2 | 6/2011  | Zichi et al.     |
| 8,541,192 | B2 | 9/2013  | D'Andrea         |
| 8,598,184 | B2 | 12/2013 | Zhang            |
| 10,450,281 | B1 | 10/2019 | D'Andrea et al. |
| 2008/0318838 | A1 | 12/2008 | Bauer et al. |
| 2009/0062196 | A1 | 3/2009 | D'Andrea et al. |
| 2010/0190787 | A1 | 7/2010 | Kasibhatla et al. |
| 2011/0144134 | A1 | 6/2011 | Shokat et al. |
| 2012/0202690 | A1 | 8/2012 | Whittingham et al. |
| 2012/0252779 | A1 | 10/2012 | Ramsden et al. |
| 2013/0079512 | A1 | 3/2013 | Nagaraj et al. |
| 2013/0253005 | A1 | 9/2013 | D'Andrea et al. |
| 2017/0145012 | A1 | 5/2017 | Buckmelter et al. |
| 2017/0202810 | A1 | 7/2017 | D'Andrea et al. |
| 2021/0115049 | A1 | 4/2021 | Brenneman et al. |

FOREIGN PATENT DOCUMENTS

| WO | WO-9623899 A1 | 8/1996 |
| WO | WO-9815833 A1 | 4/1998 |
| WO | WO-2014105952 A2 | 7/2014 |
| WO | WO-2015071474 A2 | 5/2015 |
| WO | WO-2017026718 A1 | 2/2017 |
| WO | WO 2020/132269 | * | 6/2020 | ........... A61K 31/519 |
| WO | WO-2020132269 A1 | 6/2020 |
| WO | WO-2021146378 A1 | 7/2021 |
| WO | WO-2021163530 | 8/2021 |
| WO | WO-2022174184 A1 | 8/2022 |

OTHER PUBLICATIONS

U.S. Appl. No. 17/904,159, Wylie, A. A., et al., filed Feb. 12, 2021 (Not Published).
Audeh, M.W., et al., "Oral poly(ADP-ribose) polymerase inhibitor olaparib in patients with BRCA1 or BRCA2 mutations and recurrent ovarian cancer: a proof-of-concept trial," Lancet 376:245-251, Elsevier, Netherlands (2010).
Beerli, R.R., et al., "Engineering polydactyl zinc-finger transcription factors," Nat Biotechnol 20(2): 13 5-141, Nature Publishing Group, United Kingdom (2002).
Berezovski, M.V., et al., "APTAMER-Facilitated Biomarker Discoveiy (AptaBiD)," JACS Articles 130: 9137-9143, American Chemical Society, United States (2008).
Bingham, A. L., et al., "Over one hundred solvates of sulfathiazole," Chemical Communications 7:603-604, Royal Society of Chemistry, United Kingdom (2001).
Bramsen, J.B., et al., "Chemical modification of small interfering RNA," Methods Mol Biol. 721:77-103, SpringerLink, Germany (2011).
Bratkovic, T., et al., "Progress in phage display: evolution of the technique and its applications," Cell Mol Life Sci 67(5):749-767, Springerlink, United States (2010).
Brody, E.N., et al., "High-content affinity-based proteomics: unlocking protein biomarker discovery," Expert Rev Mol. Diagn 10(8):1013-1022, Taylor & Francis, United States (2010).
Cadzow, L., "Development of KSQ-4279 as a First-In-Class USP1 Inhibitor For the Treatment of BRCA-Deficient Cancers," KSQ Therapeutics, poster presented at the 32$^{nd}$ Symposium of the EORTC-NCI-AACR on Molecular Targets and Cancer Therapeutics, Poster #184, 1 page, American Association for Cancer Research, United States (Oct. 2020).
Cadzow, L., "Development of KSQ-4279 as a First-In-Class USP1 Inhibitor for the Treatment of BRCA-Deficient Cancers," European Journal of Cancer 138(S2):S52, Abstract #184, 1 page, Elsevier, Netherlands (Oct. 2020).

(Continued)

*Primary Examiner* — Erich A Leeser
(74) *Attorney, Agent, or Firm* — Sterne, Kessler, Goldstein & Fox P.L.L.C.

(57) ABSTRACT

The present disclosure relates to: a) solid state forms of a compound of Formula (I), a compound of Formula (II), and a compound of Formula (III); b) pharmaceutical compositions comprising one or more solid state forms of a compound of Formula (I), a compound of Formula (II), and a compound of Formula (III), and optionally, a pharmaceutically acceptable carrier or diluent; c) methods of treating tumors or cancers by administering one or more solid state forms of a compound of Formula (I), a compound of Formula (II), and a compound of Formula (III) to a subject in need thereof; and d) methods for the preparation of solid state forms of a compound of Formula (I), a compound of Formula (II), and a compound of Formula (III).

27 Claims, 38 Drawing Sheets

(56) References Cited

OTHER PUBLICATIONS

Caira, M.R., et al., "Preparation and crystal characterization of a polymorph, a monohydrate, and an ethyl acetate solvate of the antifungal fluconazole," Journal of Pharmaceutical Sciences 93(3):601-611, American Pharmacists Association, United States (2003).
Chan, J.H., et al., "Antisense oligonucleotides: from design to therapeutic application," Clin Exp Pharmacol Physiol 33(5-6):533-540, Wiley Online Library, United States (2006).
Chaturvedi, K., et al., "Cyclodextrin-based siRNA delivery nanocarriers: a state-of-the-art review," Expert Opin Drug Delivery 8(11):1455-1468, Taylor and Francis, United States (2011).
Chen, J., et al., "Selective and cell-active inhibitors of the USP1/UAF1 deubiquitinase complex reverse cisplatin resistance in non-small cell lung cancer cells," Chem Biol 18(11):1390-1400, Elsevier, Netherlands (2011).
Chernolovskaya, E.L., et al., "Chemical modification of siRNA," Curr Opin Mol Ther 12(2):158-167, Current Drugs Ltd., United Kingdom (2010).
Choo, Y., et al., "Advances in zinc finger engineering," Curr Opin Struct Biology 10(4):411-416, Elsevier, Netherlands (2000).
Chylinski, K., et al., "The tracrRNA and Cas9 families of type II CRISPR-Cas Immunity systems," RNA Biol 10(5):726-737, Landes Bioscience, United States (2013).
Davis, M.I., et al., "Ubiquitin-Specific Proteases as Druggable Targets," Drug Target Rev 2(3):60-64, Bentham Science, United States (2015).
Deveau, H., et al., "Phage Response to CRISPR-Encoded Resistance in *Streptococcus thermophilus*," Journal of Bacteriology 190(4):1390-1400, American Society for Microbiology, United States (2008).
Dolomanov, O. V., et al., "OLEX2: a complete structure solution, refinement and analysis program," Journal of Applied Crystallography 42(2):339-341, International Union of Crystallography, United Kingdom (Apr. 2009).
Elington, A.D., et al., "In vitro selection of RNA molecules that bind specific ligands," Nature 346:818-822, Nature Publishing Group, United Kingdom (1990).
Esvelt, K.M., et al., "A system for the continuous directed evolution of biomolecules," Nature 472(7344):499-503, Nature Publishing Group, United Kingdom (2011).
Esvelt, K.M., et al., "Orthogonal Cas9 Proteins for RNA-Guided Gene Regulation and editing," Nat Methods 10(11):1116-1121, Nature Publishing Group, United Kingdom (2013).
Farrugia, L. J., "WinGX and ORIEP for Windows: an update," Journal of Applied Crystallography 45(4):849-854, International Union of Crystallography, United Kingdom (Aug. 2012).
Fire, A., et al., "Potent and specific genetic interference by double-stranded RNA in Caenorhabditis elegans," Nature 391(6669):806-811, Nature Publishing Group, United Kingdom (1998).
Foged, C., "siRNA delivery with lipid-based systems: promises and pitfalls," Curr Top Med Chem 12(2):97-107, Betham Science, United States (2012).
Fok, J. H. L., et al., "AZD7648 is a potent and selective DNA-PK inhibitor that enhances radiation, chemotherapy and olaparib activity," Nat Commun 10(1):5065, 15 pages, Nature Publishing Group, United Kingdom (Nov. 2019).
Gaglione, M., et al., "Recent progress in chemically modified siRNAs," Mini Rev Med Chem 10(7):578-595, Bentham Science, United States (2010).
Gallop, M.A., et al., "Applications of combinatorial technologies to drug discovery. 1. Background and peptide combinatorial libraries," J Med Chem 37(9):1233-1251, American Chemical Society, United States (1994).
Gao, Y., et al., "Research Progress on siRNA Delivery with Nonviral Carriers," International Journal of Nanomedicine 6:1017-1025, International Journal of Nanomedicine, Dovepress, United States (2011).
Geary, R.S., "Antisense oligonucleotide pharmacokinetics and metabolism," Expert Opin Drug Metab Toxicol 5(4):381-391, Taylor & Francis, United States (2009).

Gentilucci, L., et al., "Chemical modifications designed to improve peptide stability: incorporation of non-natural amino acids, pseudopeptide bonds, and cyclization," Curr Pharm Des 16(28):3185-3203, Bentham Science, United States (2010).
Horvath et al., "CRISPR/Cas, the immune system of bacteria and archaea," Science, 327(5962): 167-70, American Association for the Advancement of Science (2010).
Huang, T. T., and D'Andrea, A. D., "Regulation of DNA repair by ubiquitylation," Nat Rev Mol Cell Biol 7(5):323-334, Nature Publishing Group, United Kingdom (May 2006).
Isalan et al., "A rapid, generally applicable method to engineer zinc fingers illustrated by targeting the HIV-1 promoter," Nature Biotechnol. 19:656-660, Europe PMC, United Kingdom (2001).
International Search Report and Written Opinion for International Application No. PCT/US2019/067521, International Searching Authority, United States, dated May 5, 2020, 14 pages.
International Search Report and Written Opinion for Application No. PCT/US2021/013369, ISA/US, Commissioner for Patents, Alexandria, Virginia, dated Mar. 31, 2022, 5 pages.
International Search Report and Written Opinion for Application No. PCT/US2021/057072, ISA/US, Commissioner for Patents, Alexandria, Virginia, dated Feb. 18, 2022, 14 pages.
Kanasty et al., "Action and reaction: the biological response to siRNA and its delivery vehicles," Mol. Ther 20: 513-524, Cell Press, United States (2012).
Kim, J. M., et al., "Inactivation of murine Usp1 results in genomic instability and a Fanconi anemia phenotype," Dev Cell 16(2):314-320, Cell Press, United States (Feb. 2009).
Kumari, A., et al., "Nanocarriers: a tool to overcome biological barriers in siRNA delivery," Expert Opinion on Biological Therapy 11(10): 1327-1339, Taylor & Francis, United States (2011).
Kurreck et al., "Design of antisense oligonucleotides stabilized by locked nucleic acids," Nucl Acids Res 30(9): 1911-1918, Oxford Academic, United Kingdom (2002).
Kurreck, J., "Antisense technologies. Improvement through novel chemical modifications," Eur J Biochem 270: 1628-1644, John Wiley & Sons, United States (2003).
Lee, S.K., et al., "Cell-specific siRNA delivery by peptides and antibodies," Methods Enzymol 502: 91-122, Elsevier, Netherlands (2012).
Liang, Q., et al., "A selective USP1-UAF1 inhibitor links deubiquitination to DNA damage responses," Nat Chem Biol 10:298-304, Nature Publishing Group, United Kingdom (2014).
Lim, K.S., et al., "Abstract 333: USP1 is required for replication fork stability in BRCA1-deficient tumors," AACR 78(13): 1 page, Proceedings of the American Association for Cancer Research Annual Meeting, Apr. 14-Apr. 18, United States (2018).
Lim, K. S., et al., "USP1 Is Required for Replication Fork Protection in BRCA1-Deficient Tumors," Mol Cell 72(6):925-941, Cell Press, United States (Dec. 2018).
Lord, C. J., and Ashworth, A., "PARP inhibitors: Synthetic lethality in the clinic," Science 355(6330):1152-1158, American Association for the Advancement of Science, United States (Mar. 2017).
Macrae, C. F., et al., "Mercury: visualization and analysis of crystal structures," Journal of Applied Crystallography 39(3):453-457, International Union of Crystallography, United Kingdom (Jun. 2006).
Mali, P., et al., "RNA-guided human genome engineering via Cas9," Science 339(6121): 823-24, American Association for the Advancement of Science, United States (2013).
McManus, M., et al., "Gene silencing in mammals by small interfering RNAs," Nat Rev Genet 3:737-747, Nature Publishing Group, United Kingdom (2002).
Miller, J., et al., "Repetitive zinc-binding domains in the protein transcription factor IIIA from Xenopus oocytes," EMBO J 4(6): 1609-1614, EMBO Press, United States (1985).
Mistry, H., et al., "Small-Molecule Inhibitors of USP1 Target ID1 Degradation in Leukemic Cells," Mol. Cancer Ther 12:2651-2662, American Association for Cancer Research, United States (2013).
Murai, J., et al., "The USP1/UAF1 complex promotes double-strand break repair through homologous recombination," Mol Cell Biol 31(12):2462-2469, American Society for Microbiology, United States (published online Apr. 2011, published in print Jun. 2011).

(56) References Cited

OTHER PUBLICATIONS

Naeye, B., et al., "Matrix systems for siRNA delivery," Curr Top Med Chem 12: 89-96, Bentham Publishers, Netherlands (2012).
Ni, X et al., "Nucleic acid aptamers: clinical applications and promising new horizons," Cun-Med Chem 18(27): 4206, Bentham Publishers, Netherlands (2011).
Pabo, C., et al., "Design and selection of novel Cys2His2 zinc finger proteins," Ann Rev Biochem 70:313-340, Annual Reviews, United States (2001).
Pande, J., et al., "Phage display: concept, innovations, applications and future," Biotech Adv 28: 849-858, Elsevier, Netherlands (2010).
Parmar, K., et al., "Hematopoietic stem cell defects in mice with deficiency of Fancd2 or Usp1," Stem Cells 28(7):1186-1195, Wiley-Blackwell, United States (Jul. 2010).
Pasternak, A., et al., "Unlocked nucleic acid—an RNA modification with broad potential," Organic & Biomolecular Chemistry (9): 3591-3597, Royal Society of Chemistry, United Kingdom (2011).
Peacock, H. et al., "Chemical Modification of siRNA Bases to Probe and Enhance RNA Interference," J Org Chem 76: 7295-7300, ACS Publications, United States (2011).
Prakash, T.P., "An overview of sugar-modified oligonucleotides for antisense therapeutics," Chemistry & Biodiversity 8(9):1616-1641, Europe PMC, United States (2011).
Pubchem, "SID 38205792," pubchem.ncbi.nlm.nih.gov, Deposit Date: Dec. 5, 2007, accessed at URL:[https://pubchem.ncbi.nlm.nih.gov/substance/38205792] on Mar. 19, 2021, 5 pages.
PubchemCID 129736955,9-Benzyl-2-(2-fluorophenyl)purine, Sep. 13, 2017, accessed at https://pubchem.ncbi.nlm.nih.gov/compound/129736955, accessed on Feb. 12, 2020.
Rageul, J., and Kim, H., "Fanconi anemia and the underlying causes of genomic instability," Environ Mol Mutagen 61(7):693-708, Wiley-Liss Inc., United States (published online Feb. 2020, published in print Aug. 2020).
Rhodes, D., et al., "Zinc Fingers," Scientific American 268(2):56-59,62-65, Scientific American, United States (1993).
Roon-Mom, W.M., et al., "Overview on applications of antisense-mediated exon skipping," Methods Mol Biol 867:79-96, Springerlink, United States (2012).
Sa, J. K., et al., "Pharmacogenomic analysis of patient-derived tumor cells in gynecologic cancers," Genome Biology: 13 pages, Biomed Central, United States (2019).
Segal, D.J., et al., "Custom DNA-binding proteins come of age: polydactyl zinc-finger proteins," Curr Opin Biotechnol 12(6):632-637, Elsevier, Netherlands (2001).
Seth, S., et al., "Delivery and biodistribution of siRNA for cancer therapy: challenges and future prospects," Therapeutic Delivery 3(2):245-261, Future Science, United States (2012).
Sharei, A., et al., "A vector-free microfluidic platform for intracellular delivery," PNAS, 110(6), 2082-2087, National Academy of Sciences, United States (2013).
Shegokar, R., et al., "SiRNA Delivery: challenges and role of carrier systems," Pharmazie 66(5):313-318, Govi-Verlag Pharmazautischer Verlag, Germany (2011).
Sheldrick, G. M., "Crystal structure refinement with SHELXL," Acta Crystallogr C Struct Chem 71(Pt 1):3-8, International Union of Crystallography, United Kingdom (Jan. 2015).
Sizemore, S. T., et al., "Synthetic Lethality of PARP Inhibition and Ionizing Radiation is p53-dependent," Mol Cancer Res 16(7): 1092-1102, American Association for Cancer Research, United States (published online Mar. 2018, published in print Jul. 2018).
Sullivan, P., "USP1 inhibitors show robust combination activity and a distinct resistance profile from PARP inhibitors," European Journal of Cancer 138(S2):S7-S8, Abstract #ORAL003, 2 pages, Elsevier, Netherlands (Oct. 2020).
Jacquemont, C., and Taniguchi, T., "The Fanconi anemia pathway and ubiquitin," BMC Biochemistry 8(1):S10, 10 pages, Biomed Central, United States (2007).
Thompson, L.A., et al., "Synthesis and Applications of Small Molecule Libraries," Chemical Review 96:555-600, American Chemical Society, United States (1996).
Tuerk, C., et al., "Systematic evolution of ligands by exponential enrichment: RNA ligands to bacteriophage T4 DNA polymerase," Science 249(4968):505-510, AAAS, United States (1990).
The United States Pharmacopeia—National Formulary, "941 X-ray Diffraction," 23rd Edition, NF-18, pp. 1843-1844,The United States Pharmacopeial Convention, United States (1995).
Vader, P., et al., "Polymeric Carrier Systems for siRNA Delivery," Current Topics in Medicinal Chemistry 12(2):108-119, Bentham Science, United States (2012).
Van Tonder, E.C., et al., "Preparation and physicochemical characterization of 5 niclosamide solvates and 1 hemisolvate," AAPS PharmSciTech 5(1), Art. 12, 1-10, Springerlink, Germany (2004).
Varasteh, M., et al., "Quantitative determination of polymorphic impurity by X-ray powder diffractometry in an OROS formulation," Int J Pharm 366(1-2):74-81, Elsevier, Netherlands (published online Sep. 2008, published in print Jan. 2009).
Wang, C., et al., "ATM-Deficient Colorectal Cancer Cells are Sensitive to the PARP Inhibitor Olaparib," Trani Oncol, 10(2):190-196, Elsevier, Netherlands (2017).
Wylie, A., "USP1 inhibitors show robust combination activity and a distinct resistance profile from PARP inhibitors," KSQ Therapeutics, presented at the 32$^{nd}$ Symposium of the EORTC-NCI-AACR on Molecular Targets and Cancer Therapeutics, Virtual Conference, ORAL003, 17 pages, American Association for Cancer Research, United States (Oct. 24, 2020).
Yamamoto, T., et al., "Antisense drug discovery and development," Future Medicinal chemistry 3(3):339-365, Future Science, United States (2011).
Zhang, Y,. et al., "Comparison of non-canonical PAMs for CRISPR/Cas9-mediated DNA cleavage in human cells," Sci Rep 5405:1-5, Scientific Reports, United States (2014).

\* cited by examiner

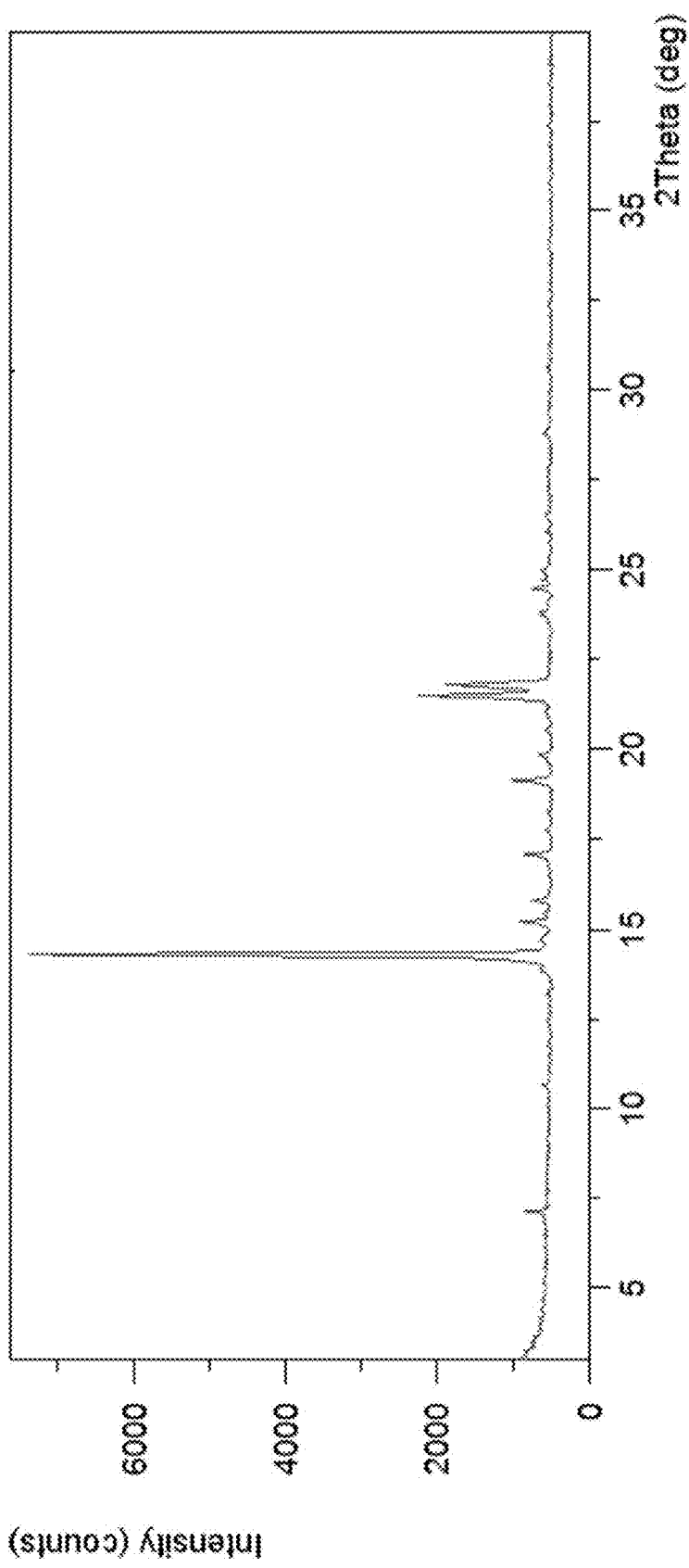
FIGURE 1: Powder X-ray diffraction pattern ("XRPD") corresponding to crystalline Form A

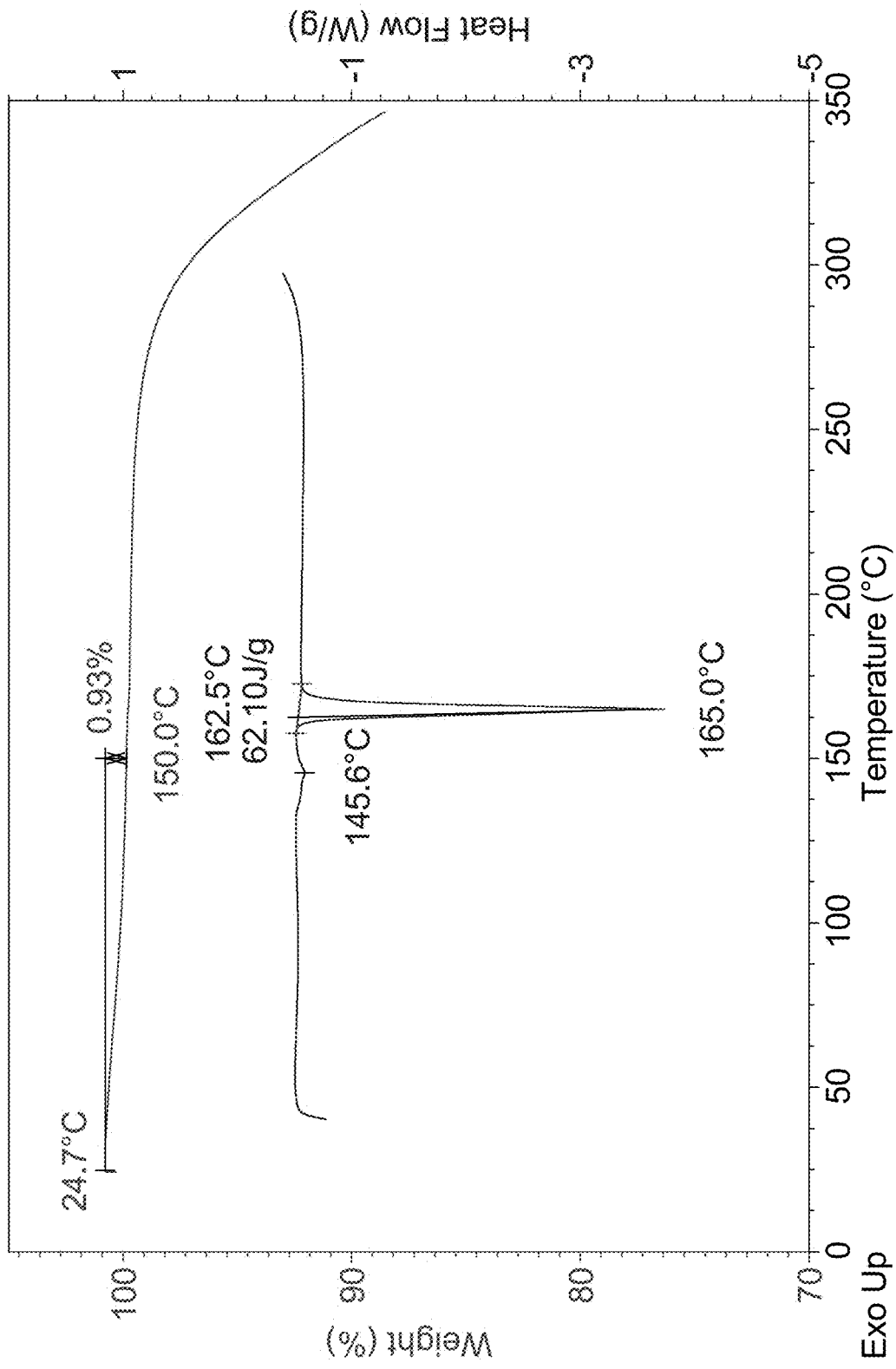
FIGURE 2: DSC and TGA thermograms corresponding to crystalline Form A

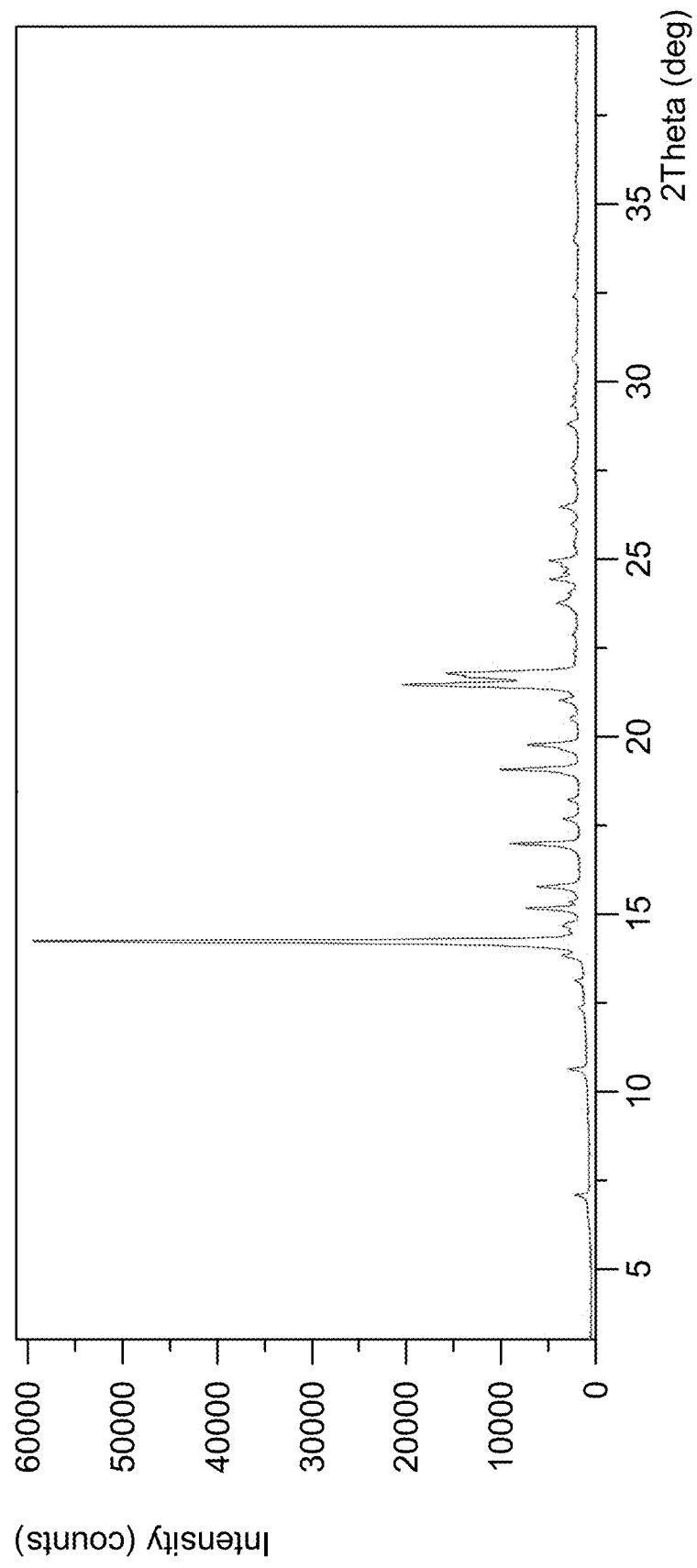
FIGURE 3: XRPD pattern corresponding to crystalline Form C

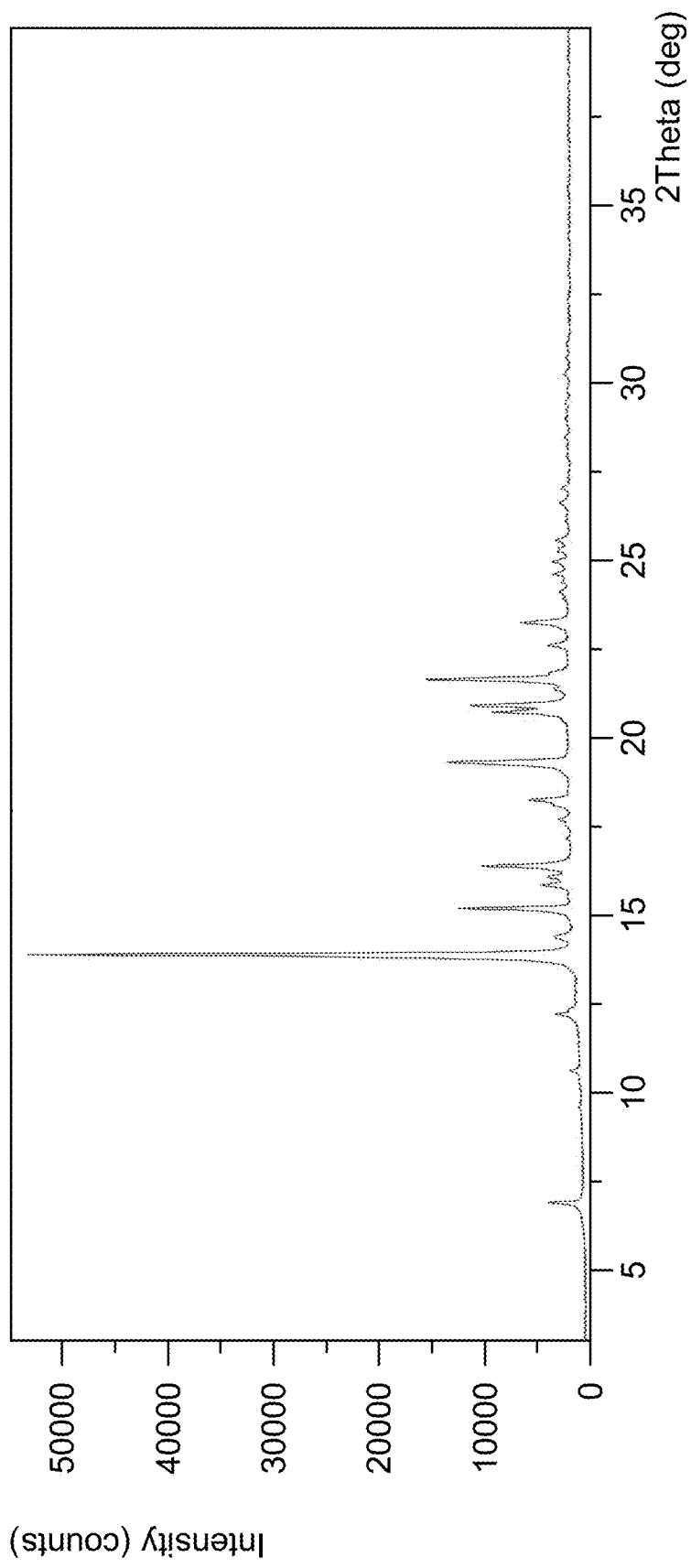
FIGURE 4: XRPD pattern corresponding to crystalline Form D

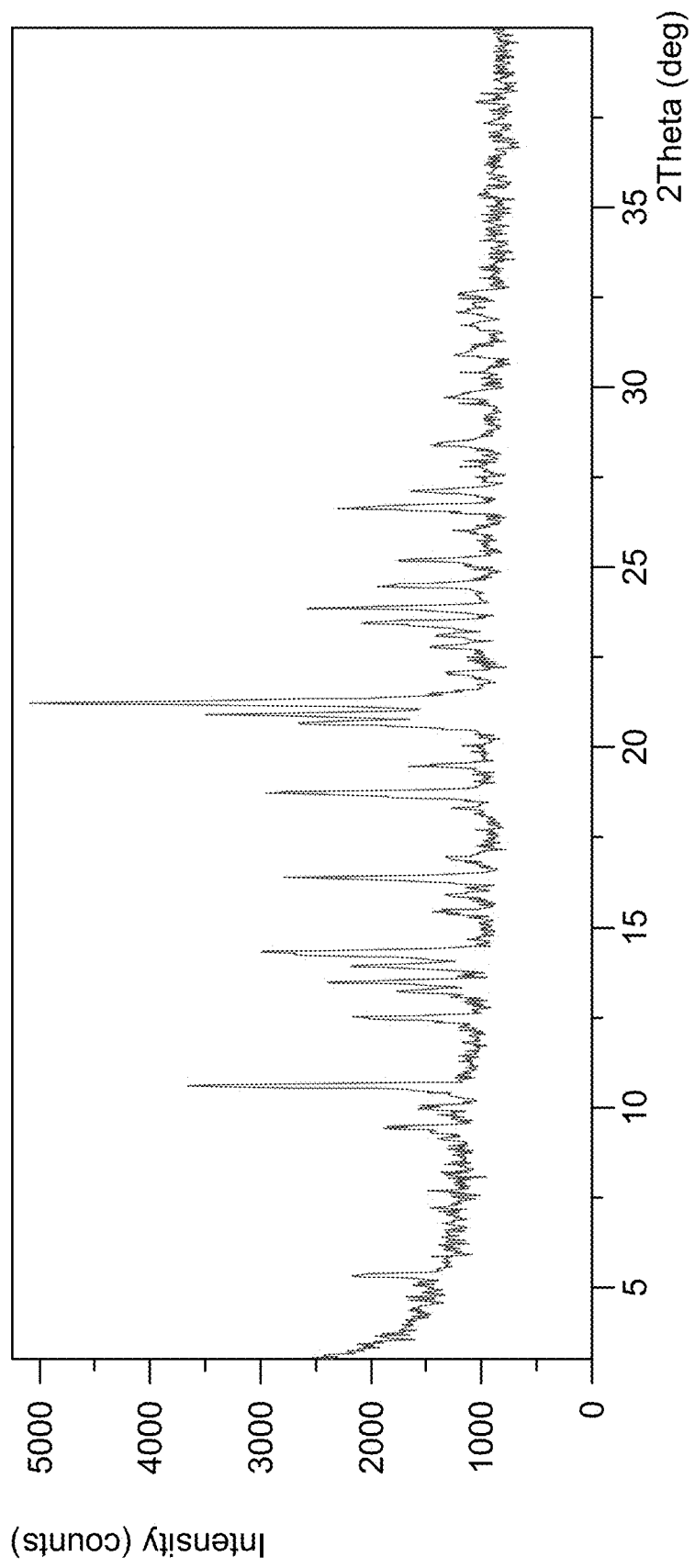
FIGURE 5: XRPD pattern corresponding to crystalline Form E

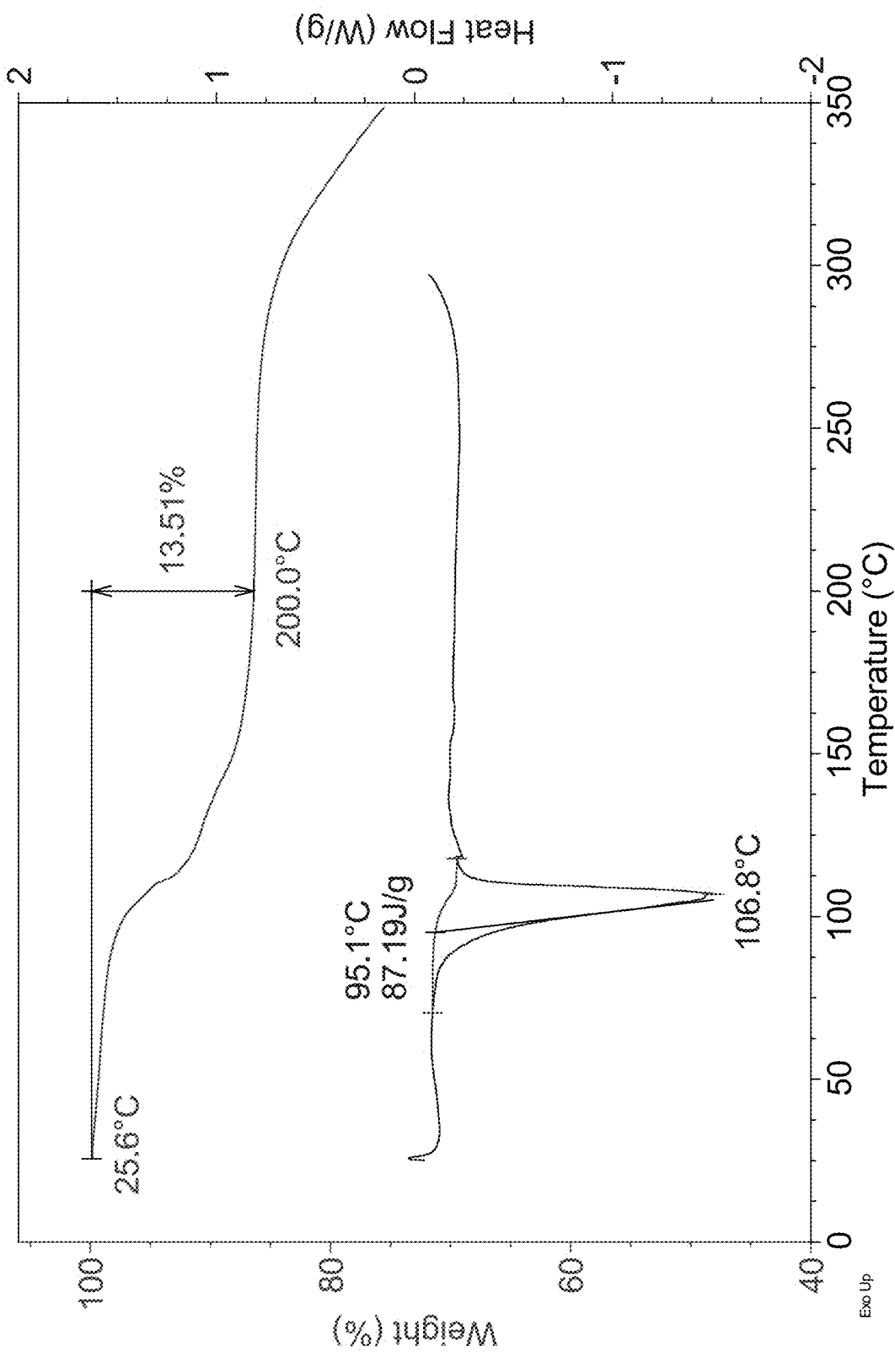
FIGURE 6: DSC and TGA thermogram corresponding to crystalline Form E

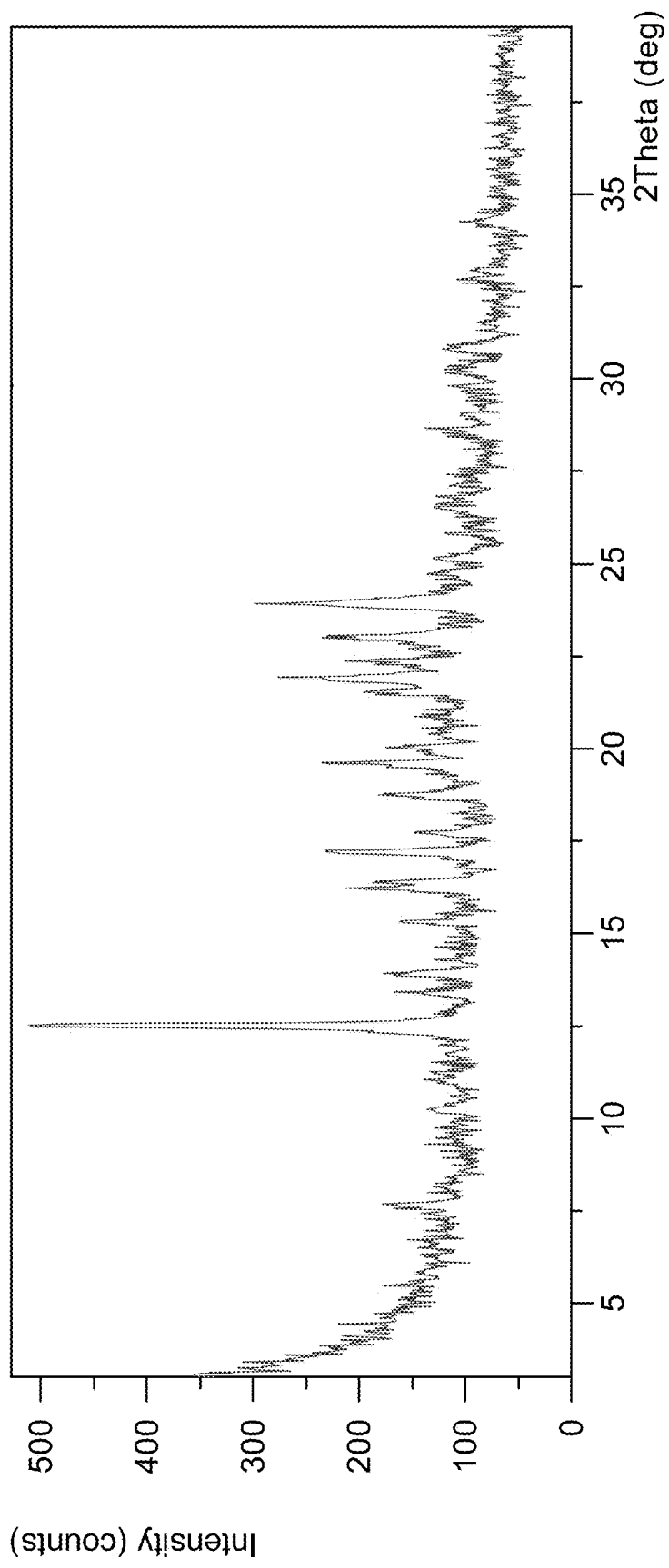
FIGURE 7: XRPD pattern corresponding to crystalline Form 1

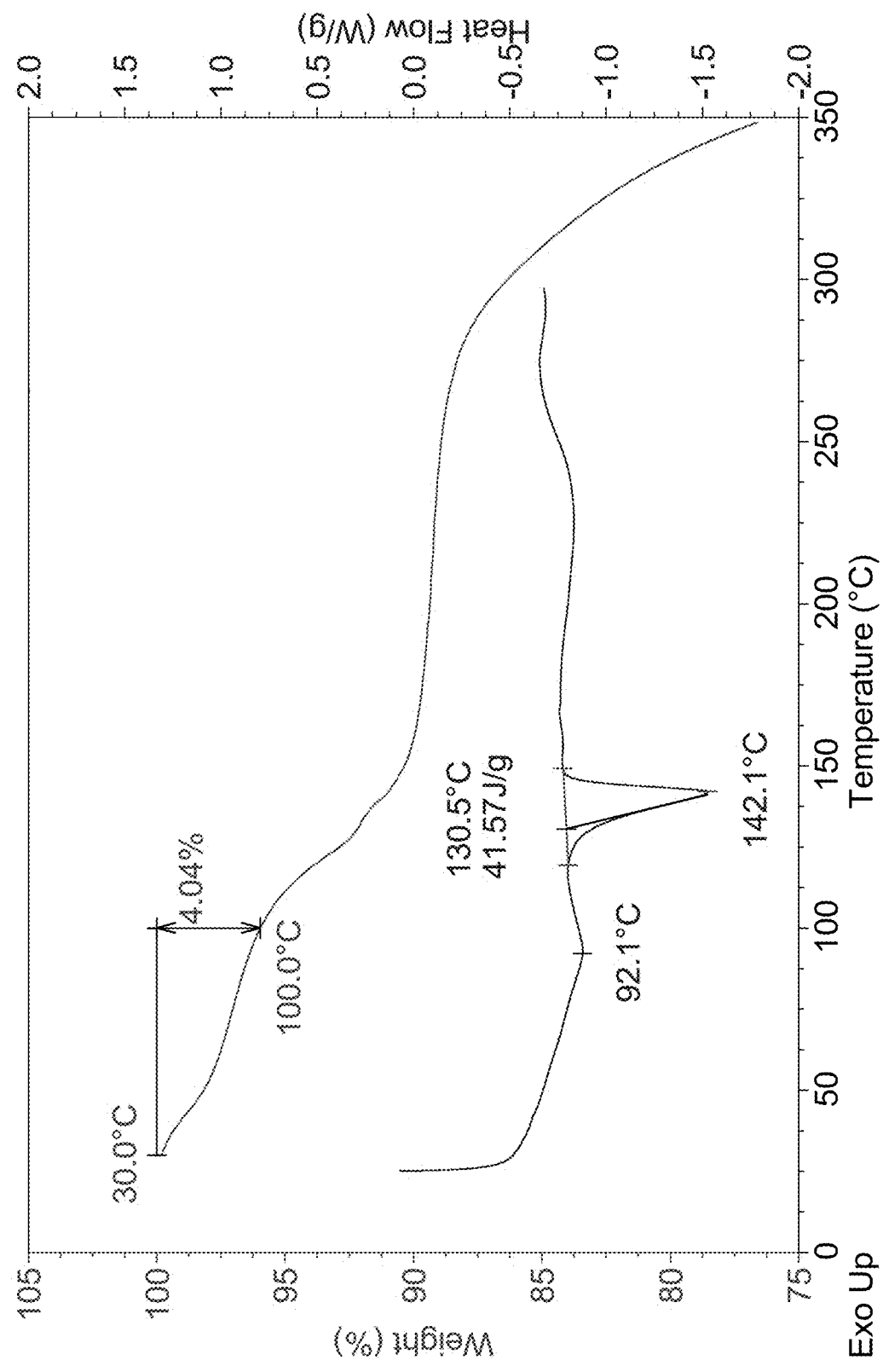
FIGURE 8: DSC and TGA thermogram corresponding to crystalline Form 1

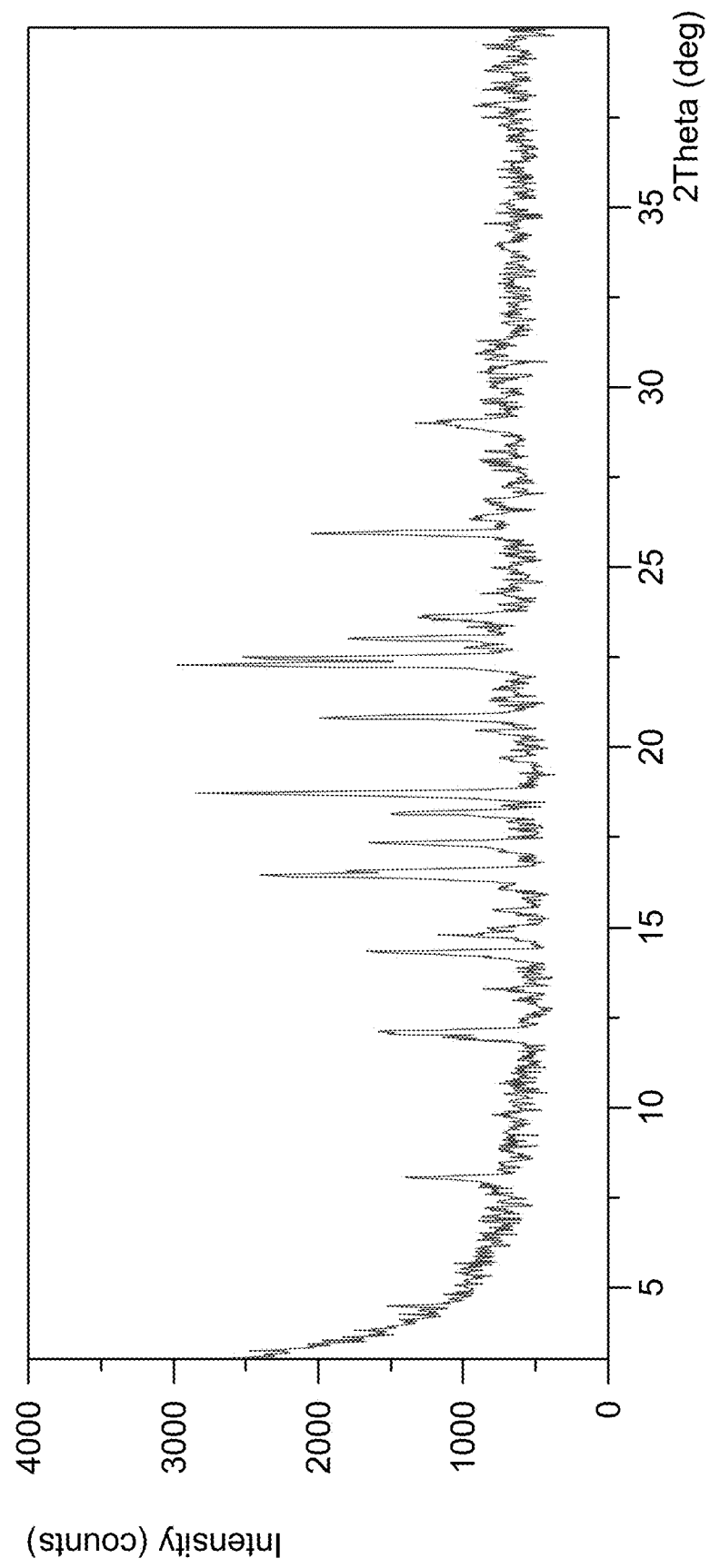
FIGURE 9: XRPD pattern corresponding to crystalline Form 2

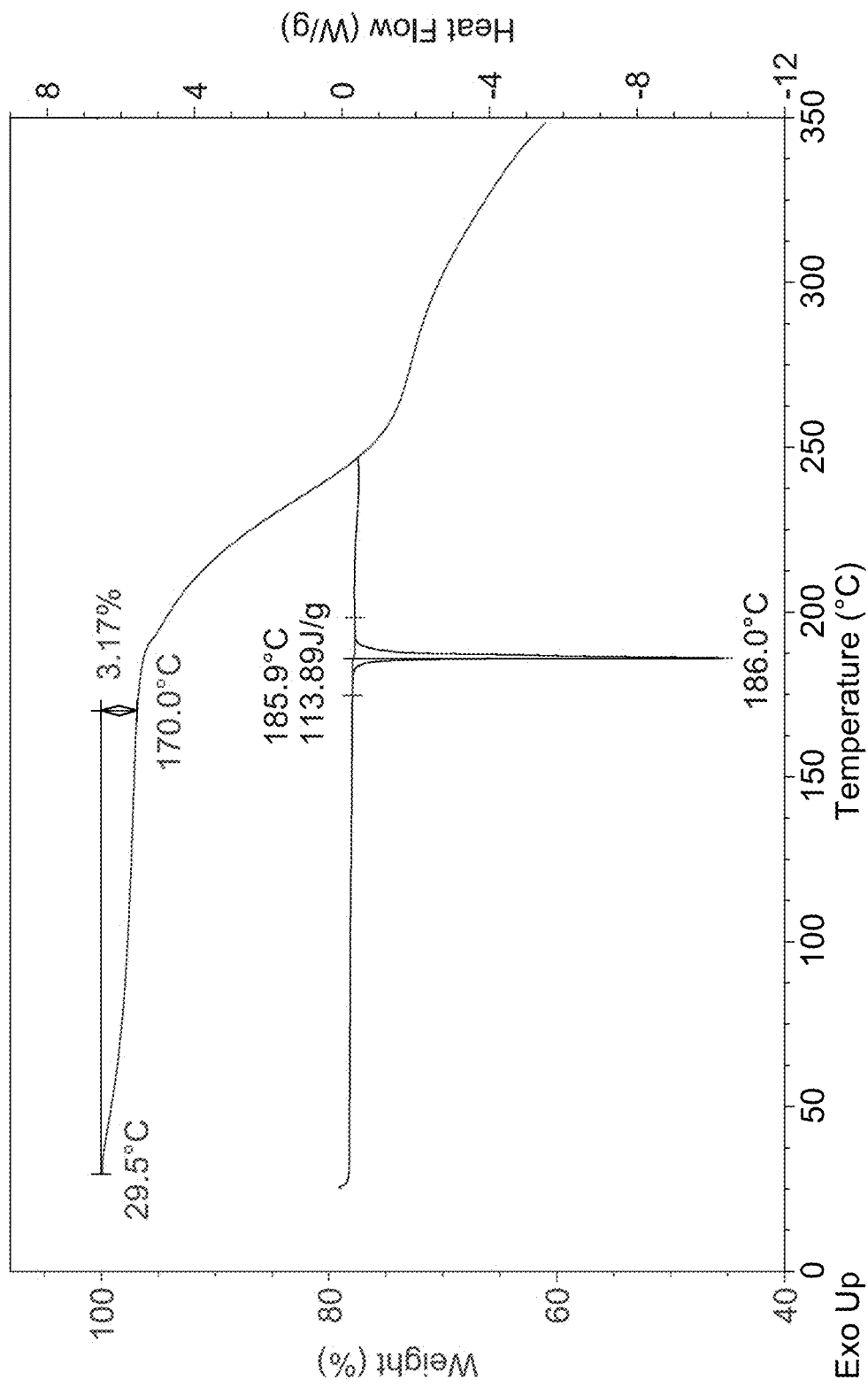
FIGURE 10: DSC and TGA thermogram corresponding to crystalline Form 2

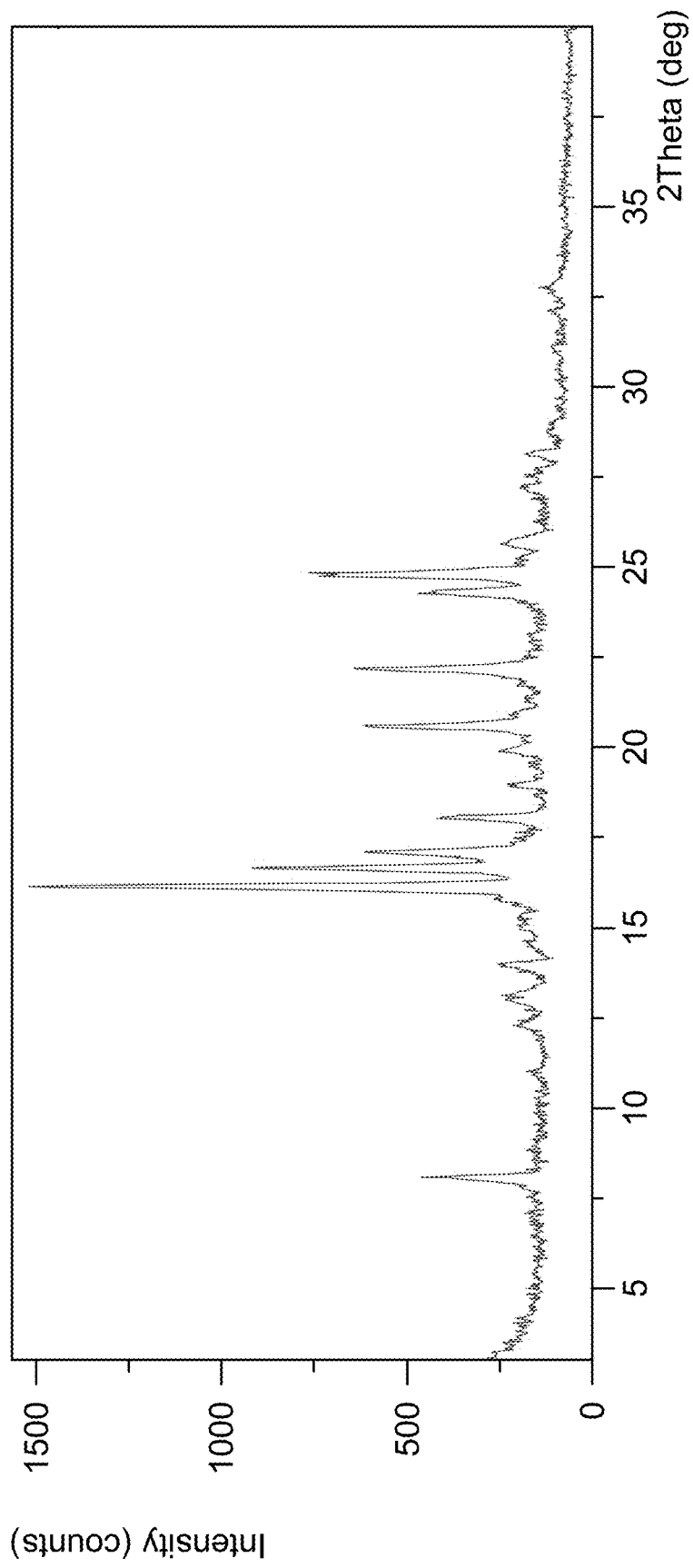
FIGURE 11: XRPD pattern corresponding to crystalline Form A1

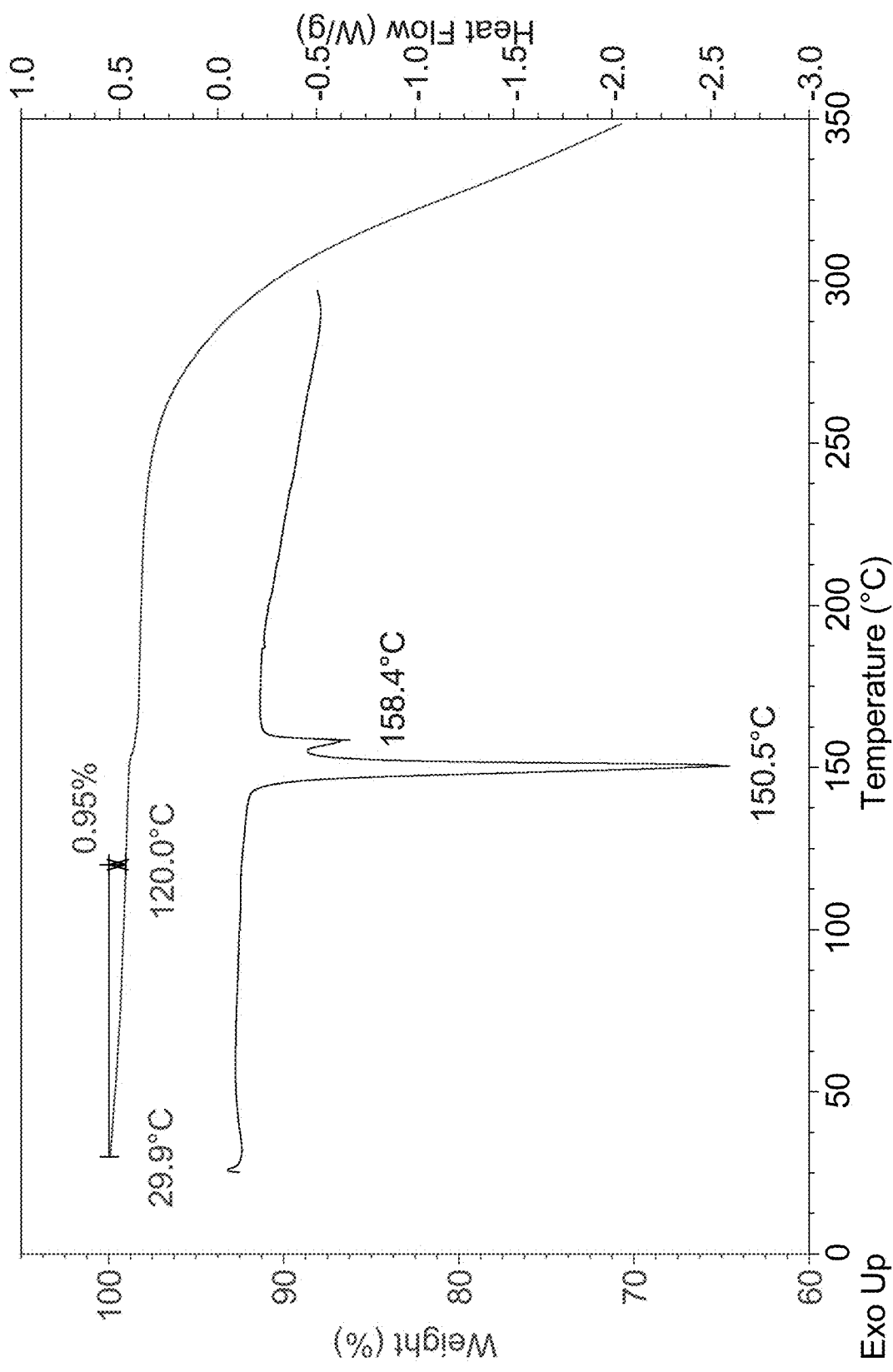
FIGURE 12: DSC and TGA thermogram corresponding to crystalline Form A1

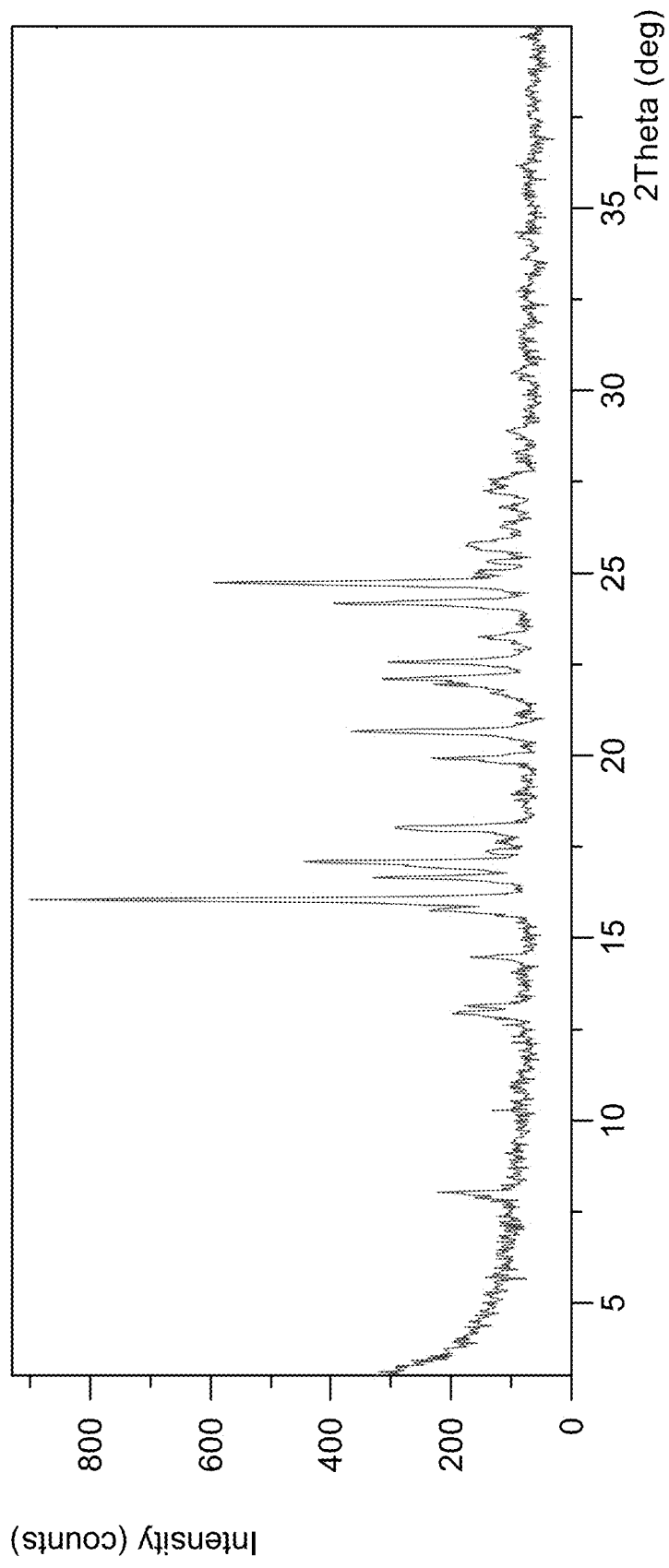
FIGURE 13: XRPD pattern corresponding to crystalline Form B1

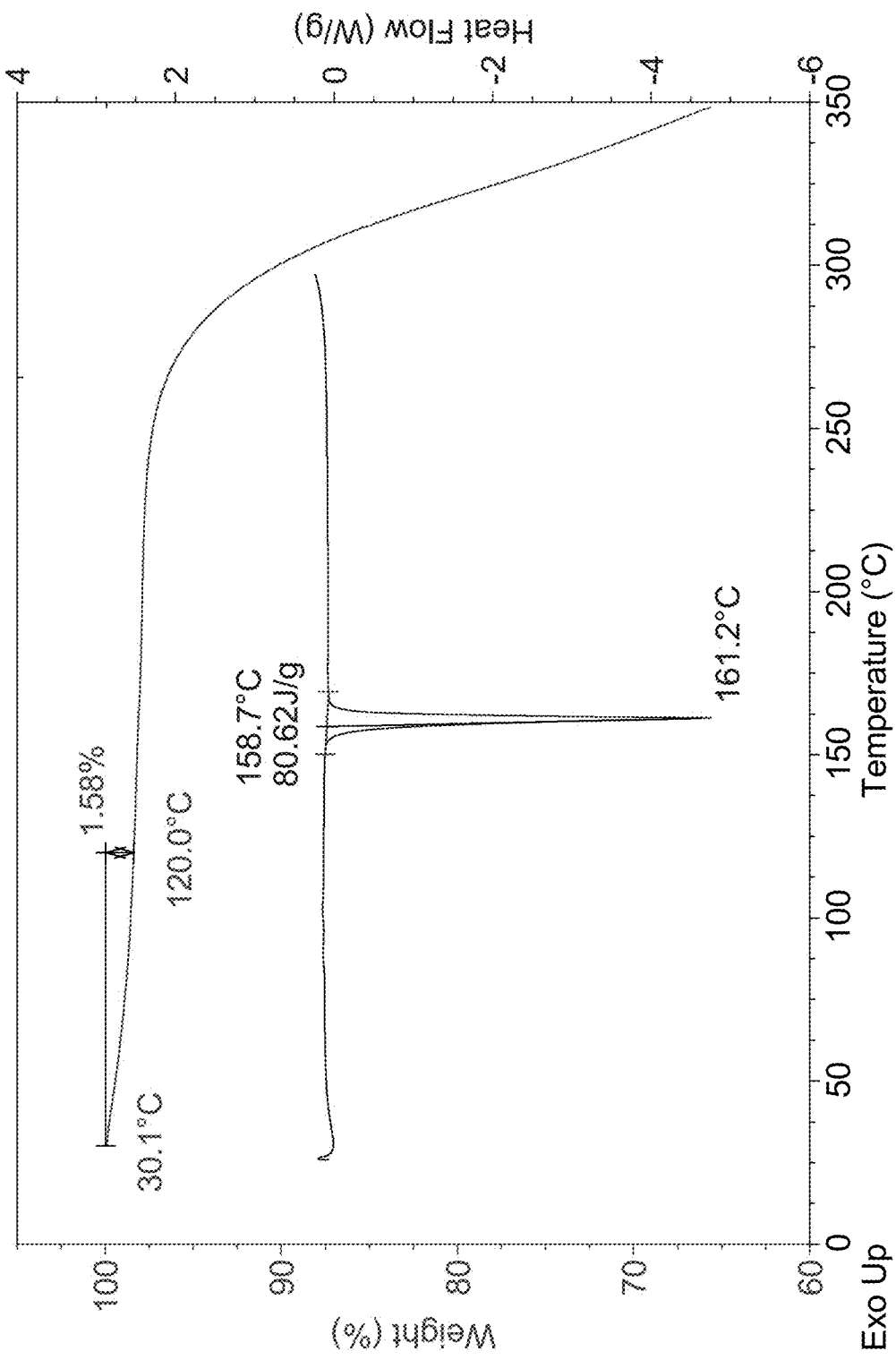
FIGURE 14: DSC and TGA thermogram corresponding to crystalline Form B1

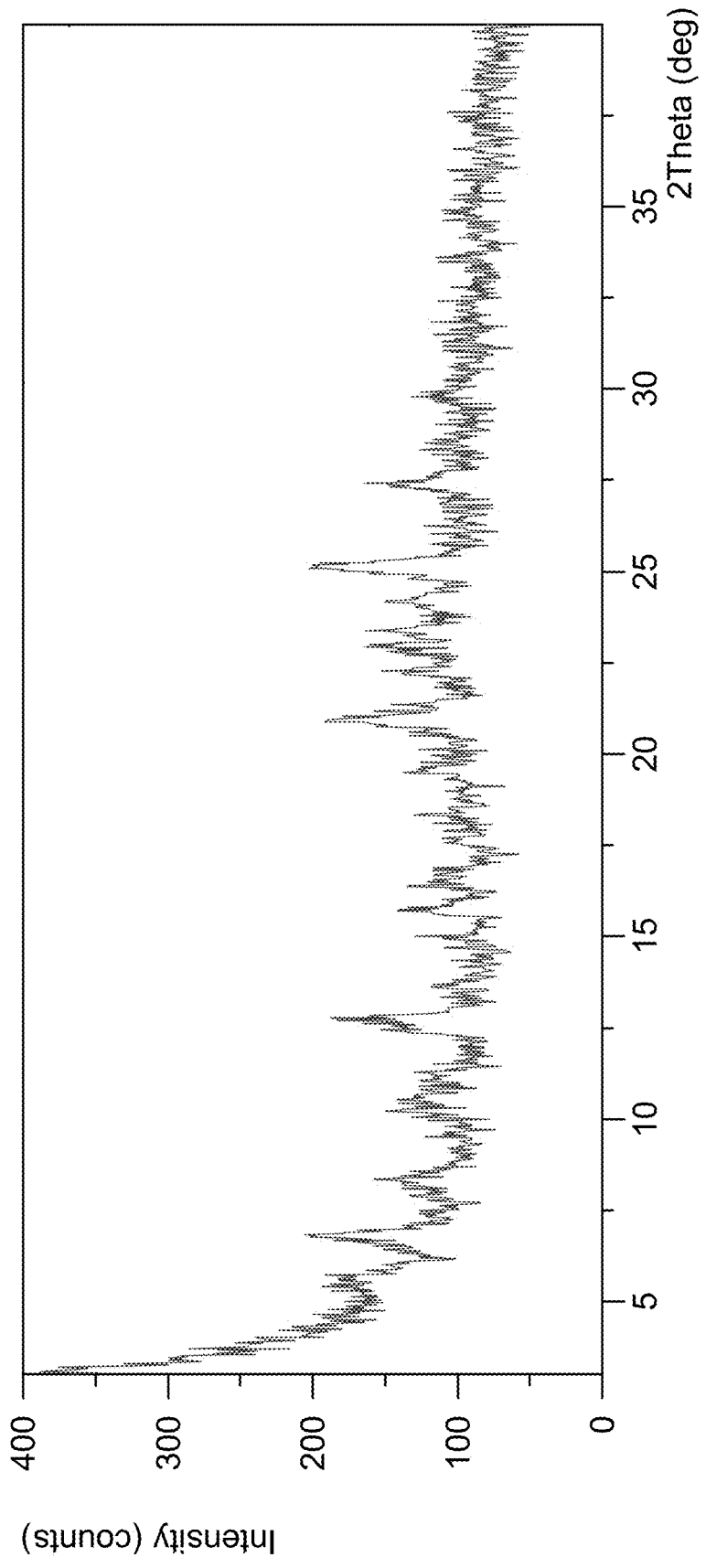
FIGURE 15: XRPD pattern corresponding to crystalline Form 3

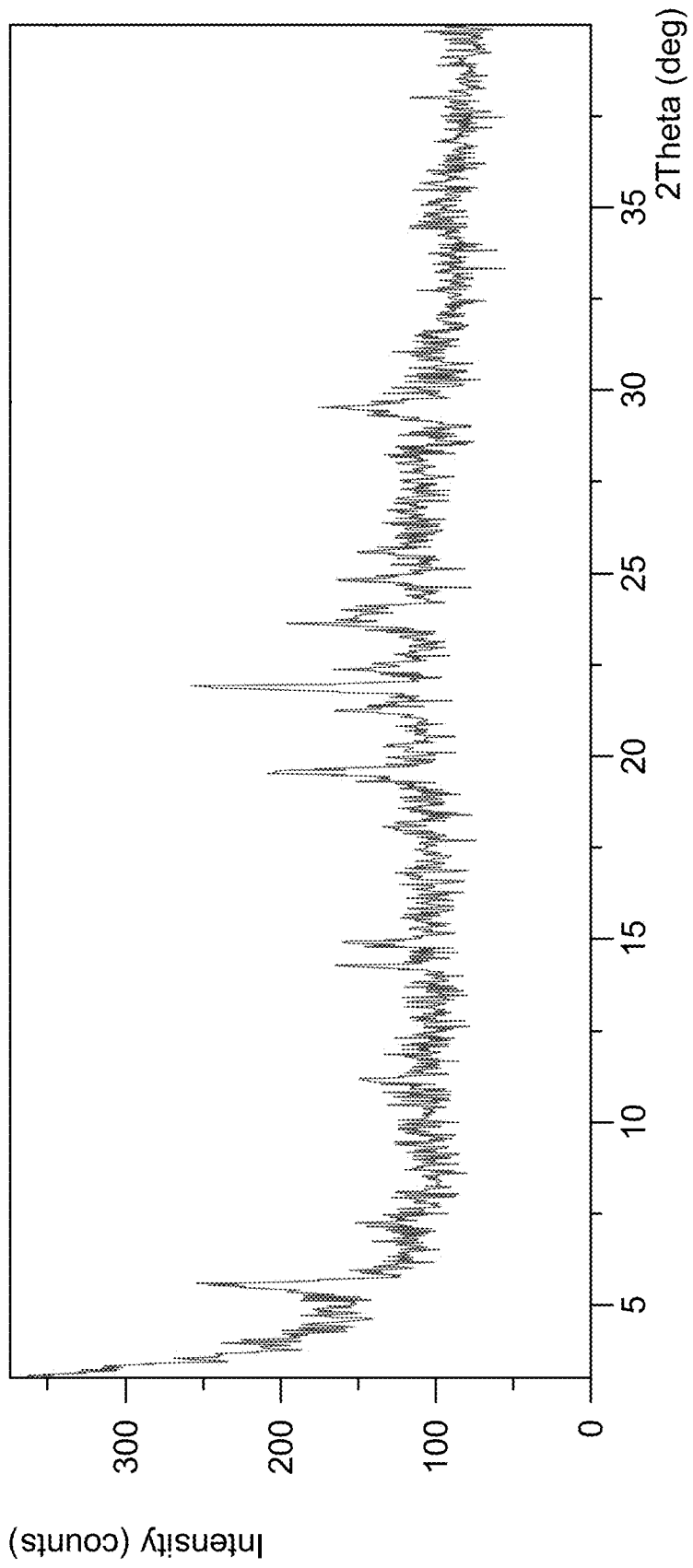
FIGURE 16: XRPD pattern corresponding to crystalline Form 4

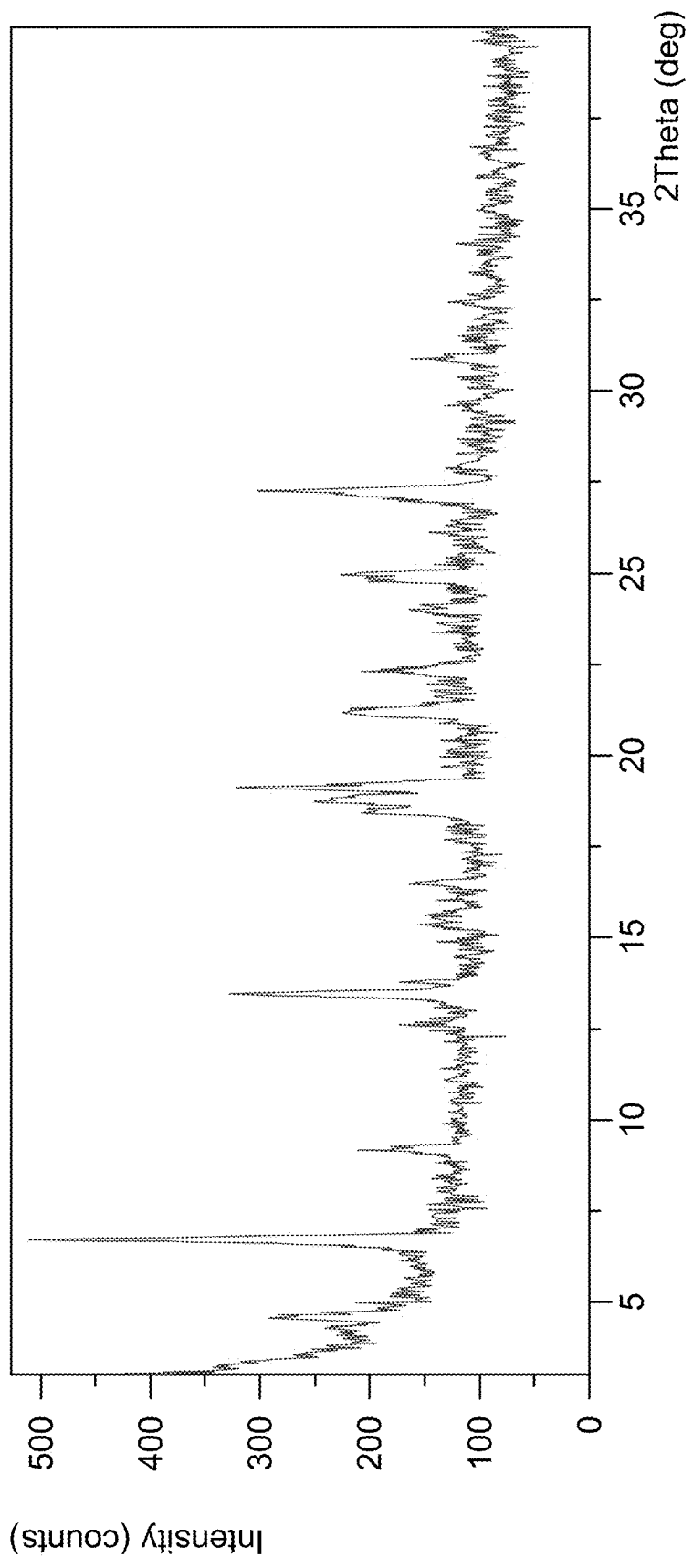
FIGURE 17: XRPD pattern corresponding to crystalline Form 5

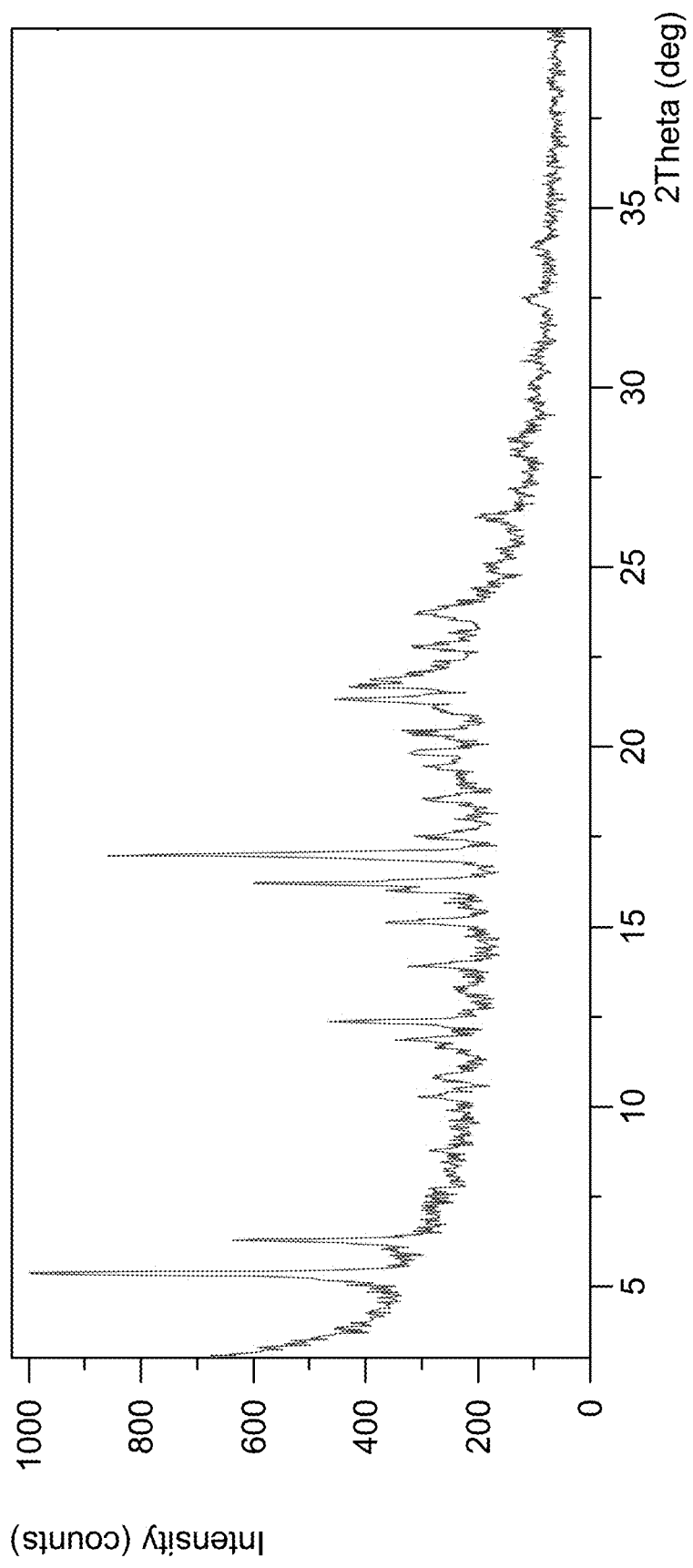
FIGURE 18: XRPD pattern corresponding to crystalline Form 6

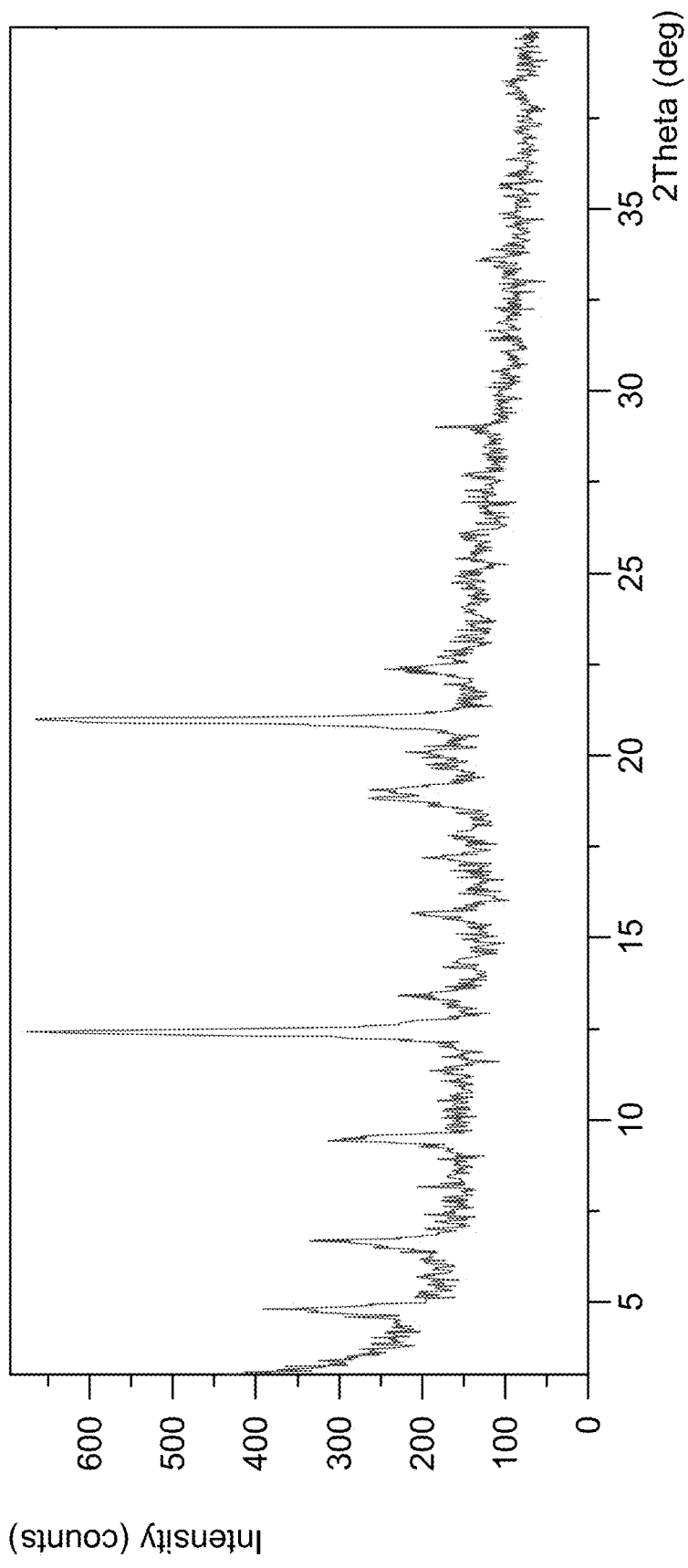
FIGURE 19: XRPD pattern corresponding to crystalline Form 7

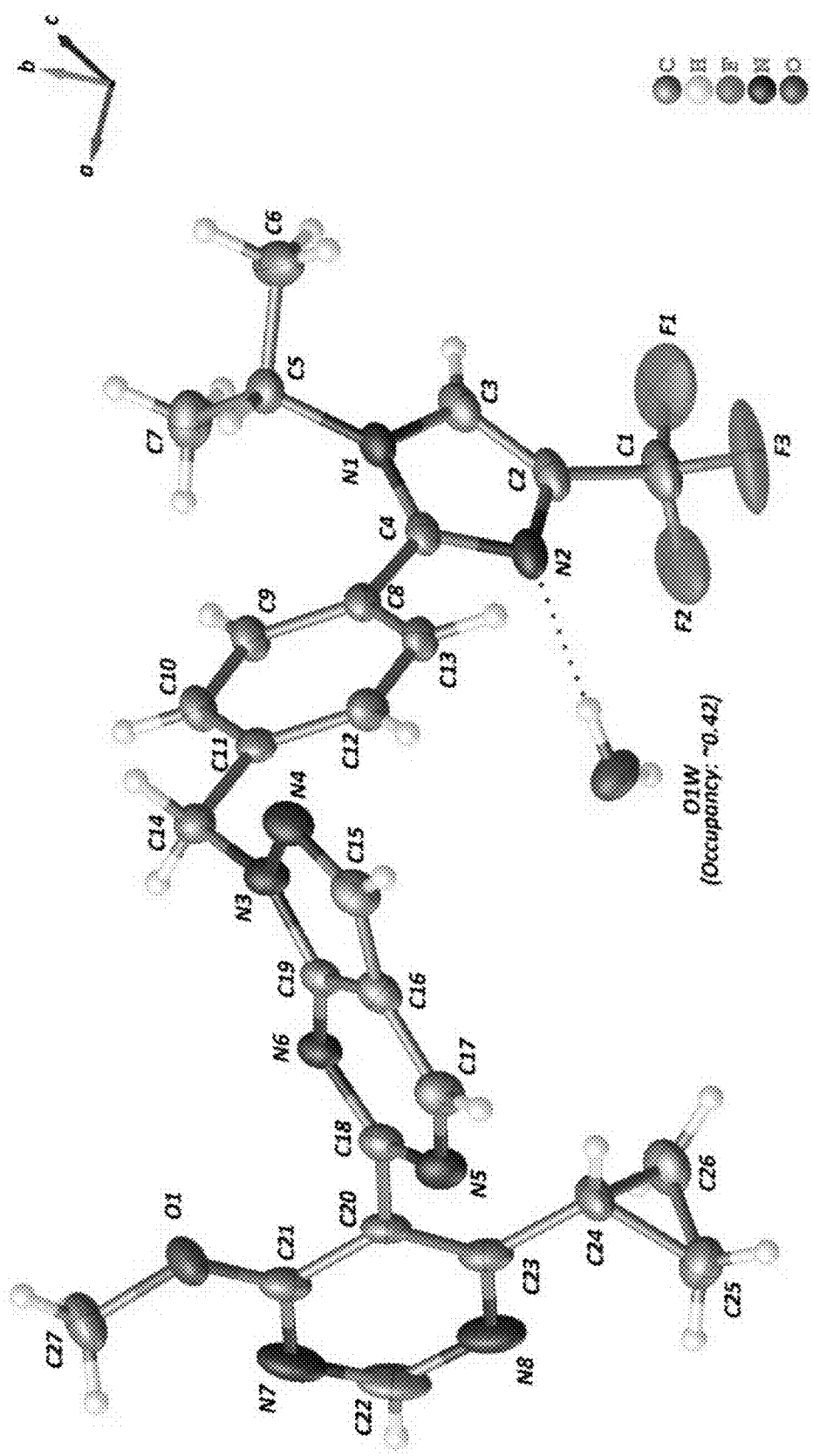
FIGURE 20: Asymmetric unit of crystalline Form A from a single crystal structure

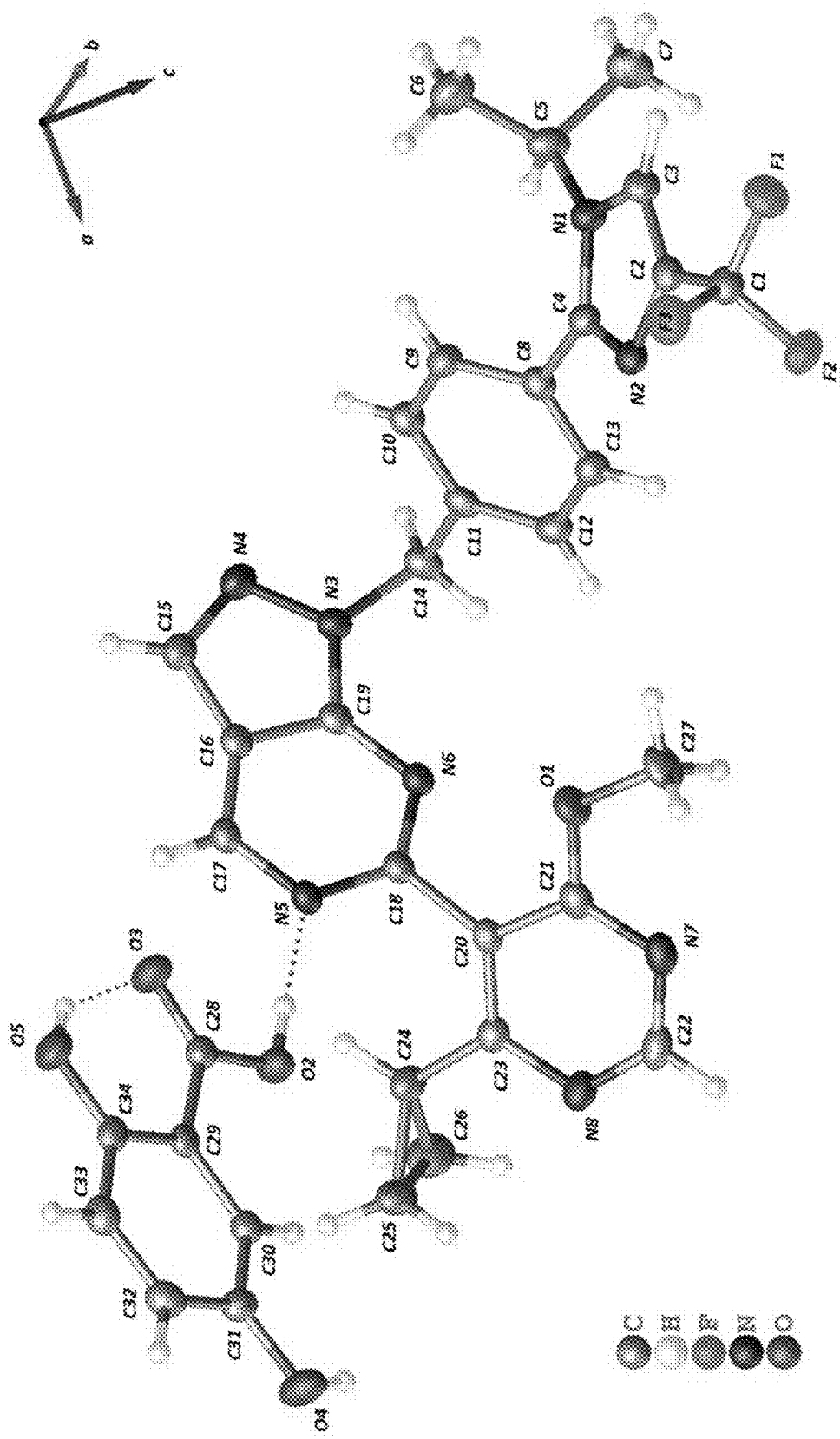
FIGURE 21: Asymmetric unit of crystalline Form 2 from a single crystal structure

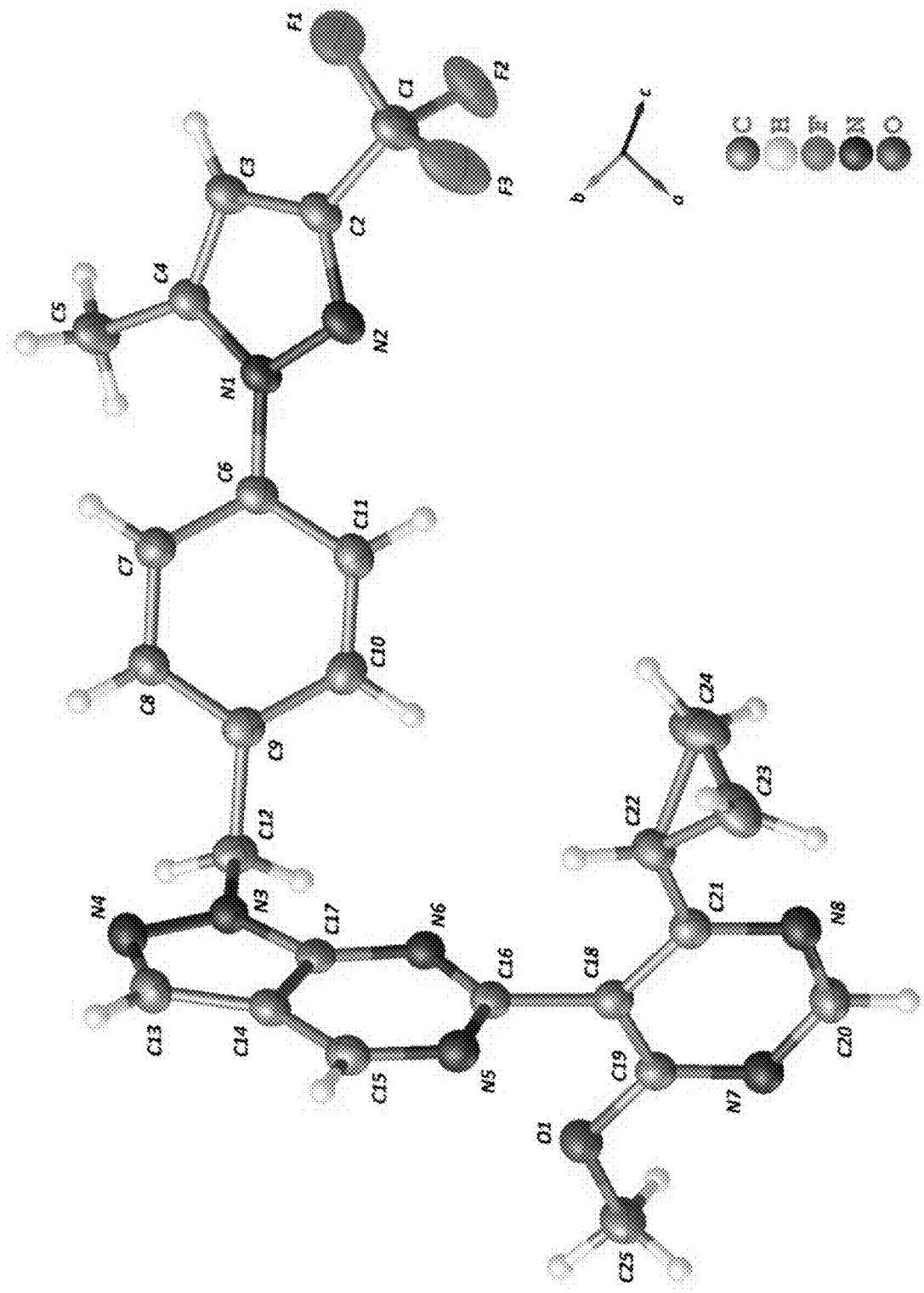
FIGURE 22: Asymmetric unit of crystalline Form A1 from a single crystal structure

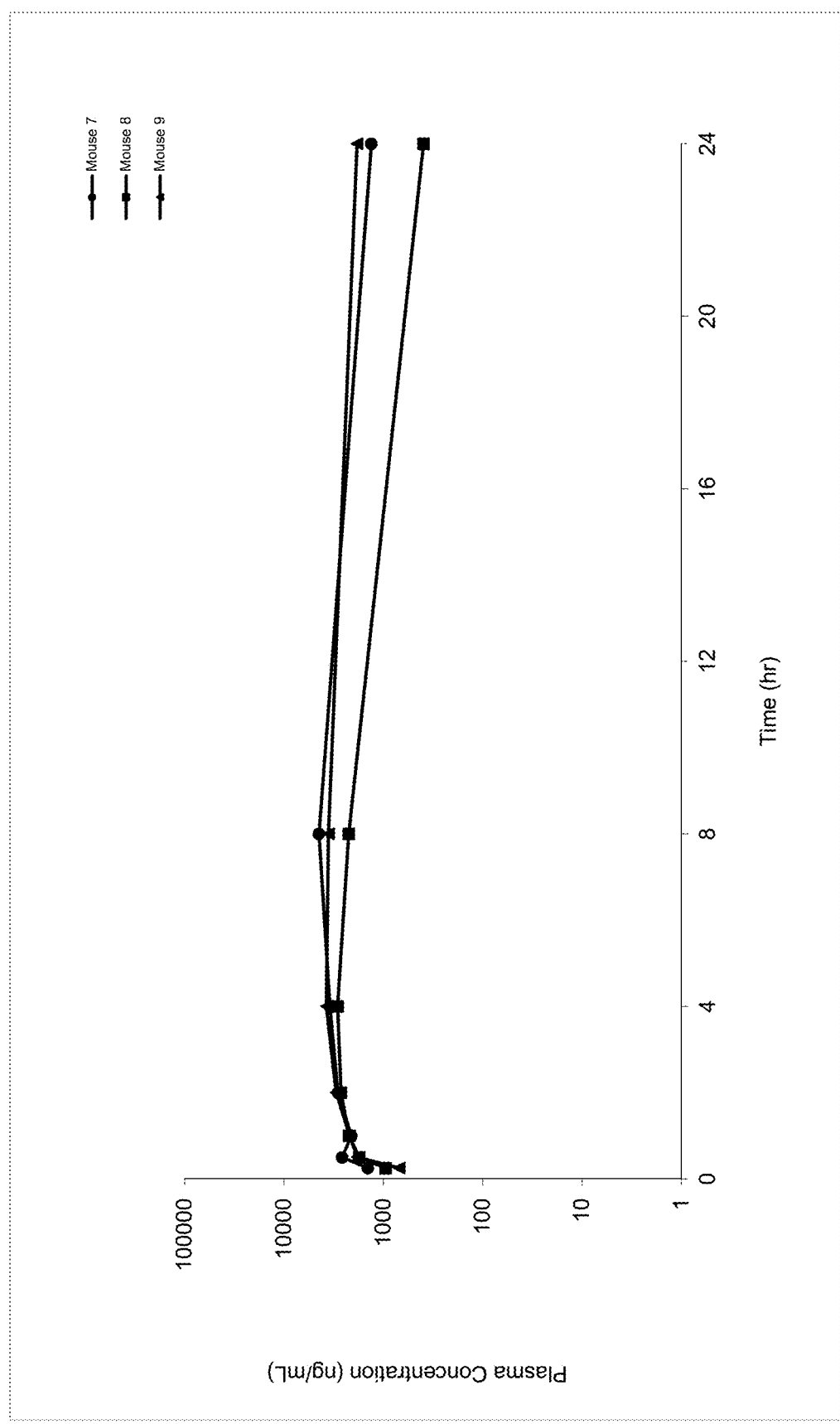
FIGURE 23: Plasma Concentration vs. Time Profile for Crystalline Form A after 300 mg/kg Dose in NOD/SCID Mice

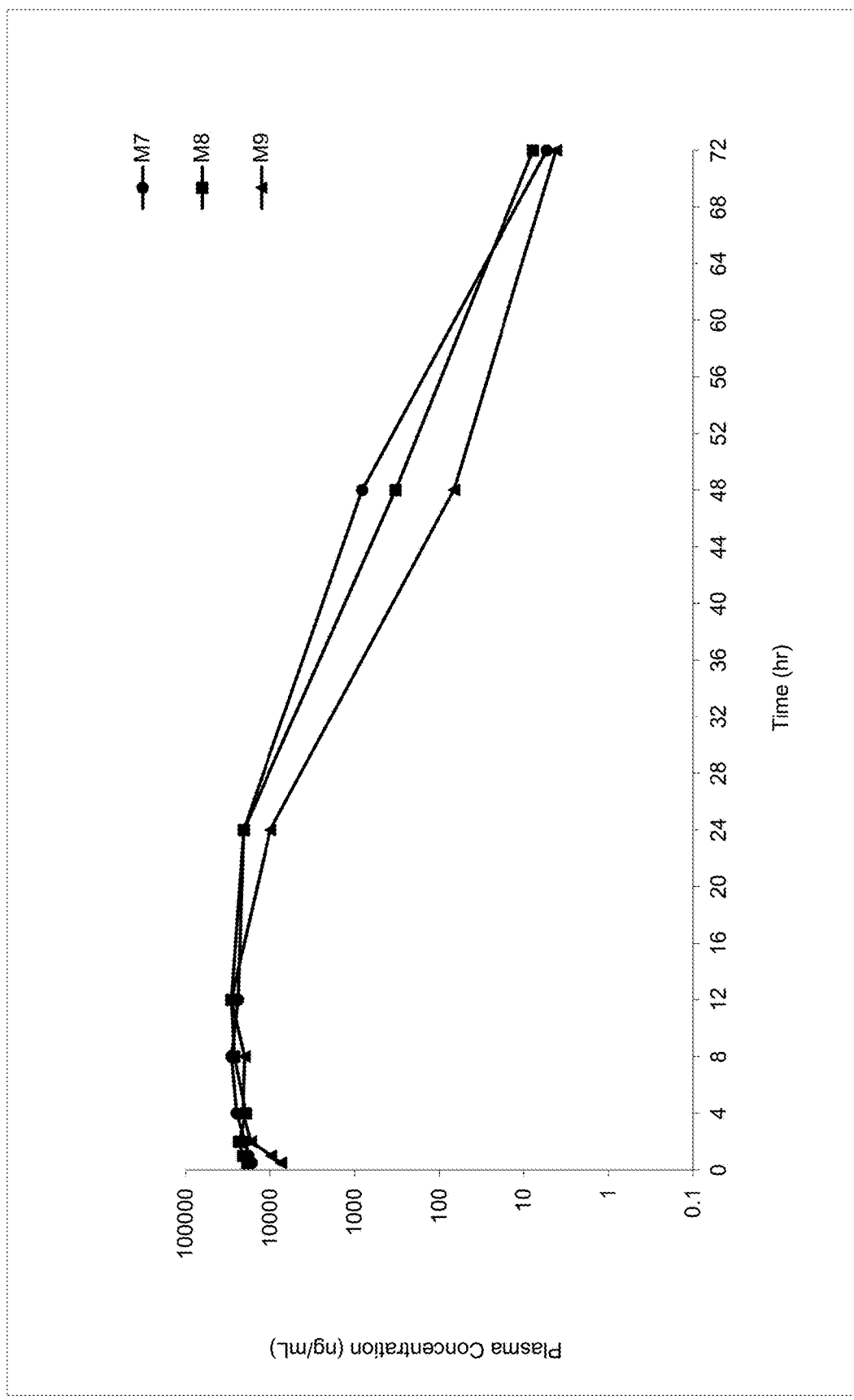
FIGURE 24: Plasma Concentration vs. Time Profile for Crystalline Form 2 after 300 mg/kg Dose in NOD/SCID Mice

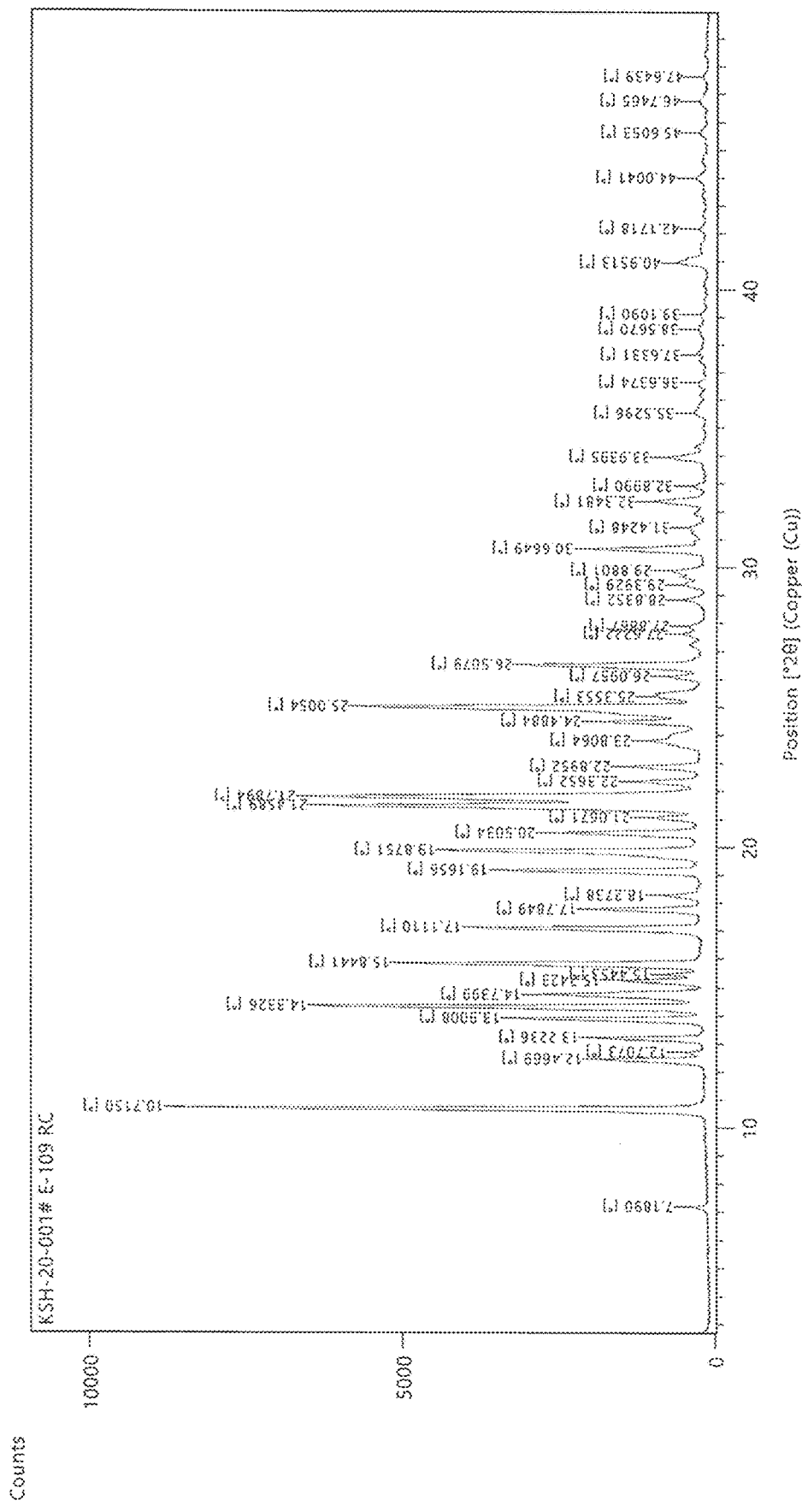
FIGURE 25. XRPD pattern corresponding to crystalline Form F

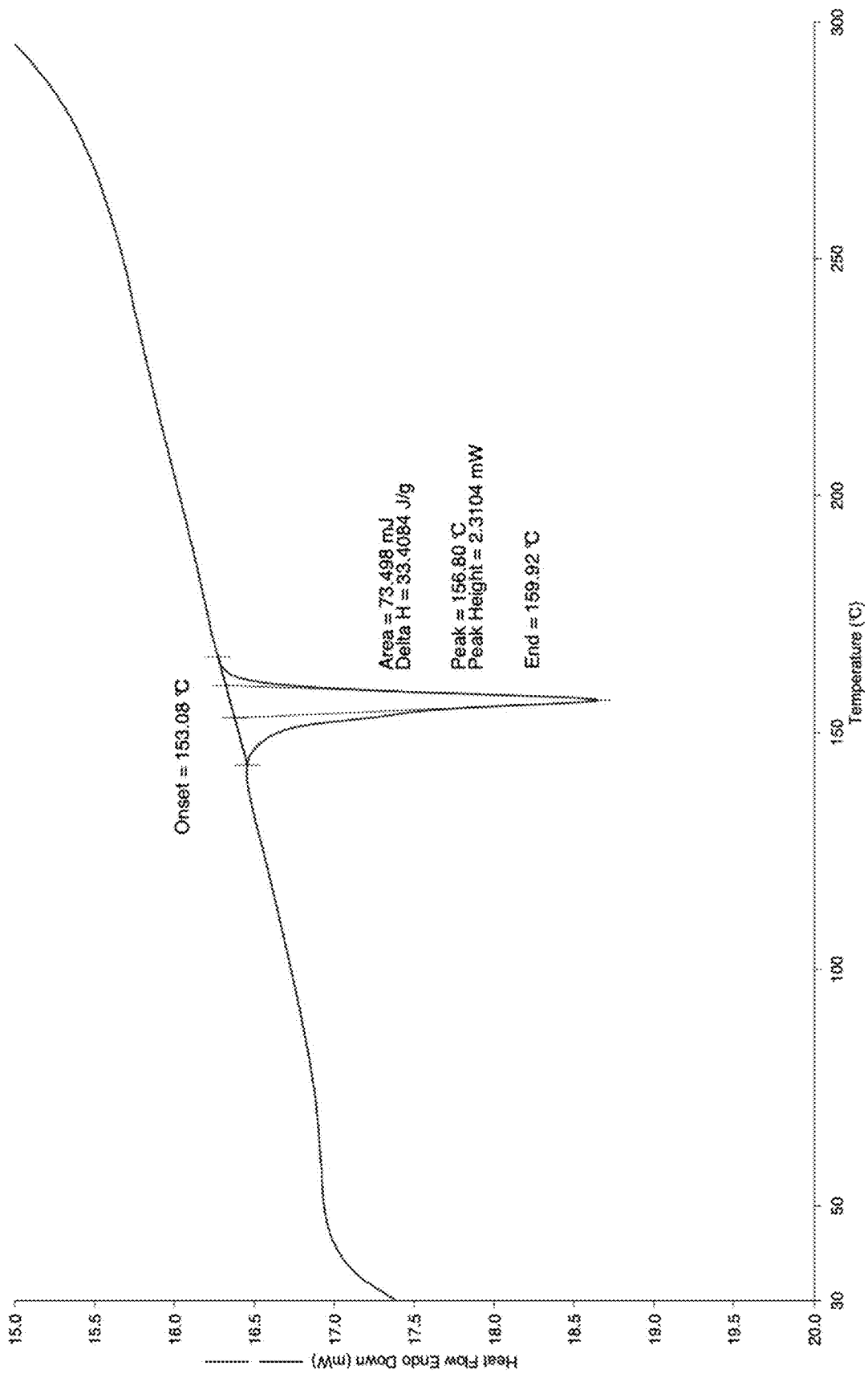
FIGURE 26. DSC thermogram corresponding to crystalline Form F

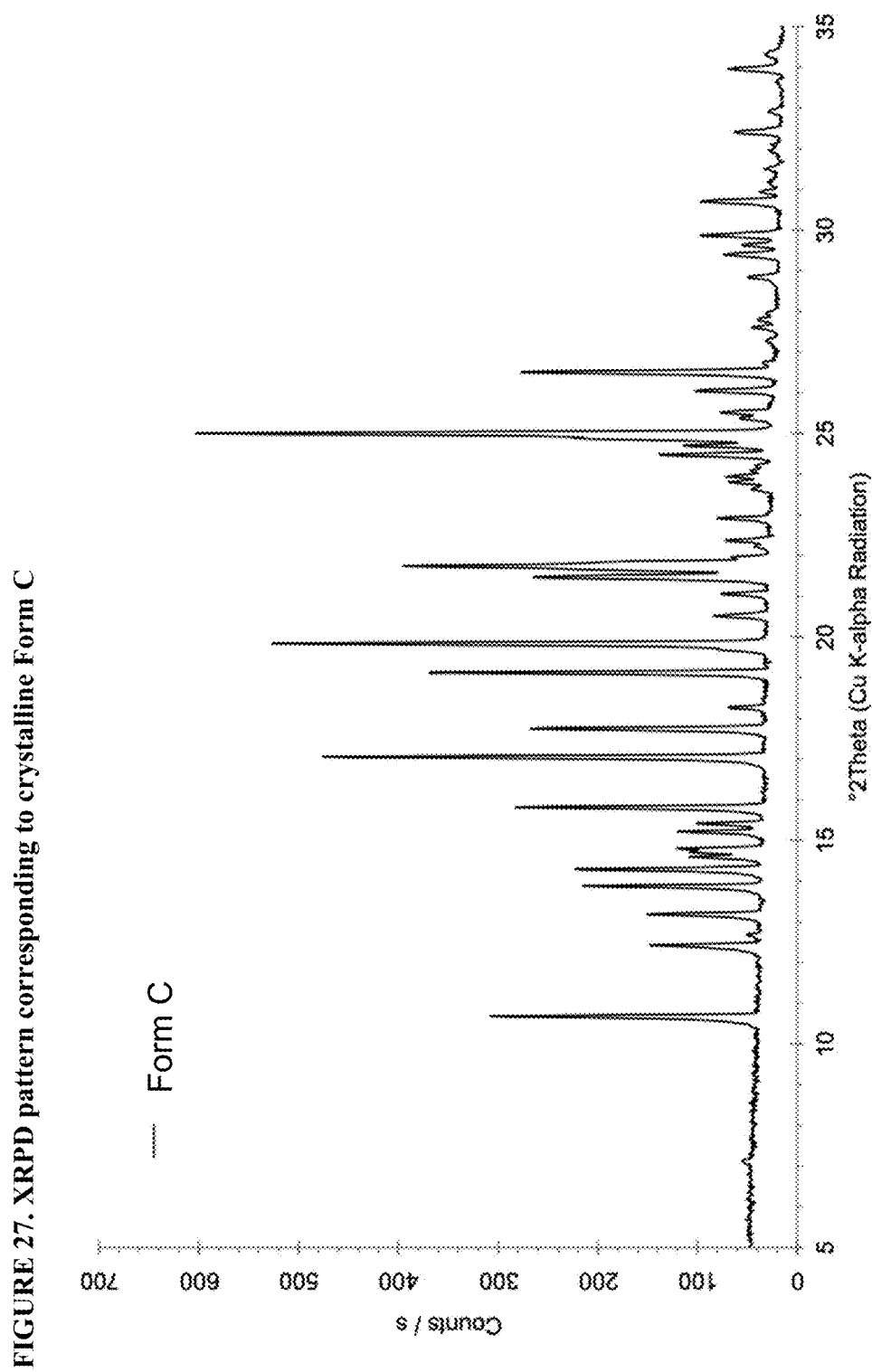
FIGURE 27. XRPD pattern corresponding to crystalline Form C

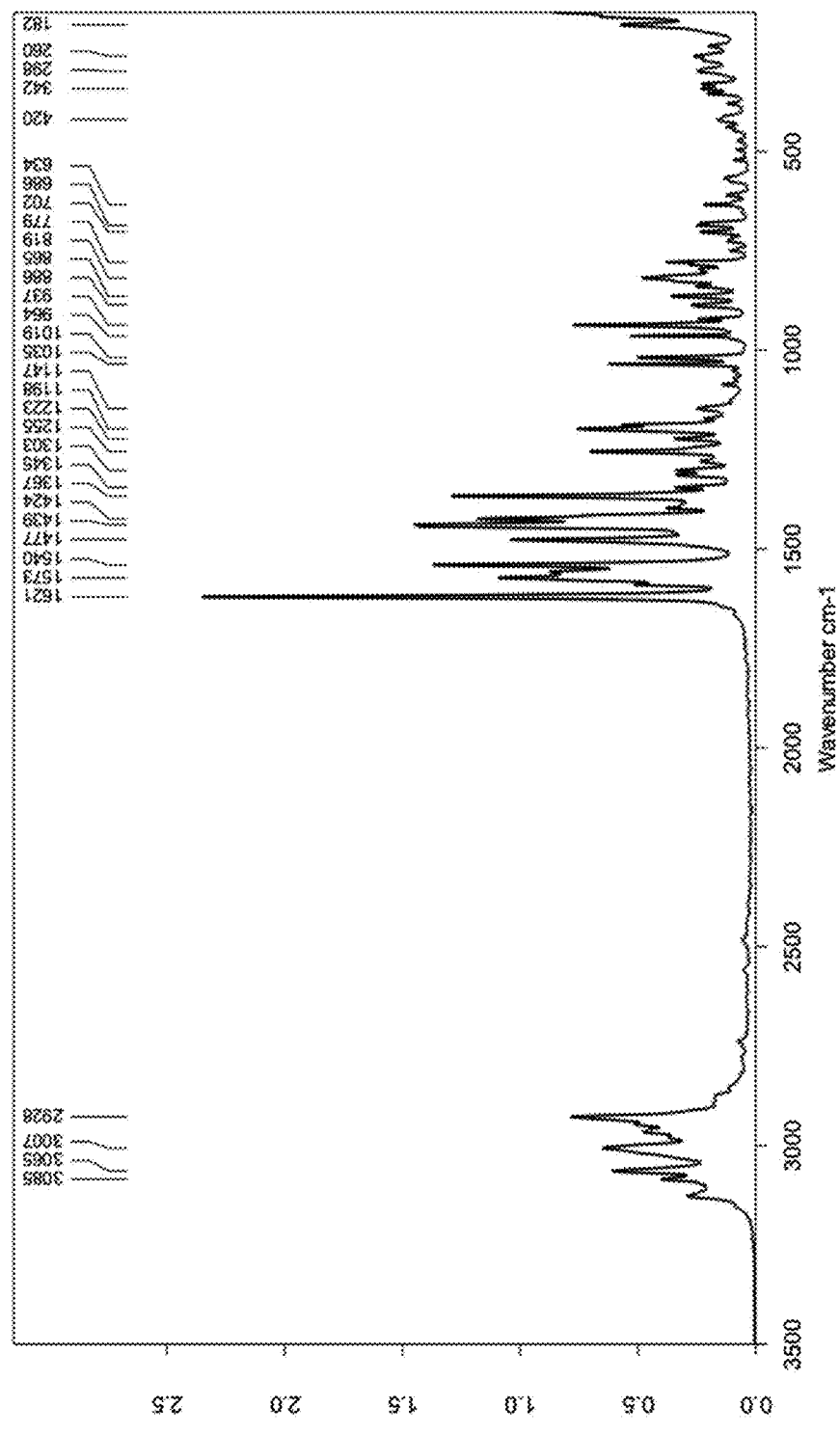
FIGURE 28. Raman spectrum corresponding to Form C

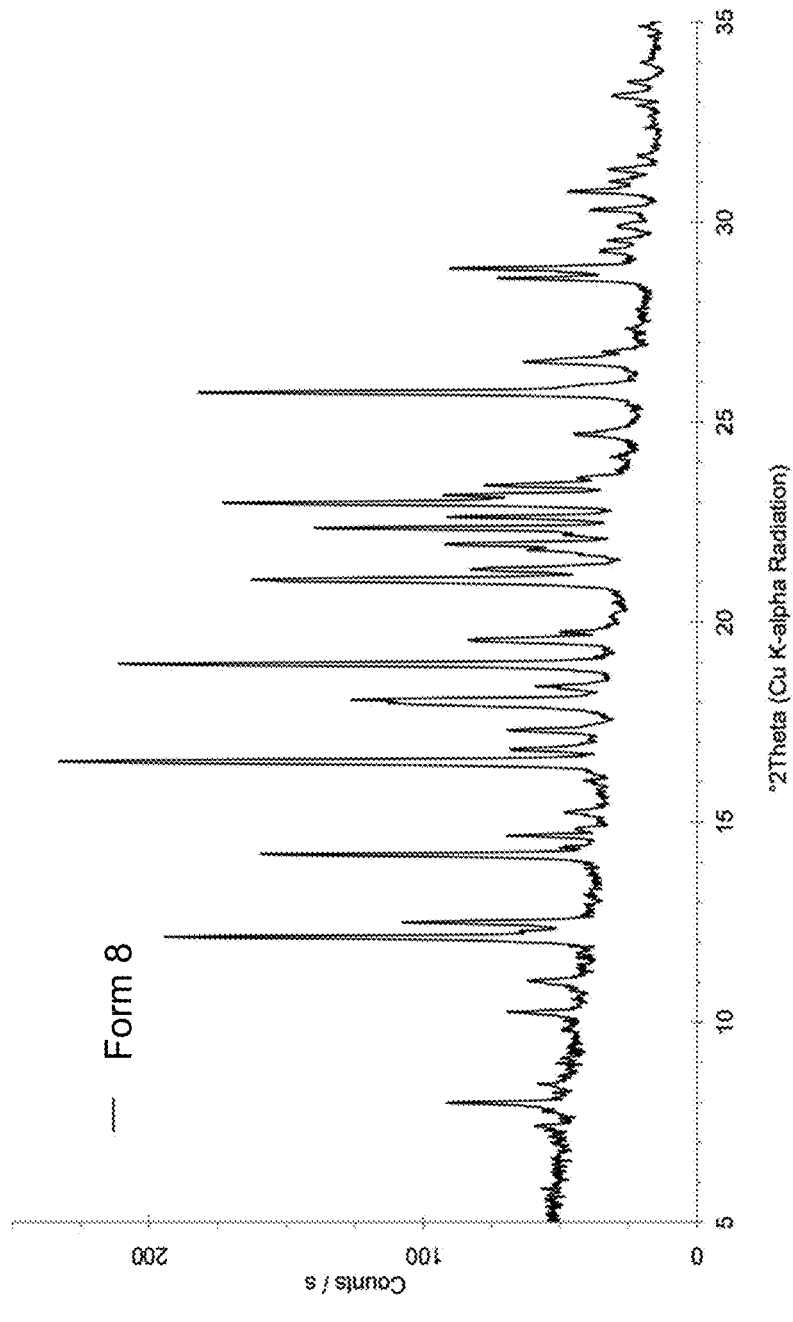
FIGURE 29. XRPD pattern corresponding to crystalline Form 8.

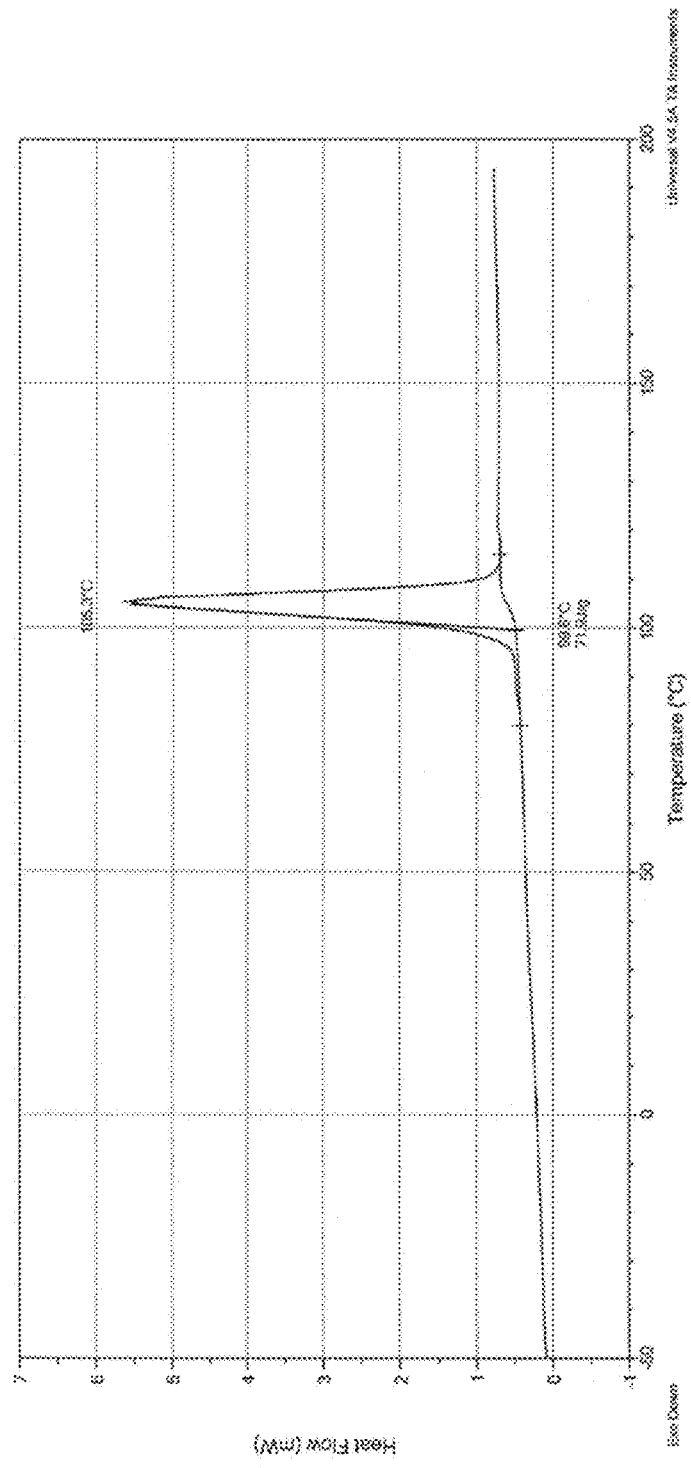
FIGURE 30. DSC thermogram corresponding to crystalline Form 8

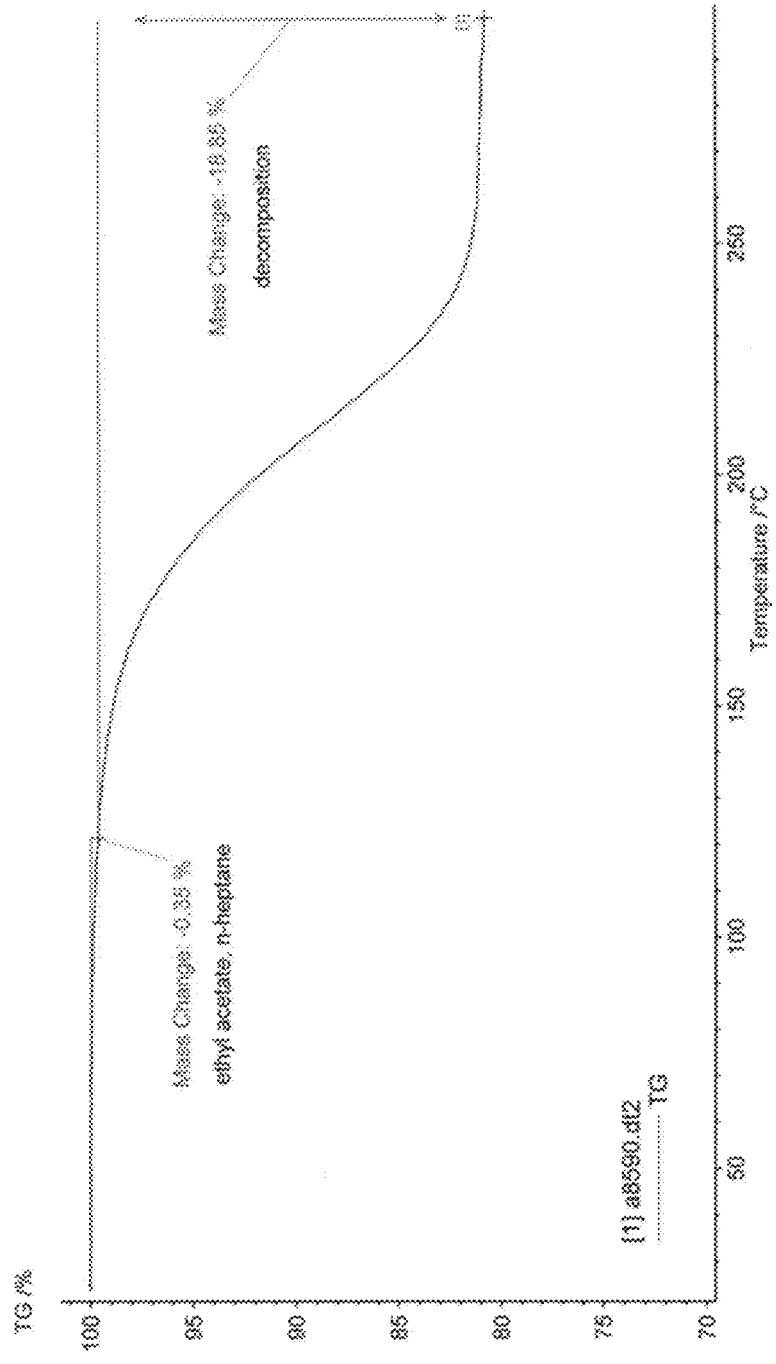
FIGURE 31. TG-FTIR thermogram corresponding to crystalline Form 8

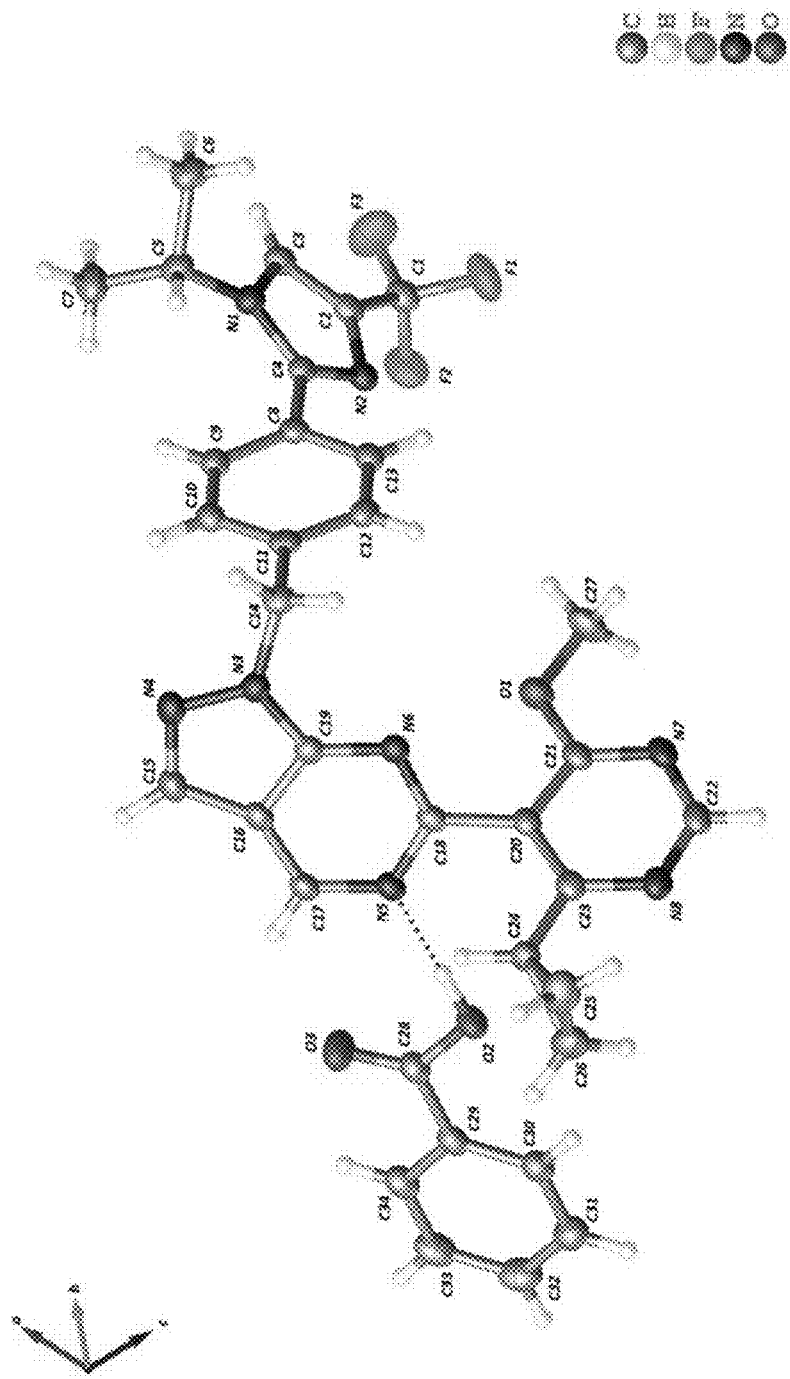
FIGURE 32. Asymmetric unit of crystalline Form 8 from a single crystal structure

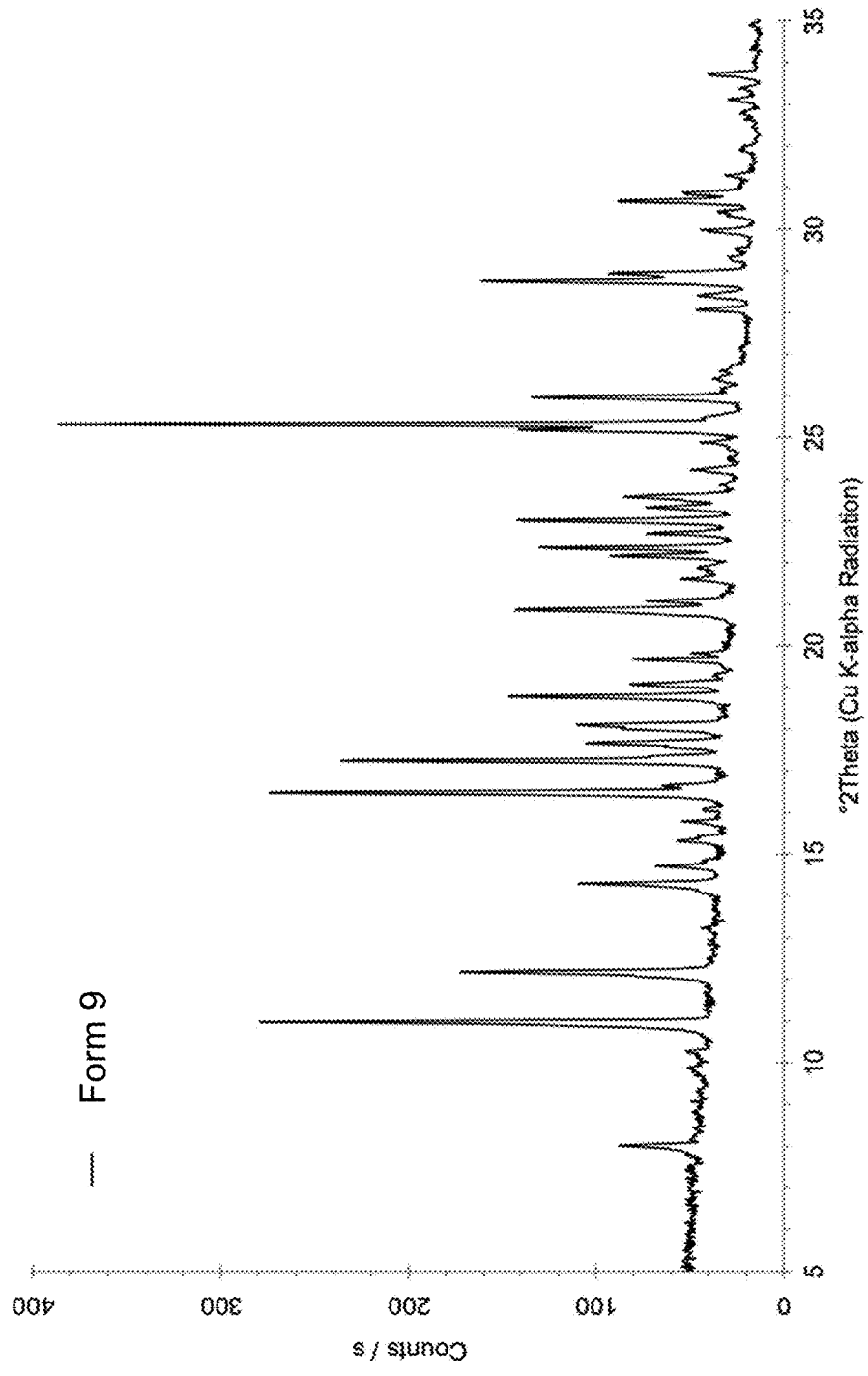
FIGURE 33. XRPD pattern corresponding to crystalline Form 9

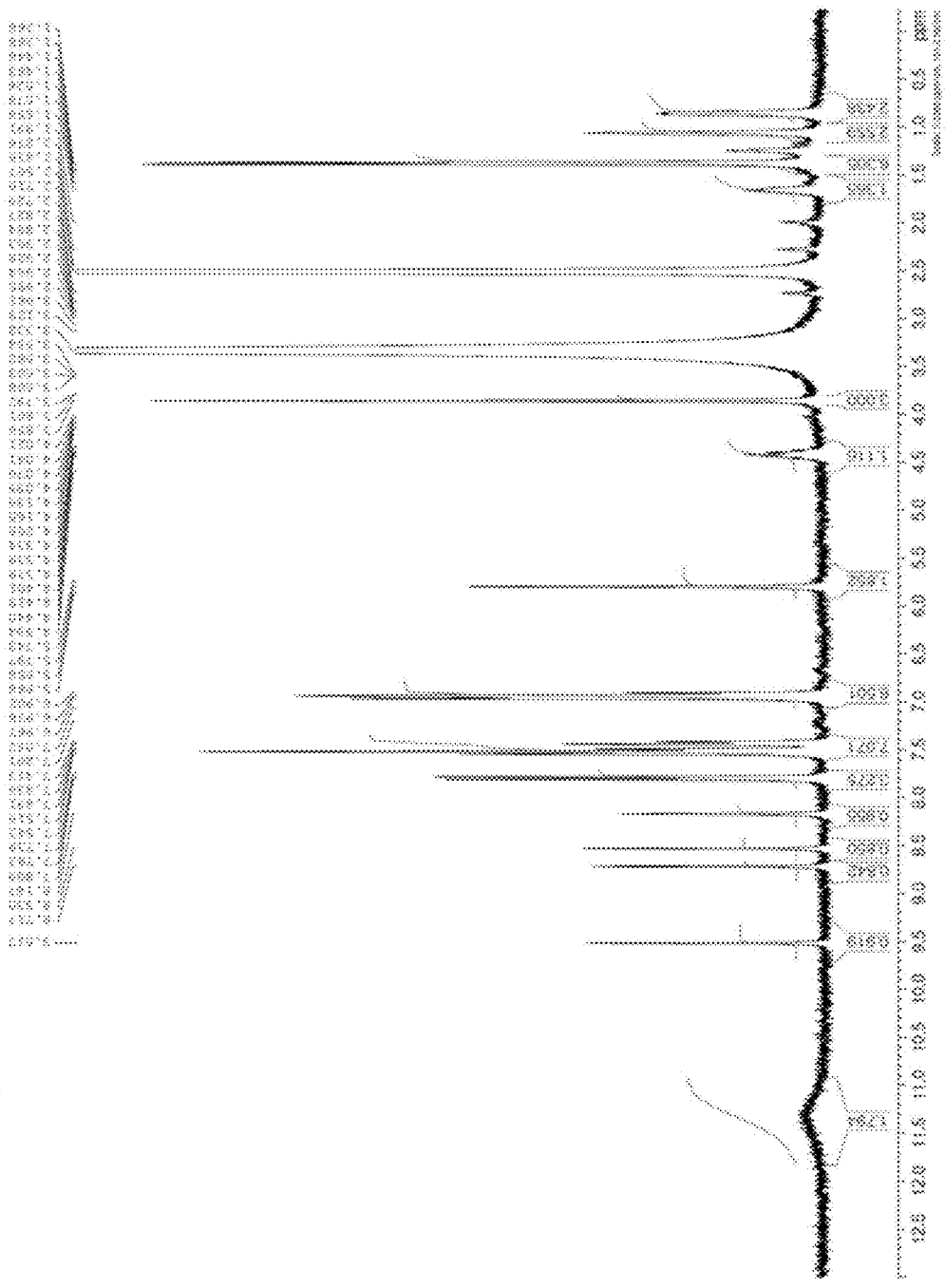
FIGURE 34. 1H NMR spectrum corresponding to crystalline Form 9

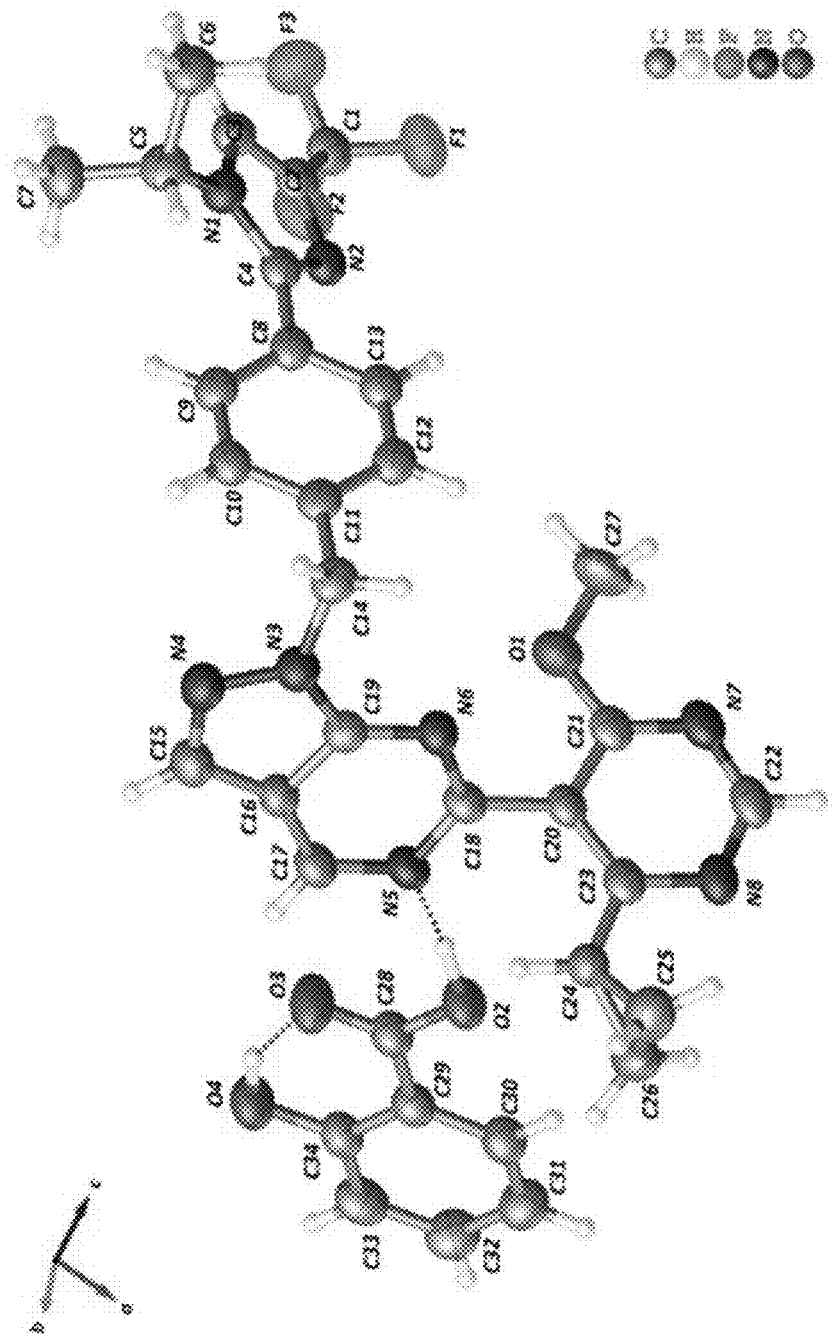
FIGURE 35. Asymmetric unit cell of crystalline Form 9.

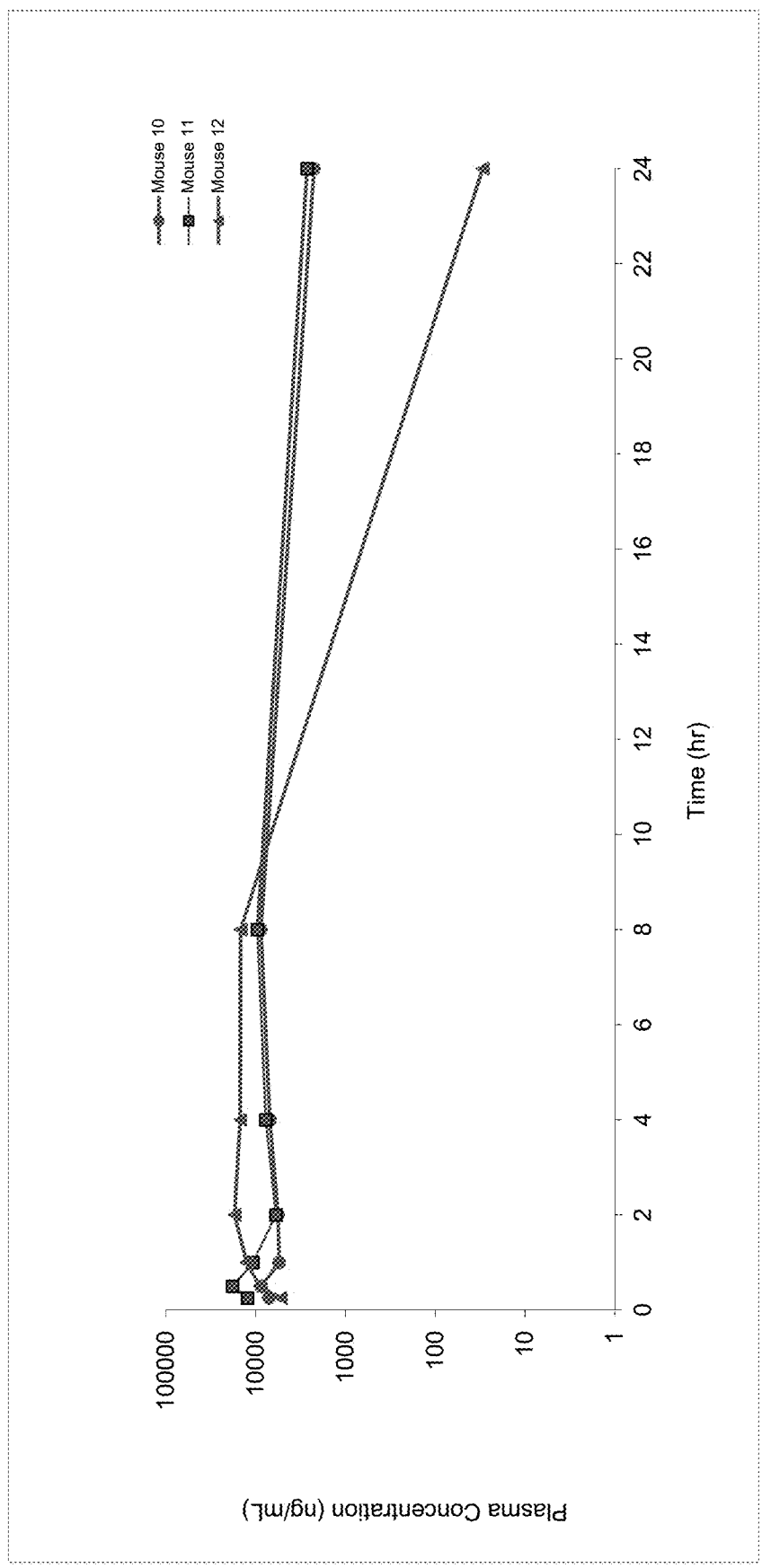
FIGURE 36. Plasma Concentration vs. Time Profile for Crystalline Form 8 after 300 mg/kg Dose in NOD/SCID Mice

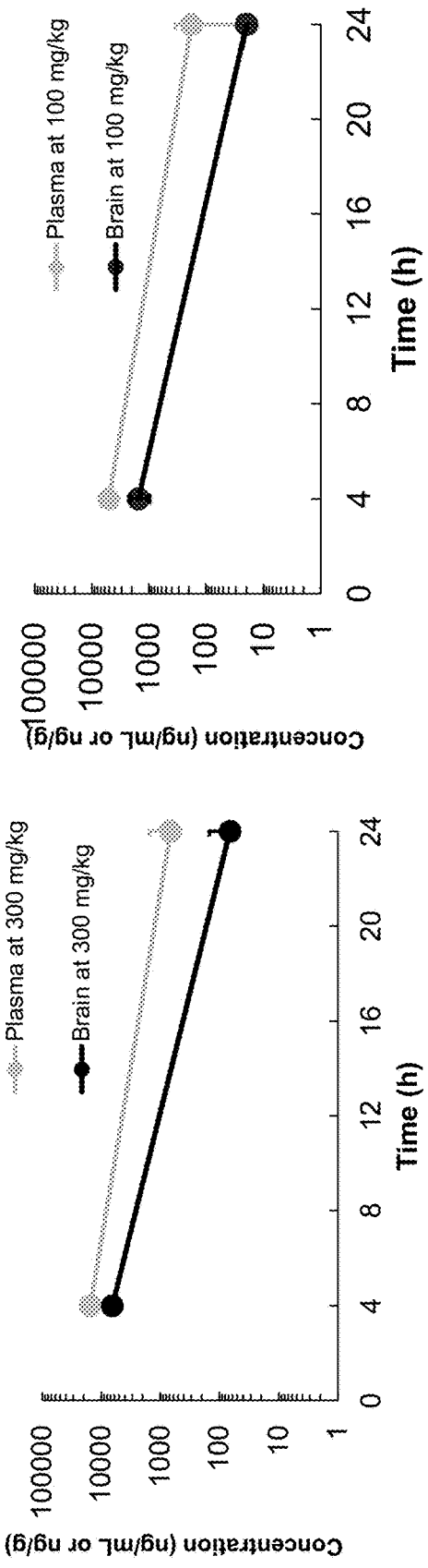
FIGURE 37. Brain and Plasma Concentration following 100 and 300 mg/kg QD repeated oral dose of crystalline Form 2 to NOD SCID Female Mice

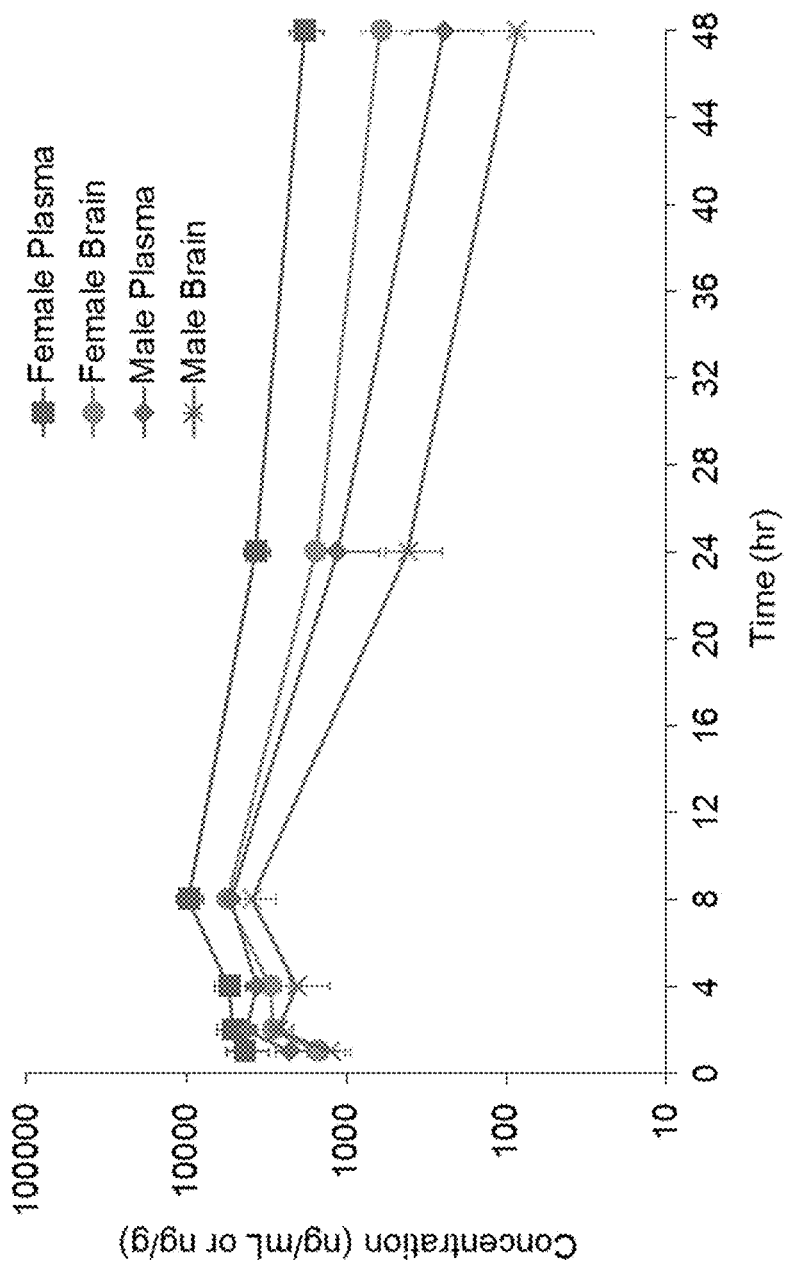
FIGURE 38. Brain and Plasma Concentration following a Single 100 mg/kg Oral Dose of Crystalline Form 2 to SD Male and Female Rats

SOLID STATE FORMS OF SUBSTITUTED PYRAZOLOPYRIMIDINES AND USES THEREOF

CROSS REFERENCE TO RELATED APPLICATIONS

This application claims the priority benefit of U.S. Provisional Application No. 63/107,765, filed Oct. 30, 2020, which is hereby incorporated by reference herein in its entirety.

FIELD OF THE INVENTION

The present disclosure relates to solid state forms of substituted pyrazolopyrimidines, pharmaceutical compositions thereof, methods of treating cancer by administering one or more solid state forms of substituted pyrazolopyrimidines, and methods for preparing solid state forms of substituted pyrazolopyrimidines.

BACKGROUND

Substituted pyrazolopyrimidines, such as 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) are inhibitors of ubiquitin-specific-processing protease 1 (USP1).

Not all compounds that are USP1 inhibitors have characteristics affording the best potential to become useful therapeutics. Some of these characteristics include high affinity at the USP1, duration of USP1 deactivation, oral bioavailability, solubility, and stability (e.g., ability to formulate, ability to crystallize, or shelf life). Favorable characteristics can lead to improved safety, tolerability, efficacy, therapeutic index, patient compliance, cost efficiency, manufacturing ease, etc.

In addition, the isolation and commercial-scale preparation of solid state forms of substituted pyrazolopyrimidines, such as 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) and corresponding pharmaceutical formulations having acceptable solid state properties (including chemical stability, thermal stability, solubility, hygroscopicity, and/or particle size), compound manufacturability (including yield, impurity rejection during crystallization, filtration properties, drying properties, and milling properties), and formulation feasibility (including stability with respect to pressure or compression forces during tableting) present a number of challenges.

Accordingly, there is a current need for one or more solid state forms of substituted pyrazolopyrimidines, such as 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) that have an acceptable balance of these properties and can be used in the preparation of pharmaceutically acceptable solid dosage forms.

BRIEF SUMMARY OF THE INVENTION

In one aspect, the present disclosure relates to a solid state form of a compound of Formula (I):

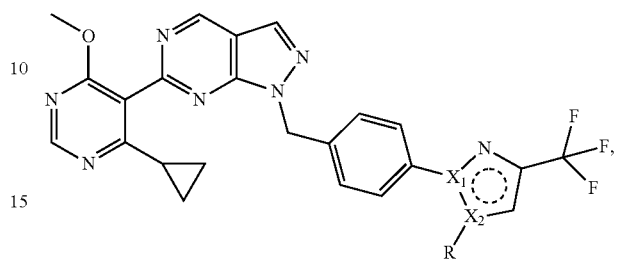

(I)

or a pharmaceutically acceptable salt thereof;
wherein:
R is $C_{1-3}$ alkyl; and
$X_1$ and $X_2$ are independently selected from the group consisting of N and C.

In some embodiments, the solid state form is a solid state form of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

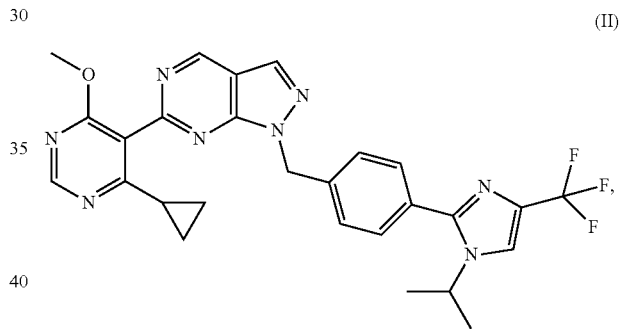

(II)

or a pharmaceutically acceptable salt thereof.

In some embodiments, the solid state form is a crystalline form of a compound of Formula (II). In some embodiments, the crystalline form is a hydrate, anhydrate, or solvate thereof. In some embodiments, the solvate is a dichloromethane solvate.

In some embodiments, the solid state form is an amorphous form of a compound of Formula (II). In some embodiments, the amorphous form is a hydrate, anhydrate, or solvate thereof.

In some embodiments, the solid state form of a compound of Formula (II) is selected from the group consisting of:
  a) crystalline Form A, wherein Form A is characterized by an XRPD pattern having peaks at 14.3±0.2, 21.5±0.2, and 21.8±0.2 degrees two theta;
  b) crystalline Form C, wherein Form C is characterized by an XRPD pattern having peaks at 14.2±0.2, 17.0±0.2, and 19.1±0.2 degrees two theta;
  c) crystalline Form D, wherein Form D is characterized by an XRPD pattern having peaks at 13.9±0.2, 15.2±0.2, and 19.3±0.2 degrees two theta;
  d) crystalline Form E, wherein Form E is characterized by an XRPD pattern having peaks at 10.6±0.2, 18.7±0.2, and 20.9±0.2 degrees two theta; and e) crystalline Form F, wherein Form F is characterized by an XRPD pattern having peaks at 10.7±0.2, 14.3±0.2, and 21.8±0.2 degrees two theta.

In some embodiments, the solid state form of a compound of Formula (II) is selected from the group consisting of:
  a) crystalline Form A, wherein Form A is characterized by an XRPD pattern having peaks at 14.3±0.2, 21.5±0.2, and 21.8±0.2 degrees two theta;
  b) crystalline Form C, wherein Form C is characterized by an XRPD pattern having peaks at 14.2±0.2, 17.0±0.2, and 19.1±0.2 degrees two theta;
  c) crystalline Form D, wherein Form D is characterized by an XRPD pattern having peaks at 13.9±0.2, 15.2±0.2, and 19.3±0.2 degrees two theta; and
  d) crystalline Form E, wherein Form E is characterized by an XRPD pattern having peaks at 10.6±0.2, 18.7±0.2, and 20.9±0.2 degrees two theta.

In some embodiments, the solid state form of a compound of Formula (II) is crystalline Form A. In some embodiments, crystalline Form A is characterized by an XRPD pattern as shown in FIG. 1. In some embodiments, crystalline Form A is characterized by an endothermic peak at about 165° C., as determined by DSC. In some embodiments, crystalline Form A is characterized by a DSC profile as shown in FIG. 2. In some embodiments, crystalline Form A is characterized by an about 0.93 wt % loss between room temperature and about 150° C., as determined by TGA. In some embodiments, crystalline Form A is characterized by a TGA profile as shown in FIG. 2.

In some embodiments, crystalline Form A is characterized by at least two of the following: a) an XRPD pattern as shown in FIG. 1; b) a DSC profile as shown in FIG. 2; or c) a TGA profile as shown in FIG. 2.

In some embodiments, crystalline Form A is substantially free of other polymorphic forms. In some embodiments, crystalline Form A has a polymorphic purity of at least 80%, or at least 85%, or at least 90%, or at least 95%, or at least 99%.

In some embodiments, crystalline Form A has a unit cell that indexes as monoclinic. In some embodiments, crystalline Form A has a unit cell with an a value of about 12.054 Å, a b value of about 8.775 Å, and a c value of about 24.837 Å. In some embodiments, crystalline Form A has a unit cell with a volume of about 2603.68 Å$^3$.

In another aspect, the present disclosure relates to a mixture comprising crystalline Form A and a second solid state form of a compound of Formula (II). In some embodiments, the present disclosure relates to a mixture comprising a majority of crystalline Form A as compared to other solid state forms of a compound of Formula (II). The compositions of mixtures of solid state forms disclosed herein can be determined using methods known in the art (see, for example, Varasteh, M., et al., *Int. J. Pharm.* 366(1-2): 74-81 (2009)).

In some embodiments, the solid state form of a compound of Formula (II) is crystalline Form C. In some embodiments, crystalline Form C is characterized by an XRPD pattern as shown in FIG. 3.

In some embodiments, crystalline Form C is substantially free of other polymorphic forms. In some embodiments, crystalline Form C has a polymorphic purity of at least 80%, or at least 85%, or at least 90%, or at least 95%, or at least 99%.

In another aspect, the present disclosure relates to a mixture comprising crystalline Form C and a second solid state form of a compound of Formula (II). In some embodiments, the present disclosure relates to a mixture comprising a majority of crystalline Form C as compared to other solid state forms of a compound of Formula (II).

In some embodiments, the solid state form of a compound of Formula (II) is crystalline Form D. In some embodiments, crystalline Form D is characterized by an XRPD pattern as shown in FIG. 4.

In some embodiments, crystalline Form D is substantially free of other polymorphic forms. In some embodiments, crystalline Form D has a polymorphic purity of at least 80%, or at least 85%, or at least 90%, or at least 95%, or at least 99%.

In another aspect, the present disclosure relates to a mixture comprising crystalline Form D and a second solid state form of a compound of Formula (II). In some embodiments, the present disclosure relates to a mixture comprising a majority of crystalline Form D as compared to other solid state forms of a compound of Formula (II).

In some embodiments, the solid state form of a compound of Formula (II) is crystalline Form E. In some embodiments, crystalline Form E is characterized by an XRPD pattern as shown in FIG. 5. In some embodiments, crystalline Form E is characterized by an endothermic peak at about 107° C., as determined by DSC. In some embodiments, crystalline Form E is characterized by a DSC profile as shown in FIG. 6. In some embodiments, crystalline Form E is characterized by an about 13.5 wt % loss between room temperature and about 200° C., as determined by TGA. In some embodiments, crystalline Form E is characterized by a TGA profile as shown in FIG. 6.

In some embodiments, crystalline Form E is characterized by at least two of the following: a) an XRPD pattern as shown in FIG. 5; b) a DSC profile as shown in FIG. 6; or c) a TGA profile as shown in FIG. 6.

In some embodiments, crystalline Form E is substantially free of other polymorphic forms. In some embodiments, crystalline Form E has a polymorphic purity of at least 80%, or at least 85%, or at least 90%, or at least 95%, or at least 99%.

In another aspect, the present disclosure relates to a mixture comprising crystalline Form E and a second solid state form of a compound of Formula (II). In some embodiments, the present disclosure relates to a mixture comprising a majority of crystalline Form E as compared to other solid state forms of a compound of Formula (II).

In some embodiments, the solid state form of a compound of Formula II is crystalline Form F. In some embodiments, crystalline Form F is characterized by an XRPD pattern as shown in FIG. 25. In some embodiments, crystalline Form F is characterized by an endothermic peak at about 157° C., as determined by DSC. In some embodiments, crystalline Form F is characterized by a DSC profile as shown in FIG. 26.

In some embodiments, crystalline Form F is characterized by at least one of the following: a) an XRPD pattern as shown in FIG. 25; or b) a DSC profile as shown in FIG. 26.

In some embodiments, crystalline Form F is substantially free of other polymorphic forms. In some embodiments, crystalline Form F has a polymorphic purity of at least 80%, or at least 85%, or at least 90%, or at least 95%, or at least 99%.

In another aspect, the present disclosure relates to a mixture comprising crystalline Form F and a second solid state form of a compound of Formula (II). In some embodiments, the present disclosure relates to a mixture comprising a majority of crystalline Form F as compared to other solid state forms of a compound of Formula (II).

In some embodiments, the solid state form of a compound of Formula (II) is a pharmaceutically acceptable salt of a compound of Formula (II).

In some embodiments, a pharmaceutically acceptable salt is formed between a compound of Formula (II) and a pharmaceutically acceptable acid. In some embodiments, the pharmaceutically acceptable acid is selected from the group consisting of 1-hydroxy-2-naphthoic acid, 4-aminosalicylic acid, ascorbic acid, adipic acid, L-aspartic acid, benzene sulfonic acid, benzoic acid, trans-cinnamic acid, citric acid, ethanedisulfonic acid, fumaric acid, galactaric acid, gentisic acid, gluconic acid, D-glucuronic acid, glutamic acid, glutaric acid, glycolic acid, hexanoic acid, hippuric acid, hydrobromic acid, hydrochloric acid, lactic acid, maleic acid, L-malic acid, malonic acid, R-mandelic acid, methanesulfonic acid, mucic acid, naphthalene sulfonic acid, nicotinic acid, oxalic acid, palmitic acid, p-toluene sulfonic acid, phosphoric acid, propionic acid, saccharin, salicylic acid, stearic acid, succinic acid, sulfuric acid, L-tartaric acid, vanillic acid, vanillin, ethyl maltol, gallic acid, gallic acid ethyl ester, 4-hydroxybenzoic acid, 4-hydroxybenzoic acid methyl ester, 3,4,5-trihydroxybenzoic acid, nicotinamide, L-proline, and D-sorbitol. In some embodiments, the pharmaceutically acceptable acid is selected from the group consisting of hydrochloric acid, hydrobromic acid, ethanedisulfonic acid, methanesulfonic acid, gentisic acid, benzoic acid, salicylic acid, and gallic acid. In some embodiments, the pharmaceutically acceptable acid is a benzoic acid derivative. In some embodiments, the pharmaceutically acceptable acid is a benzoic acid derivative substituted with one or more hydroxy groups. In some embodiments, the pharmaceutically acceptable acid is a benzoic acid derivative substituted with one hydroxy group. In some embodiments, the benzoic acid derivative substituted with one hydroxy group is salicylic acid. In some embodiments, the pharmaceutically acceptable acid is a benzoic acid derivative substituted with two hydroxy groups. In some embodiments, the benzoic acid derivative substituted with two hydroxy groups is gentisic acid. In some embodiments, the pharmaceutically acceptable acid is a benzoic acid derivative substituted with three hydroxy groups. In some embodiments, the benzoic acid derivative substituted with three hydroxy groups is gallic acid. In some embodiments, the benzoic acid derivative is selected from the group consisting of salicylic acid, gentisic acid, and gallic acid. In some embodiments, the pharmaceutically acceptable acid is hydrochloric acid. In some embodiments, the pharmaceutically acceptable acid is gentisic acid. In some embodiments the pharmaceutically acceptable acid is benzoic acid. In some embodiments the pharmaceutically acceptable acid is salicylic acid. In some embodiments the pharmaceutically acceptable acid is gallic acid.

In some embodiments, the solid state form of a compound of Formula (II) is a crystalline form of a pharmaceutically acceptable salt of a compound of Formula (II). In some embodiments, the crystalline form of the pharmaceutically acceptable salt is a hydrate, anhydrate, or solvate thereof.

In some embodiments, the solid state form of a compound of Formula (II) is an amorphous form of a pharmaceutically acceptable salt of a compound of Formula (II). In some embodiments, the amorphous form of the pharmaceutically acceptable salt is a hydrate, anhydrate, or solvate thereof.

In some embodiments, the pharmaceutically acceptable salt of a compound of Formula (II) is a hydrochloric acid salt. In some embodiments, the hydrochloric acid salt is crystalline Form 1 characterized by an XRPD pattern having peaks at 12.5±0.2, 22.4±0.2, and 23.9±0.2 degrees two theta.

In some embodiments, the hydrochloric acid salt is characterized by an XRPD pattern as shown in FIG. 7. In some embodiments, the hydrochloric acid salt is characterized by an endothermic peak at about 142.1° C., as determined by DSC. In some embodiments, the hydrochloric acid salt is characterized by a DSC profile as shown in FIG. 8. In some embodiments, the hydrochloric acid salt is characterized by an about 4.04 wt % loss between about 30° C. and about 100° C., as determined by TGA. In some embodiments, the hydrochloric acid salt is characterized by a TGA profile as shown in FIG. 8.

In some embodiments, crystalline Form 1 is characterized by at least two of the following: a) an XRPD pattern as shown in FIG. 7; b) a DSC profile as shown in FIG. 8; or c) a TGA profile as shown in FIG. 8.

In some embodiments, crystalline Form 1 is substantially free of other polymorphic forms. In some embodiments, crystalline Form 1 has a polymorphic purity of at least 80%, or at least 85%, or at least 90%, or at least 95%, or at least 99%.

In another aspect, the present disclosure relates to a mixture comprising crystalline Form 1 and a second solid state form of a compound of Formula (II). In some embodiments, the present disclosure relates to a mixture comprising a majority of crystalline Form 1 as compared to other solid state forms of a compound of Formula (II).

In some embodiments, the solid state form of a compound of Formula (II) is a pharmaceutically acceptable co-crystal of a compound of Formula (II) and a second pharmaceutically acceptable compound.

In some embodiments, a pharmaceutically acceptable co-crystal is formed between a compound of Formula (II) and a pharmaceutically acceptable acid. In some embodiments, the pharmaceutically acceptable acid is selected from the group consisting of 1-hydroxy-2-naphthoic acid, 4-aminosalicylic acid, ascorbic acid, adipic acid, L-aspartic acid, benzene sulfonic acid, benzoic acid, trans-cinnamic acid, citric acid, ethanedisulfonic acid, fumaric acid, galactaric acid, gentisic acid, gluconic acid, D-glucuronic acid, glutamic acid, glutaric acid, glycolic acid, hexanoic acid, hippuric acid, hydrobromic acid, hydrochloric acid, lactic acid, maleic acid, L-malic acid, malonic acid, R-mandelic acid, methanesulfonic acid, mucic acid, naphthalene sulfonic acid, nicotinic acid, oxalic acid, palmitic acid, p-toluene sulfonic acid, phosphoric acid, propionic acid, saccharin, salicylic acid, stearic acid, succinic acid, sulfuric acid, L-tartaric acid, vanillic acid, vanillin, ethyl maltol, gallic acid, gallic acid ethyl ester, 4-hydroxybenzoic acid, 4-hydroxybenzoic acid methyl ester, 3,4,5-trihydroxybenzoic acid, nicotinamide, L-proline, and D-sorbitol. In some embodiments, the pharmaceutically acceptable acid is selected from the group consisting of hydrochloric acid, hydrobromic acid, ethanedisulfonic acid, methanesulfonic acid, gentisic acid, benzoic acid, salicylic acid, and gallic acid. In some embodiments, the pharmaceutically acceptable acid is selected from the group consisting of hydrochloric acid, hydrobromic acid, ethanedisulfonic acid, methanesulfonic acid, and gentisic acid. In some embodiments, the pharmaceutically acceptable acid is a benzoic acid derivative. In some embodiments, the pharmaceutically acceptable acid is a benzoic acid derivative substituted with one or more hydroxy groups. In some embodiments, the pharmaceutically acceptable acid is a benzoic acid derivative substituted with one hydroxy group. In some embodiments, the benzoic acid derivative substituted with one hydroxy group is salicylic acid. In some embodiments, the pharmaceutically acceptable acid is a benzoic acid derivative substituted with two hydroxy groups. In some embodiments, the benzoic acid derivative substituted with two hydroxy groups is gentisic acid. In some embodiments, the pharmaceutically acceptable acid is a benzoic acid derivative substituted with three hydroxy groups. In some embodiments, the benzoic acid derivative substituted with three hydroxy groups is gallic acid. In some embodiments, the benzoic acid derivative is selected from the group consisting of salicylic acid, gentisic acid, and gallic acid. In some embodiments, the pharmaceutically acceptable acid is hydrochloric acid. In some embodiments, the pharmaceutically acceptable acid is gentisic acid. In some embodiments, the pharmaceutically acceptable acid is benzoic acid. In some embodiments, the pharmaceutically acceptable acid is salicylic acid. In some embodiments the pharmaceutically acceptable acid is gallic acid.

In some embodiments, the pharmaceutically acceptable co-crystal of a compound of Formula (II) is a gentisic acid co-crystal. In some embodiments, the gentisic acid co-crystal is crystalline Form 2 characterized by an XRPD pattern having peaks at 16.6±0.2, 18.7±0.2, and 22.5±0.2 degrees two theta. In some embodiments, the gentisic acid co-crystal is characterized by an XRPD pattern as shown in FIG. 9. In some embodiments, the gentisic acid co-crystal is characterized by an endothermic peak at about 186.0° C., as determined by DSC. In some embodiments, the gentisic acid co-crystal is characterized by a DSC profile as shown in FIG. 10. In some embodiments, the gentisic acid co-crystal is characterized by an about 3.17 wt % loss between room temperature and about 170° C., as determined by TGA. In some embodiments, the gentisic acid co-crystal is characterized by a TGA profile as shown in FIG. 10.

In some embodiments, crystalline Form 2 is characterized by at least two of the following: a) an XRPD pattern as shown in FIG. 9; b) a DSC profile as shown in FIG. 10; or c) a TGA profile as shown in FIG. 10.

In some embodiments, crystalline Form 2 is substantially free of other polymorphic forms. In some embodiments, crystalline Form 2 has a polymorphic purity of at least 80%, or at least 85%, or at least 90%, or at least 95%, or at least 99%.

In some embodiments, crystalline Form 2 has a unit cell that indexes as monoclinic. In some embodiments, crystalline Form 2 has a unit cell with an a value of about 11.113 Å, a b value of about 12.356 Å, and a c value of about 24.048 Å. In some embodiments, crystalline Form 2 has a unit cell with a volume of about 3223.93 Å$^3$.

In another aspect, the present disclosure relates to a mixture comprising crystalline Form 2 and a second solid state form of a compound of Formula (II). In some embodiments, the present disclosure relates to a mixture comprising a majority of crystalline Form 2 as compared to other solid state forms of a compound of Formula (II).

In some embodiments, the pharmaceutically acceptable co-crystal of a compound of Formula (II) is a benzoic acid co-crystal. In some embodiments, the benzoic acid co-crystal is crystalline Form 8 characterized by an XRPD pattern having peaks at 12.1±0.2, 14.2±0.2, and 16.5±0.2 degrees two theta. In some embodiments, the benzoic acid co-crystal is characterized by an XRPD pattern as shown in FIG. 29. In some embodiments, the benzoic acid co-crystal is characterized by an endothermic peak at about 105° C., as determined by DSC. In some embodiments, the benzoic acid co-crystal is characterized by a DSC profile as shown in FIG. 30.

In some embodiments, the benzoic acid cocrystal is characterized by an about 18.8% wt loss between about 120° C. and 300° C. In some embodiments, the benzoic acid co-crystal is characterized by a TG-FTIR profile as shown in FIG. 31.

In some embodiments, crystalline Form 8 is characterized by at least two of the following: a) an XRPD pattern as shown in FIG. 29; b) a DSC profile as shown in FIG. 30; or c) a TG-FTIR profile as shown in FIG. 31.

In some embodiments, crystalline Form 8 is substantially free of other polymorphic forms. In some embodiments, crystalline Form 8 has a polymorphic purity of at least 80%, or at least 85%, or at least 90%, or at least 95%, or at least 99%.

In some embodiments, crystalline Form 8 has a unit cell that indexes as monoclinic. In some embodiments, crystalline Form 8 has a unit cell with an a value of about 10.61070(10) Å, a b value of about 12.39940(10) Å, and a c value of about 24.15170(10) Å. In some embodiments, crystalline Form 8 has a unit cell with a volume of about 3114.74(4) Å$^3$.

In another aspect, the present disclosure relates to a mixture comprising crystalline Form 8 and a second solid state form of a compound of Formula (II). In some embodiments, the present disclosure relates to a mixture comprising a majority of crystalline Form 8 as compared to other solid state forms of a compound of Formula (II).

In some embodiments, the pharmaceutically acceptable co-crystal of a compound of Formula (II) is a salicylic acid co-crystal. In some embodiments, the salicylic acid co-crystal is crystalline Form 9 characterized by an XRPD pattern having peaks at 11.0±0.2, 16.5±0.2, 17.3±0.2 and 25.3±0.2 degrees two theta. In some embodiments, the salicylic acid co-crystal is characterized by an XRPD pattern as shown in FIG. 33. In some embodiments, the salicylic acid co-crystal is characterized by an $^1$H NMR spectrum as shown in FIG. 34.

In some embodiments, crystalline Form 9 is characterized by at least one of the following: a) an XRPD pattern as shown in FIG. 33; orb) an $^1$H NMR profile as shown in FIG. 34.

In some embodiments, crystalline Form 9 is substantially free of other polymorphic forms. In some embodiments, crystalline Form 9 has a polymorphic purity of at least 80%, or at least 85%, or at least 90%, or at least 95%, or at least 99%.

In some embodiments, crystalline Form 9 has a unit cell that indexes as monoclinic. In some embodiments, crystalline Form 9 has a unit cell with an a value of about 10.8387(11) Å, a b value of about 12.3761(12) Å, and a c value of about 24.242(2) A. In some embodiments, crystalline Form 9 has a unit cell with a volume of about 3173.1(5) Å$^3$.

In another aspect, the present disclosure relates to a mixture comprising crystalline Form 9 and a second solid state form of a compound of Formula (II). In some embodiments, the present disclosure relates to a mixture comprising a majority of crystalline Form 9 as compared to other solid state forms of a compound of Formula (II).

In some embodiments, the solid state form is a solid state form of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III):

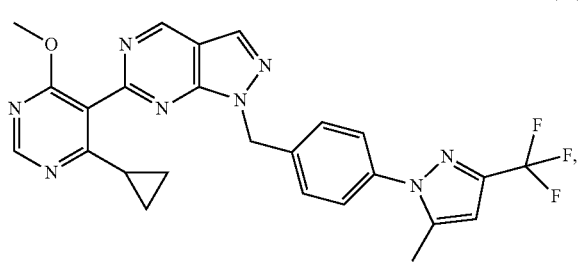

(III)

or a pharmaceutically acceptable salt thereof.

In some embodiments, the solid state form is a crystalline form of a compound of Formula (III). In some embodiments, the crystalline form is a hydrate, anhydrate, or solvate thereof.

In some embodiments, the solid state form is an amorphous form of a compound of Formula (III). In some embodiments, the amorphous form is a hydrate, anhydrate, or solvate thereof.

In some embodiments, the solid state form of a compound of Formula (III) is selected from the group consisting of:
 a) crystalline Form A1, wherein Form A1 is characterized by an XRPD pattern having peaks at 16.1±0.2, 16.7±0.2, and 24.8±0.2 degrees two theta; and
 b) crystalline Form B1, wherein Form B1 is characterized by an XRPD pattern having peaks at 12.9±0.2, 14.5±0.2, and 22.6±0.2 degrees two theta.

In some embodiments, the solid state form of a compound of Formula (III) is crystalline Form A1. In some embodiments, crystalline Form A1 is characterized by an XRPD pattern as shown in FIG. 11. In some embodiments, crystalline Form A1 is characterized by an endothermic peak at about 150.5° C., as determined by DSC. In some embodiments, crystalline Form A1 is characterized by a DSC profile as shown in FIG. 12. In some embodiments, crystalline Form A1 is characterized by an about 0.95 wt % loss between room temperature and about 120° C., as determined by TGA. In some embodiments, crystalline Form A1 is characterized by a TGA profile as shown in FIG. 12.

In some embodiments, crystalline Form A1 is characterized by at least two of the following: a) an XRPD pattern as shown in FIG. 11; b) a DSC profile as shown in FIG. 12; or c) a TGA profile as shown in FIG. 12.

In some embodiments, crystalline Form A1 is substantially free of other polymorphic forms. In some embodiments, crystalline Form A1 has a polymorphic purity of at least 80%, or at least 85%, or at least 90%, or at least 95%, or at least 99%.

In some embodiments, crystalline Form A1 has a unit cell that indexes as monoclinic. In some embodiments, crystalline Form A1 has a unit cell with an a value of about 12.545 Å, a b value of about 8.640 Å, and a c value of about 21.660 Å. In some embodiments, crystalline Form A1 has a unit cell with a volume of about 2336.13 Å$^3$.

In another aspect, the present disclosure relates to a mixture comprising crystalline Form A1 and a second solid state form of a compound of Formula (III). In some embodiments, the present disclosure relates to a mixture comprising a majority of crystalline Form A1 as compared to other solid state forms of a compound of Formula (III).

In some embodiments, the solid state form of a compound of Formula (III) is crystalline Form B1. In some embodiments, crystalline Form B1 is characterized by an XRPD pattern as shown in FIG. 13. In some embodiments, crystalline Form B1 is characterized by an endothermic peak at about 161.2° C., as determined by DSC. In some embodiments, crystalline Form B1 is characterized by a DSC profile as shown in FIG. 14. In some embodiments, crystalline Form B1 is characterized by an about 1.58 wt % loss between room temperature and about 120° C., as determined by TGA. In some embodiments, crystalline Form B1 is characterized by a TGA profile as shown in FIG. 14.

In some embodiments, crystalline Form B1 is characterized by at least two of the following: a) an XRPD pattern as shown in FIG. 13; b) a DSC profile as shown in FIG. 14; or c) a TGA profile as shown in FIG. 14.

In some embodiments, crystalline Form B1 is substantially free of other polymorphic forms. In some embodiments, crystalline Form B1 has a polymorphic purity of at least 80%, or at least 85%, or at least 90%, or at least 95%, or at least 99%.

In another aspect, the present disclosure relates to a mixture comprising crystalline Form B1 and a second solid state form of a compound of Formula (III). In some embodiments, the present disclosure relates to a mixture comprising a majority of crystalline Form B1 as compared to other solid state forms of a compound of Formula (III).

In some embodiments, the solid state form of a compound of Formula (III) is a pharmaceutically acceptable salt or co-crystal of a compound of Formula (III).

In some embodiments, a pharmaceutically acceptable salt or co-crystal is formed between a compound of Formula (III) and a pharmaceutically acceptable acid. In some embodiments, the pharmaceutically acceptable acid is selected from the group consisting of 1-hydroxy-2-naphthoic acid, 4-aminosalicylic acid, ascorbic acid, adipic acid, L-aspartic acid, benzene sulfonic acid, benzoic acid, trans-cinnamic acid, citric acid, ethanedisulfonic acid, fumaric acid, galactaric acid, gentisic acid, gluconic acid, D-glucuronic acid, glutamic acid, glutaric acid, glycolic acid, hexanoic acid, hippuric acid, hydrobromic acid, hydrochloric acid, lactic acid, maleic acid, L-malic acid, malonic acid, R-mandelic acid, methanesulfonic acid, mucic acid, naphthalene sulfonic acid, nicotinic acid, oxalic acid, palmitic acid, p-toluene sulfonic acid, phosphoric acid, propionic acid, saccharin, salicylic acid, stearic acid, succinic acid, sulfuric acid, L-tartaric acid, vanillic acid, vanillin, ethyl maltol, gallic acid, gallic acid ethyl ester, 4-hydroxybenzoic acid, 4-hydroxybenzoic acid methyl ester, 3,4,5-trihydroxybenzoic acid, nicotinamide, L-proline, and D-sorbitol. In some embodiments, the pharmaceutically acceptable acid is selected from the group consisting of hydrochloric acid, hydrobromic acid, ethanedisulfonic acid, methanesulfonic acid, gentisic acid, benzoic acid, salicylic acid, and gallic acid. In some embodiments, the pharmaceutically acceptable acid is selected from the group consisting of hydrochloric acid, hydrobromic acid, ethanedisulfonic acid, methanesulfonic acid, and gentisic acid. In some embodiments, the pharmaceutically acceptable acid is a benzoic acid derivative. In some embodiments, the pharmaceutically acceptable acid is a benzoic acid derivative substituted with one or more hydroxy groups. In some embodiments, the pharmaceutically acceptable acid is a benzoic acid derivative substituted with one hydroxy group. In some embodiments, the benzoic acid derivative substituted with one hydroxy group is salicylic acid. In some embodiments, the pharmaceutically acceptable acid is a benzoic acid derivative substituted with two hydroxy groups. In some embodiments, the benzoic acid derivative substituted with two hydroxy groups is gentisic acid. In some embodiments, the pharmaceutically acceptable acid is a benzoic acid derivative substituted with three hydroxy groups. In some embodiments, the benzoic acid derivative substituted with three hydroxy groups is gallic acid. In some embodiments, the benzoic acid derivative is selected from the group consisting of salicylic acid, gentisic acid, and gallic acid. In some embodiments, the pharmaceutically acceptable acid is hydrochloric acid. In some embodiments, the pharmaceutically acceptable acid is gentisic acid. In some embodiments, the pharmaceutically acceptable acid is benzoic acid. In some embodiments, the pharmaceutically acceptable acid is salicylic acid. In some embodiments, the pharmaceutically acceptable acid is gallic acid.

In one aspect, the present disclosure relates to a pharmaceutical composition comprising one or more of the solid state forms or mixtures discussed above and one or more pharmaceutically acceptable carriers or diluents.

In another aspect, the present disclosure relates to a solid dosage form comprising one or more of the solid state forms or mixtures discussed above.

In another aspect, the present disclosure relates to a method for treating cancer comprising administering one or more of the solid state forms, mixtures, pharmaceutical compositions, or solid dosage forms discussed above to a patient in need thereof.

In another aspect, the present disclosure relates to a use of one or more of the solid state forms, mixtures, pharmaceutical compositions, or solid dosage forms discussed above for the manufacture of a medicament for treating cancer.

In another aspect, the present disclosure relates to one or more of the solid state forms, mixtures, pharmaceutical compositions, or solid dosage forms discussed above for use in a method for treating cancer.

In another aspect, the present disclosure relates to a method for preparing crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

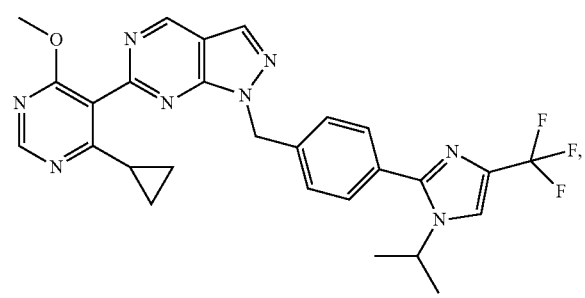

(II)

the method comprising:
  a) dissolving a suitable amount of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine and gentisic acid in a suitable amount of a suitable solvent at room temperature to make a solution;
  b) adding a suitable amount of a suitable anti-solvent;
  c) adding seed crystals of crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II);
  d) stirring the resulting suspension; and
  e) collecting the solid product produced from step d).

In some embodiments, the method for preparing crystalline Form 2 of a gentisic acid co-crystal of a compound of Formula (II) further comprises adding a suitable anti-solvent after step c) and before step d).

In some embodiments, the suitable solvent is ethyl acetate.

In some embodiments, the suitable anti-solvent is n-heptane.

In another aspect, the present disclosure relates to a method for preparing crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II), the method comprising:
  a) adding a suitable amount of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine and gentisic acid to a suitable amount of a suitable solvent system at room temperature to obtain a suspension;
  b) stirring the suspension from step a);
  c) collecting the solid product produced from step b).

In some embodiments, the suitable solvent system is selected from the group consisting of ethyl acetate, n-heptane, and mixtures thereof.

In another aspect, the present disclosure relates to Crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods discussed above.

BRIEF DESCRIPTION OF THE FIGURES

FIG. 1 is a powder X-ray diffraction pattern ("XRPD") corresponding to crystalline Form A.

FIG. 2 is a differential scanning calorimetry thermogram ("DSC") and a thermogravimetric analysis thermogram ("TGA") corresponding to crystalline Form A.

FIG. 3 is an XRPD pattern corresponding to crystalline Form C.

FIG. 4 is an XRPD pattern corresponding to crystalline Form D.

FIG. 5 is an XRPD pattern corresponding to crystalline Form E.

FIG. 6 is a DSC and TGA thermogram corresponding to crystalline Form E.

FIG. 7 is an XRPD pattern corresponding to crystalline Form 1.

FIG. 8 is a DSC and TGA thermogram corresponding to crystalline Form 1.

FIG. 9 is an XRPD pattern corresponding to crystalline Form 2.

FIG. 10 is a DSC and TGA thermogram corresponding to crystalline Form 2.

FIG. 11 is an XRPD pattern corresponding to crystalline Form A1.

FIG. 12 is a DSC and TGA thermogram corresponding to crystalline Form A1.

FIG. 13 is an XRPD pattern corresponding to crystalline Form B1.

FIG. 14 is a DSC and TGA thermogram corresponding to crystalline Form B1.

FIG. 15 is an XRPD pattern corresponding to crystalline Form 3.

FIG. 16 is an XRPD pattern corresponding to crystalline Form 4.

FIG. 17 is an XRPD pattern corresponding to crystalline Form 5.

FIG. 18 is an XRPD pattern corresponding to crystalline Form 6.

FIG. 19 is an XRPD pattern corresponding to crystalline Form 7.

FIG. 20 is an asymmetric unit of crystalline Form A from a single crystal structure.

FIG. 21 is an asymmetric unit of crystalline Form 2 from a single crystal structure.

FIG. 22 is an asymmetric unit of crystalline Form A1 from a single crystal structure.

FIG. 23 is a plasma concentration vs. time profile for crystalline Form A after a 300 mg/kg dose in NOD/SCID mice.

FIG. 24 is a plasma concentration vs. time profile for crystalline Form 2 after a 300 mg/kg dose in NOD/SCID mice.

FIG. 25 is an XRPD pattern corresponding to crystalline Form F.

FIG. 26 is a DSC thermogram corresponding to crystalline Form F.

FIG. 27 is an XRPD pattern corresponding to crystalline Form C.

FIG. 28 is a Raman spectrum corresponding to crystalline Form C.

FIG. 29 is an XRPD pattern corresponding to crystalline Form 8.

FIG. 30 is a DSC thermogram corresponding to crystalline Form 8.

FIG. 31 is a TG-FTIR thermogram corresponding to crystalline Form 8.

FIG. 32 is an asymmetric unit of crystalline Form 8 from a single crystal structure.

FIG. 33 is an XRPD pattern corresponding to crystalline Form 9.

FIG. 34 $^1$H NMR spectrum corresponding to crystalline Form 9.

FIG. 35 is an asymmetric unit of crystalline Form 9 from a single crystal structure.

FIG. 36 is a plasma concentration vs. time profile for crystalline Form 8 after 300 mg/kg dose in NOD/SCID mice.

FIG. 37 is a brain and plasma concentration vs. time profile for crystalline Form 2 after 100 and 300 mg/kg QD repeated oral dose in NOD/SCID female mice.

FIG. 38 is a brain and plasma concentration vs. time profile for crystalline Form 2 after 100 mg/kg oral dose in SD male and female rats.

DETAILED DESCRIPTION OF THE INVENTION

I. Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

The characterizing data for XRPD, DSC, and TGA that is referenced throughout the application and claims are determined using the instruments and conditions specified at the beginning of the Examples section under the subheading "Instrumental Conditions."

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "Compound of Formula (I)" refers to a compound encompassed within the structure below:

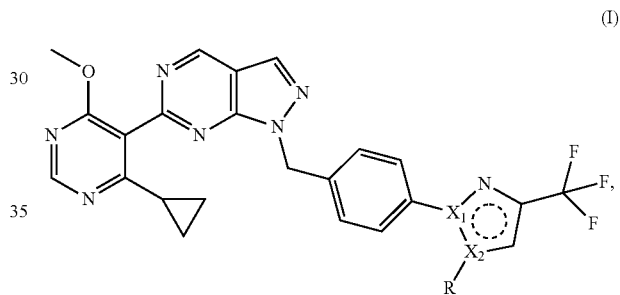

(I)

or a pharmaceutically acceptable salt thereof, wherein R is $C_{1-3}$ alkyl; and $X_1$ and $X_2$ are independently selected from the group consisting of N and C.

In some embodiments, R can be selected from methyl, ethyl, n-propyl, isopropyl, and cyclopropyl.

The term "Compound of Formula (II)" refers to 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine having the structure below:

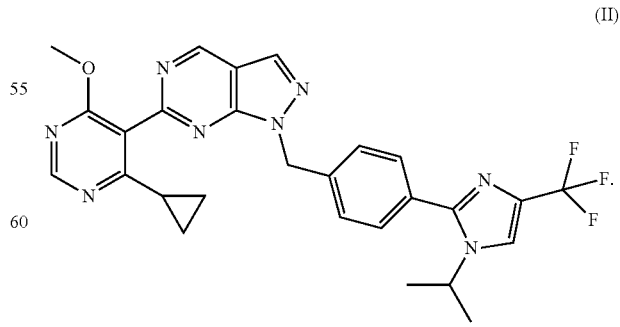

(II)

The term "Compound of Formula (III)" refers to 6-(4-cyclopropyl-6-methoxypyrimidin-5-yl)-1-(4-(5-methyl-3-

(trifluoromethyl)-1H-pyrazol-1-yl)benzyl)-1H-pyrazolo[3,4-d]pyrimidine having the structure below:

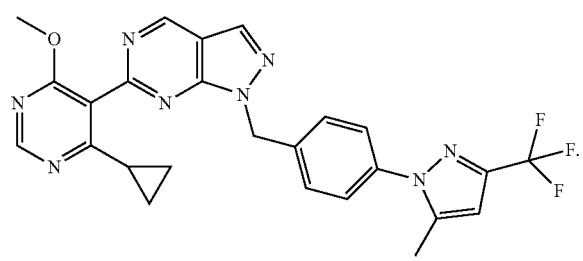

(III)

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include approaches for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In the context of cancer, the terms "treat," "treating," and "treatment" include, but are not limited to, inhibiting growth of cancer cells, inhibiting replication of cancer cells, lessening of overall tumor burden, and delaying, halting, or slowing tumor growth, progression, or metastasis.

As used herein, the terms "cancer" and "tumor" refer to or describe the physiological condition in mammals in which a population of cells are characterized by unregulated cell growth. The terms encompass solid and hematological/lymphatic cancers. Examples of cancer include but are not limited to, DNA repair pathway deficient cancers and homologous recombination deficiency (HRD) cancers. Additional examples of cancer include, but are not limited to, ovarian cancer, breast cancer (including triple negative breast cancer), non-small cell lung cancer (NSCLC), and osteosarcoma. The cancer can be BRCA1 and/or BRCA2 wildtype. The cancer can also be BRCA1 and/or BRCA2 mutant. The cancer can further be a PARP inhibitor refractory or resistant cancer, or a PARP inhibitor refractory or resistant BRCA1 or BRCA2-mutant cancer.

The term "disease" or "condition" or "disorder" as used herein refers to a condition where treatment is needed and/or desired and denotes disturbances and/or anomalies that as a rule are regarded as being pathological conditions or functions, and that can manifest themselves in the form of particular signs, symptoms, and/or malfunctions. As demonstrated below, Compounds of the Disclosure can be used in treating diseases and conditions such as proliferative diseases like cancer.

A "therapeutically effective amount" of a substance can vary according to factors such as the disease state, age, sex, and weight of the individual, and the ability of the substance to elicit a desired response in the individual. A therapeutically effective amount is also one in which any toxic or detrimental effects of the substance are outweighed by the therapeutically beneficial effects. A therapeutically effective amount can be delivered in one or more administrations. A therapeutically effective amount refers to an amount effective, at dosages and for periods of time necessary, to achieve the desired therapeutic effect.

The terms "administer," "administering," "administration," and the like refer to methods that can be used to enable delivery of the therapeutic agent to the desired site of biological action. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. A pharmaceutically acceptable carrier is non-toxic to recipients at the dosages and concentrations employed and is compatible with other ingredients of the formulation. The pharmaceutically acceptable carrier is appropriate for the formulation employed. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; Pharmaceutical Preformulation and Formulation, Gibson Ed., CRC Press LLC: Boca Raton, Fla., 2004 (incorporated herein by reference).

The term "about," as used herein, includes the recited number ±10%. Thus, "about 10" means 9 to 11. As is understood by one skilled in the art, reference to "about" a value or parameter herein includes (and describes) instances that are directed to that value or parameter per se. For example, description referring to "about X" includes description of "X."

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "solvate" refers to a compound provided herein or a salt thereof, which further includes a stoichiometric or non-stoichiometric amount of solvent bound by non-covalent intermolecular forces. Where the solvent is water, the solvate is a hydrate. Where the solvent includes ethanol, the compound can be an ethanol solvate.

The term "polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, co-crystal, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences*, 18th ed., Mack Publishing, Easton Pa., 173 (1990); *The United States Pharmacopeia*, 23$^{rd}$ ed., 1843-1844 (1995) (incorporated herein by reference).

Crystalline forms are most commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. A skilled artisan understanding these variations is capable of discriminating or ascertaining the defining features or characteristics of a particular crystal form using) (RFD, as well as using other known physicochemical techniques.

The term "amorphous" as applied to a compound refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition").

The term "anhydrate" as applied to a compound refers to a solid state wherein the compound contains no structural water within the crystal lattice.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Solid State Forms

The present disclosure relates to solid state forms of a compound of Formula (I), a compound of Formula (II), and a compound of Formula (III). As with all pharmaceutical compounds and compositions, the chemical and physical properties of the compound of Formula (I), the compound of Formula (II), and the compound of Formula (III) are important in their commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, the processing and storage of the compounds and pharmaceutical compositions comprising the compounds.

Solid state forms of the compound of Formula (I), the compound of Formula (II), and the compound of Formula (III) that improve upon one or more of these properties relative to other solid state forms of the compounds are desirable. Isolating pharmaceutically acceptable solid state forms of the compounds that can be manufactured and formulated on a commercial-scale has been a challenge.

A. Compound of Formula (II)

In one aspect, the present disclosure relates to a solid state form of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

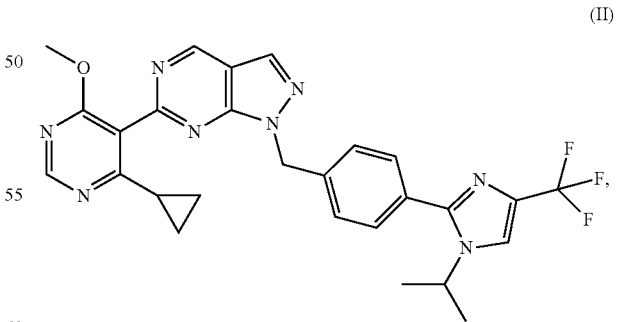

or a pharmaceutically acceptable salt thereof.

In some embodiments, the solid state form is an amorphous form of a compound of Formula (II). In some embodiments, the amorphous form is a hydrate, anhydrate, or solvate thereof. In some embodiments, the amorphous form is substantially free of other polymorphic forms.

In some embodiments, the present disclosure relates to a mixture comprising a majority of the amorphous form as compared to other solid state forms of a compound of Formula (II). In some embodiments, the amorphous form has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In some embodiments, the solid state form is a crystalline form of a compound of Formula (II). In some embodiments, the crystalline form is a hydrate, anhydrate, or solvate thereof. In some embodiments, the solvate is a dichloromethane solvate.

In some embodiments, the solid state form of a compound of Formula (II) is selected from the group consisting of:
a) crystalline Form A, wherein Form A is characterized by an XRPD pattern having peaks at 14.3±0.2, 21.5±0.2, and 21.8±0.2 degrees two theta;
b) crystalline Form C, wherein Form C is characterized by an XRPD pattern having peaks at 14.2±0.2, 17.0±0.2, and 19.1±0.2 degrees two theta;
c) crystalline Form D, wherein Form D is characterized by an XRPD pattern having peaks at 13.9±0.2, 15.2±0.2, and 19.3±0.2 degrees two theta;
d) crystalline Form E, wherein Form E is characterized by an XRPD pattern having peaks at 10.6±0.2, 18.7±0.2, and 20.9±0.2 degrees two theta; and
(e) crystalline Form F, wherein Form F is characterized by an XRPD pattern having peaks at 10.7±0.2, 14.3±0.2, and 21.8±0.2 degrees two theta.

In some embodiments, the solid state form of a compound of Formula (II) is selected from the group consisting of:
a) crystalline Form A, wherein Form A is characterized by an XRPD pattern having peaks at 14.3±0.2, 21.5±0.2, and 21.8±0.2 degrees two theta;
b) crystalline Form C, wherein Form C is characterized by an XRPD pattern having peaks at 14.2±0.2, 17.0±0.2, and 19.1±0.2 degrees two theta;
c) crystalline Form D, wherein Form D is characterized by an XRPD pattern having peaks at 13.9±0.2, 15.2±0.2, and 19.3±0.2 degrees two theta; and
d) crystalline Form E, wherein Form E is characterized by an XRPD pattern having peaks at 10.6±0.2, 18.7±0.2, and 20.9±0.2 degrees two theta.

In some embodiments, the solid state form is a pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II). In some embodiments, the pharmaceutically acceptable salt is formed between 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and a pharmaceutically acceptable acid.

In some embodiments, the pharmaceutically acceptable acid is selected from the group consisting of 1-hydroxy-2-naphthoic acid, 4-aminosalicylic acid, ascorbic acid, adipic acid, L-aspartic acid, benzene sulfonic acid, benzoic acid, trans-cinnamic acid, citric acid, ethanedisulfonic acid, fumaric acid, galactaric acid, gentisic acid, gluconic acid, D-glucuronic acid, glutamic acid, glutaric acid, glycolic acid, hexanoic acid, hippuric acid, hydrobromic acid, hydrochloric acid, lactic acid, maleic acid, L-malic acid, malonic acid, R-mandelic acid, methanesulfonic acid, mucic acid, naphthalene sulfonic acid, nicotinic acid, oxalic acid, palmitic acid, p-toluene sulfonic acid, phosphoric acid, propionic acid, saccharin, salicylic acid, stearic acid, succinic acid, sulfuric acid, L-tartaric acid, vanillic acid, vanillin, ethyl maltol, gallic acid, gallic acid ethyl ester, 4-hydroxybenzoic acid, 4-hydroxybenzoic acid methyl ester, 3,4,5-trihydroxybenzoic acid, nicotinamide, L-proline, and D-sorbitol. In some embodiments, the pharmaceutically acceptable acid is selected from the group consisting of hydrochloric acid, hydrobromic acid, ethanedisulfonic acid, methanesulfonic acid, gentisic acid, benzoic acid, salicylic acid, and gallic acid. In some embodiments, the pharmaceutically acceptable acid is selected from the group consisting of hydrochloric acid, hydrobromic acid, ethanedisulfonic acid, methanesulfonic acid, and gentisic acid. In some embodiments, the pharmaceutically acceptable acid is a benzoic acid derivative. In some embodiments, the pharmaceutically acceptable acid is a benzoic acid derivative substituted with one or more hydroxy groups. In some embodiments, the pharmaceutically acceptable acid is a benzoic acid derivative substituted with one hydroxy group. In some embodiments, the benzoic acid derivative substituted with one hydroxy group is salicylic acid. In some embodiments, the pharmaceutically acceptable acid is a benzoic acid derivative substituted with two hydroxy groups. In some embodiments, the benzoic acid derivative substituted with two hydroxy groups is gentisic acid. In some embodiments, the pharmaceutically acceptable acid is a benzoic acid derivative substituted with three hydroxy groups. In some embodiments, the benzoic acid derivative substituted with three hydroxy groups is gallic acid. In some embodiments, the benzoic acid derivative is selected from the group consisting of salicylic acid, gentisic acid, and gallic acid. In some embodiments, the pharmaceutically acceptable acid is hydrochloric acid. In some embodiments, the pharmaceutically acceptable acid is hydrobromic acid. In some embodiments, the pharmaceutically acceptable acid is ethanedisulfonic acid. In some embodiments, the pharmaceutically acceptable acid is methanesulfonic acid. In some embodiments, the pharmaceutically acceptable acid is gentisic acid. In some embodiments, the pharmaceutically acceptable acid is benzoic acid. In some embodiments, the pharmaceutically acceptable acid is salicylic acid. In some embodiments, the pharmaceutically acceptable acid is gallic acid.

In some embodiments, the pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is an amorphous form. In some embodiments, the amorphous form is substantially free of other polymorphic forms. In some embodiments, the amorphous form has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In some embodiments, the pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a crystalline form.

In some embodiments, the pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a hydrate, anhydrate, or solvate thereof.

In some embodiments, the pharmaceutically acceptable salt of 6-(4-cyclopropyl-6-methoxypyrimidin-5-yl)-1-(4-(1- isopropyl-4-(trifluoromethyl)-1H-imidazol-2-yl)benzyl)-1H-pyrazolo[3,4-d]pyrimidine of Formula (II) is a hydrochloric acid salt. In some embodiments, the hydrochloric acid salt is crystalline Form 1 characterized by an XRPD pattern having peaks at 12.5±0.2, 22.4±0.2, and 23.9±0.2 degrees two theta. In some embodiments, the hydrochloric acid salt is crystalline Form 1 characterized by an XRPD pattern as shown in FIG. 7.

In some embodiments, the hydrochloric acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is crystalline Form 3 characterized by an XRPD pattern as shown in FIG. 15.

In some embodiments, the pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a hydrobromic acid salt. In some embodiments, the hydrobromic acid salt is crystalline Form 4 characterized by an XRPD pattern as shown in FIG. 16.

In some embodiments, the hydrobromic acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is crystalline Form 5 characterized by an XRPD pattern as shown in FIG. 17.

In some embodiments, the pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is an ethanedisulfonic acid salt. In some embodiments, the ethanedisulfonic acid salt is crystalline Form 6 characterized by an XRPD pattern as shown in FIG. 18.

In some embodiments, the pharmaceutically acceptable salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a methanesulfonic acid salt. In some embodiments, the methanesulfonic acid salt is crystalline Form 7 characterized by an XRPD pattern as shown in FIG. 19.

In some embodiments, the solid state form is a pharmaceutically acceptable co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and a second pharmaceutically acceptable compound. In some embodiments, the second pharmaceutically acceptable compound is a pharmaceutically acceptable acid. In some embodiments, the pharmaceutically acceptable co-crystal is formed between 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and a pharmaceutically acceptable acid.

In some embodiments, the pharmaceutically acceptable acid is selected from the group consisting of 1-hydroxy-2-naphthoic acid, 4-aminosalicylic acid, ascorbic acid, adipic acid, L-aspartic acid, benzene sulfonic acid, benzoic acid, trans-cinnamic acid, citric acid, ethanedisulfonic acid, fumaric acid, galactaric acid, gentisic acid, gluconic acid, D-glucuronic acid, glutamic acid, glutaric acid, glycolic acid, hexanoic acid, hippuric acid, hydrobromic acid, hydrochloric acid, lactic acid, maleic acid, L-malic acid, malonic acid, R-mandelic acid, methanesulfonic acid, mucic acid, naphthalene sulfonic acid, nicotinic acid, oxalic acid, palmitic acid, p-toluene sulfonic acid, phosphoric acid, propionic acid, saccharin, salicylic acid, stearic acid, succinic acid, sulfuric acid, L-tartaric acid, vanillic acid, vanillin, ethyl maltol, gallic acid, gallic acid ethyl ester, 4-hydroxybenzoic acid, 4-hydroxybenzoic acid methyl ester, 3,4,5-trihydroxybenzoic acid, nicotinamide, L-proline, and D-sorbitol. In some embodiments, the pharmaceutically acceptable acid is selected from the group consisting of hydrochloric acid, hydrobromic acid, ethanedisulfonic acid, methanesulfonic acid, gentisic acid, benzoic acid, salicylic acid, and gallic acid. In some embodiments, the pharmaceutically acceptable acid is selected from the group consisting of hydrochloric acid, hydrobromic acid, ethanedisulfonic acid, methanesulfonic acid, and gentisic acid. In some embodiments, the pharmaceutically acceptable acid is a benzoic acid derivative. In some embodiments, the pharmaceutically acceptable acid is a benzoic acid derivative substituted with one or more hydroxy groups. In some embodiments, the pharmaceutically acceptable acid is a benzoic acid derivative substituted with one hydroxy group. In some embodiments, the benzoic acid derivative substituted with one hydroxy group is salicylic acid. In some embodiments, the pharmaceutically acceptable acid is a benzoic acid derivative substituted with two hydroxy groups. In some embodiments, the benzoic acid derivative substituted with two hydroxy groups is gentisic acid. In some embodiments, the pharmaceutically acceptable acid is a benzoic acid derivative substituted with three hydroxy groups. In some embodiments, the benzoic acid derivative substituted with three hydroxy groups is gallic acid. In some embodiments, the benzoic acid derivative is selected from the group consisting of salicylic acid, gentisic acid, and gallic acid. In some embodiments, the pharmaceutically acceptable acid is hydrochloric acid. In some embodiments, the pharmaceutically acceptable acid is hydrobromic acid. In some embodiments, the pharmaceutically acceptable acid is ethanedisulfonic acid. In some embodiments, the pharmaceutically acceptable acid is methanesulfonic acid. In some embodiments, the pharmaceutically acceptable acid is gentisic acid. In some embodiments the, the pharmaceutically acceptable acid is benzoic acid. In some embodiments, the pharmaceutically acceptable acid is salicylic acid. In some embodiments, the pharmaceutically acceptable acid is gallic acid.

In some embodiments, the pharmaceutically acceptable co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a hydrate, anhydrate, or solvate thereof.

In some embodiments, the pharmaceutically acceptable co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a gentisic acid co-crystal. In some embodiments, the gentisic acid co-crystal is crystalline Form 2 characterized by an XRPD pattern having peaks at 16.6±0.2, 18.7±0.2, and 22.5±0.2 degrees two theta.

In some embodiments, the pharmaceutically acceptable co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a benzoic acid co-crystal. In some embodiments, the benzoic acid co-crystal is crystalline Form 8 characterized by an XRPD pattern having peaks at 12.1±0.2, 14.2±0.2, and 16.5±0.2 degrees two theta.

In some embodiments, the pharmaceutically acceptable co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) is a salicylic acid co-crystal. In some embodiments, the salicylic acid co-crystal is crystalline Form 9 characterized by an XRPD pattern substantially as shown in FIG. 33.

The sections below discuss solid state forms of a compound of Formula (II) that have been identified and selected properties of those solid state forms.

1. Crystalline Form A

In one aspect, the present disclosure relates to crystalline Form A of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

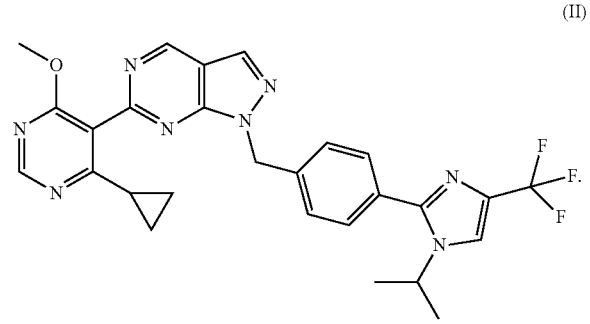 [SMILES: COc1ncnc(C2CC2)c1-c1ncc2cnn(Cc3ccc(-c4nc(C(F)(F)F)cn4C(C)C)cc3)c2n1]

(II)

In some embodiments, crystalline Form A is a 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine hydrate.

In some embodiments, the melting point of crystalline Form A is about 165° C.

In some embodiments, crystalline Form A is characterized by an XRPD pattern having peaks at 14.3±0.2, 21.5±0.2, and 21.8±0.2 degrees two theta when measured by Cu Kα radiation. In another embodiment, crystalline Form A is characterized by an XRPD pattern having peaks at 7.1±0.2, 14.3±0.2, 21.5±0.2, and 21.8±0.2 degrees two theta when measured by Cu Kα radiation. In another embodiment, crystalline Form A is characterized by an XRPD pattern having peaks at 7.1±0.2, 14.3±0.2, 19.1±0.2, 21.5±0.2, and 21.8±0.2 degrees two theta when measured by Cu Kα radiation. In another embodiment, crystalline Form A is characterized by an XRPD pattern having peaks at 7.1±0.2, 14.3±0.2, 15.2±0.2, 19.1±0.2, 21.5±0.2, and 21.8±0.2 degrees two theta when measured by Cu Kα radiation.

In some embodiments, crystalline Form A is characterized by an XRPD pattern substantially as shown in FIG. 1.

In some embodiments, crystalline Form A is characterized by three or more, four or more, five or more, or six or more XRPD peaks listed in Table 1 below.

TABLE 1a

Selected XRPD Peaks for Crystalline Form A

| Pos. [°2Th.] | d-spacing [Å] | Rel. Int. [%] |
|---|---|---|
| 7.14 | 12.39 | 4.09 |
| 14.29 | 6.20 | 100.00 |
| 15.20 | 5.83 | 5.85 |
| 17.08 | 5.19 | 5.08 |
| 19.13 | 4.64 | 7.52 |
| 21.49 | 4.13 | 26.71 |
| 21.80 | 4.08 | 20.57 |

TABLE 1b

XRPD Peaks for Crystalline Form A

| Pos. [°2Th.] | d-spacing [Å] | Rel. Int. [%] |
|---|---|---|
| 7.14 | 12.39 | 4.09 |
| 10.64 | 8.32 | 1.01 |
| 14.29 | 6.20 | 100.00 |
| 15.20 | 5.83 | 5.85 |
| 15.80 | 5.61 | 3.61 |
| 17.08 | 5.19 | 5.08 |
| 17.74 | 5.00 | 0.83 |
| 19.13 | 4.64 | 7.52 |
| 19.84 | 4.48 | 2.39 |
| 21.49 | 4.13 | 26.71 |
| 21.80 | 4.08 | 20.57 |
| 23.78 | 3.74 | 1.78 |
| 24.47 | 3.64 | 3.29 |
| 25.00 | 3.56 | 1.42 |
| 28.82 | 3.10 | 1.11 |

In some embodiments, crystalline Form A is characterized by an endothermic peak at from about 162° C. to about 168° C., or from about 163° C. to about 167° C., or from about 164° C. to about 166° C., as determined by DSC. In some embodiments, crystalline Form A is characterized by an endothermic peak at about 165° C., as determined by DSC.

In some embodiments, crystalline Form A is characterized by a DSC profile substantially as shown in FIG. 2.

In some embodiments, crystalline Form A is characterized by from an about 0.88 wt % to an about 0.98 wt % loss between room temperature and about 150° C. In some embodiments, crystalline Form A is characterized by from an about 0.90 wt % to an about 0.96 wt % loss between room temperature and about 150° C. In some embodiments, crystalline Form A is characterized by from an about 0.93 wt % loss between room temperature and about 150° C.

In some embodiments, crystalline Form A is characterized by a TGA profile substantially as shown in FIG. 2.

In some embodiments, crystalline Form A is characterized by at least two of the following: a) an XRPD pattern as shown in FIG. 1; b) a DSC profile as shown in FIG. 2; or c) a TGA profile as shown in FIG. 2.

In some embodiments, crystalline Form A has a unit cell that indexes as monoclinic.

In some embodiments, crystalline Form A has a unit cell with an a value of about 12.054 Å, a b value of about 8.775 Å, and a c value of about 24.837 Å. In other embodiments, Form A has a unit cell with a volume of about 2603.68 Å$^3$.

In some embodiments, crystalline Form A is substantially free of other polymorphic forms. In some embodiments, crystalline Form A has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%. In some embodiments, crystalline Form A has a polymorphic purity of at least 80%.

In another aspect, the present disclosure relates to a mixture comprising crystalline Form A and a second solid state form of a compound of Formula (II). In some embodiments, the second solid state form of a compound of Formula (II) is crystalline Form C, or crystalline Form D, or crystalline Form E, or crystalline Form F, or crystalline Form 1, or crystalline Form 2, or crystalline Form 8, or crystalline Form 9. In some embodiments, the second solid state form of a compound of Formula (II) is crystalline Form C, or crystalline Form D, or crystalline Form F, or crystalline Form 1, or crystalline Form 2.

In some embodiments, the present disclosure relates to a mixture comprising a majority of crystalline Form A as compared to other solid state forms of a compound of Formula (II).

2. Crystalline Form C

In one aspect, the present disclosure relates to crystalline Form C of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

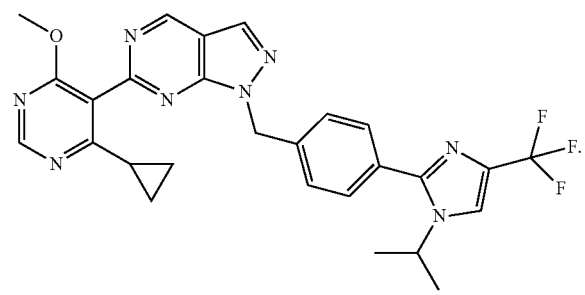

(II)

In some embodiments, crystalline Form C is an anhydrate.

In some embodiments, crystalline Form C is characterized by an XRPD pattern having peaks at 14.2±0.2, 17.0±0.2, and 19.1±0.2 degrees two theta when measured by Cu Kα radiation. In another embodiment, crystalline Form C is characterized by an XRPD pattern having peaks at 14.2±0.2, 17.0±0.2, 19.1±0.2, and 21.5±0.2 degrees two theta when measured by Cu Kα radiation. In another embodiment, crystalline Form C is characterized by an XRPD pattern having peaks at 14.2±0.2, 17.0±0.2, 19.1±0.2, 19.8±0.2, and 21.5±0.2 degrees two theta when measured by Cu Kα radiation. In another embodiment, crystalline Form C is characterized by an XRPD pattern having peaks at 14.2±0.2, 17.0±0.2, 19.1±0.2, 19.8±0.2, 21.5±0.2, and 21.8±0.2 degrees two theta when measured by Cu Kα radiation.

In some embodiments, crystalline Form C is characterized by an XRPD pattern substantially as shown in FIG. 3.

In some embodiments, crystalline Form C is characterized by three or more, four or more, five or more, or six or more XRPD peaks listed in Table 2 below.

TABLE 2a

Select XRPD Peaks for Crystalline Form C

| Pos. [°2Th.] | d-spacing [Å] | Rel. Int. [%] |
|---|---|---|
| 13.81 | 6.41 | 4.35 |
| 14.23 | 6.22 | 100.00 |
| 14.66 | 6.04 | 4.35 |
| 15.16 | 5.85 | 10.66 |
| 15.76 | 5.62 | 9.01 |
| 16.98 | 5.22 | 13.50 |
| 17.67 | 5.02 | 4.06 |
| 19.06 | 4.66 | 15.28 |
| 19.76 | 4.49 | 10.52 |
| 21.02 | 4.23 | 4.39 |
| 21.45 | 4.14 | 32.88 |
| 21.67 | 4.10 | 21.20 |
| 21.78 | 4.08 | 24.52 |
| 23.75 | 3.75 | 4.77 |
| 24.42 | 3.65 | 5.72 |
| 24.94 | 3.57 | 6.06 |

TABLE 2b

XRPD Peaks for Crystalline Form C

| Pos. [°2Th.] | d-spacing [Å] | Rel. Int. [%] |
|---|---|---|
| 7.08 | 12.49 | 2.69 |
| 10.62 | 8.33 | 3.56 |
| 12.37 | 7.16 | 1.58 |
| 13.12 | 6.75 | 2.06 |
| 13.81 | 6.41 | 4.35 |
| 14.23 | 6.22 | 100.00 |
| 14.66 | 6.04 | 4.35 |
| 15.16 | 5.85 | 10.66 |
| 15.34 | 5.78 | 2.88 |
| 15.76 | 5.62 | 9.01 |
| 16.70 | 5.22 | 13.50 |
| 17.67 | 5.02 | 4.06 |
| 18.21 | 4.87 | 3.14 |
| 19.06 | 4.66 | 15.28 |
| 19.76 | 4.49 | 10.52 |
| 20.53 | 4.33 | 2.48 |
| 21.02 | 4.23 | 4.39 |
| 21.45 | 4.14 | 32.88 |
| 21.67 | 4.10 | 21.20 |
| 21.78 | 4.08 | 24.52 |
| 22.89 | 3.89 | 1.96 |
| 23.75 | 3.75 | 4.77 |
| 24.42 | 3.65 | 5.72 |
| 24.62 | 3.62 | 3.59 |
| 24.94 | 3.57 | 6.06 |
| 25.40 | 3.51 | 1.50 |
| 25.97 | 3.43 | 2.00 |
| 26.45 | 3.37 | 4.00 |
| 27.54 | 3.24 | 1.77 |
| 28.80 | 3.10 | 2.79 |
| 29.31 | 3.05 | 1.84 |
| 29.84 | 2.99 | 1.17 |
| 30.66 | 2.92 | 1.57 |
| 32.39 | 2.77 | 1.12 |
| 34.00 | 2.64 | 0.94 |
| 35.63 | 2.52 | 0.60 |
| 38.52 | 2.34 | 0.42 |

In some embodiments, crystalline Form C is substantially free of other polymorphic forms. In some embodiments, crystalline Form C has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form C and a second solid state form of a compound of Formula (II). In some embodiments, the second solid state form of a compound of Formula (II) is crystalline Form A, or crystalline Form D, or crystalline Form E, or crystalline Form F, or crystalline Form 1, or crystalline Form 2, or crystalline Form 8, or crystalline Form 9. In some embodiments, the second solid state form of a compound of Formula (II) is crystalline Form A, or crystalline Form D, or crystalline Form E, or crystalline Form 1, or crystalline Form 2.

In some embodiments, the present disclosure relates to a mixture comprising a majority of crystalline Form C as compared to other solid state forms of a compound of Formula (II).

3. Crystalline Form D

In one aspect, the present disclosure relates to crystalline Form D of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

(II)

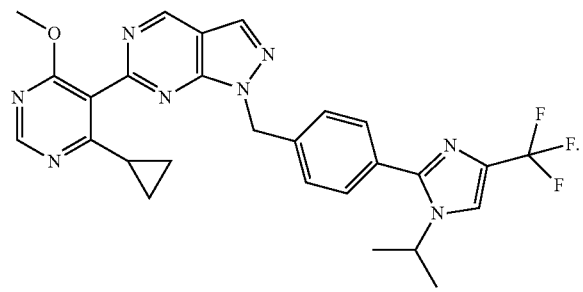

In some embodiments, crystalline Form D is an anhydrate.

In some embodiments, crystalline Form D is characterized by an XRPD pattern having peaks at 13.9±0.2, 15.2±0.2, and 19.3±0.2 degrees two theta when measured by Cu Kα radiation. In another embodiment, crystalline Form D is characterized by an XRPD pattern having peaks at 13.9±0.2, 15.2±0.2, 16.4±0.2, and 19.3±0.2 degrees two theta when measured by Cu Kα radiation. In another embodiment, crystalline Form D is characterized by an XRPD pattern having peaks at 13.9±0.2, 15.2±0.2, 16.4±0.2, 19.3±0.2, and 20.9±0.2 degrees two theta when measured by Cu Kα radiation. In another embodiment, crystalline Form D is characterized by an XRPD pattern having peaks at 13.9±0.2, 15.2±0.2, 16.4±0.2, 19.3±0.2, 20.9±0.2, and 21.6±0.2 degrees two theta when measured by Cu Kα radiation.

In some embodiments, crystalline Form D is characterized by an XRPD pattern substantially as shown in FIG. 4.

In some embodiments, crystalline Form D is characterized by three or more, four or more, five or more, or six or more XRPD peaks listed in Table 2 below.

TABLE 3a

Select XRPD Peaks for Crystalline Form D

| Pos. [°2Th.] | d-spacing [Å] | Rel. Int. [%] |
|---|---|---|
| 6.91 | 12.80 | 6.57 |
| 12.20 | 7.25 | 4.64 |
| 13.88 | 6.38 | 100.00 |
| 14.38 | 6.16 | 4.57 |
| 15.19 | 5.83 | 22.20 |
| 15.84 | 5.59 | 7.07 |
| 16.07 | 5.52 | 5.88 |
| 16.38 | 5.41 | 17.20 |
| 18.25 | 4.86 | 8.93 |
| 19.32 | 4.60 | 23.69 |
| 20.71 | 4.29 | 15.59 |
| 20.90 | 4.25 | 19.49 |
| 21.35 | 4.16 | 4.03 |
| 21.64 | 4.11 | 27.64 |
| 22.59 | 3.94 | 5.07 |
| 23.24 | 3.83 | 10.00 |
| 24.95 | 3.57 | 4.33 |

TABLE 3b

XRPD Peaks for Crystalline Form D

| Pos. [°2Th.] | d-spacing [Å] | Rel. Int. [%] |
|---|---|---|
| 6.91 | 12.80 | 6.57 |
| 9.58 | 9.23 | 0.69 |
| 10.62 | 8.33 | 2.07 |
| 12.20 | 7.25 | 4.64 |
| 12.35 | 7.17 | 2.45 |
| 13.88 | 6.38 | 100.00 |
| 14.38 | 6.16 | 4.57 |
| 15.19 | 5.83 | 22.20 |
| 15.84 | 5.59 | 7.07 |
| 16.07 | 5.52 | 5.88 |
| 16.38 | 5.41 | 17.20 |
| 17.16 | 5.17 | 2.19 |
| 17.70 | 5.01 | 3.49 |
| 18.25 | 4.86 | 8.93 |
| 19.32 | 4.60 | 23.69 |
| 20.71 | 4.29 | 15.59 |
| 20.90 | 4.25 | 19.49 |
| 21.35 | 4.16 | 4.03 |
| 21.64 | 4.11 | 27.64 |
| 22.59 | 3.94 | 5.07 |
| 23.24 | 3.83 | 10.00 |
| 24.10 | 3.69 | 2.88 |
| 24.61 | 3.62 | 3.99 |
| 24.95 | 3.57 | 4.33 |
| 25.24 | 3.53 | 3.09 |
| 25.56 | 3.49 | 3.39 |
| 26.62 | 3.35 | 2.47 |
| 27.02 | 3.30 | 2.00 |
| 28.48 | 3.13 | 1.42 |
| 28.93 | 3.09 | 1.02 |
| 29.45 | 3.03 | 1.23 |
| 30.26 | 2.95 | 1.13 |
| 30.70 | 2.91 | 0.81 |
| 32.27 | 2.77 | 0.35 |
| 35.46 | 2.53 | 0.24 |

In some embodiments, crystalline Form D is substantially free of other polymorphic forms. In some embodiments, crystalline Form D has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form D and a second solid state form of a compound of Formula (II). In some embodiments, the second solid state form of a compound of Formula (II) is crystalline Form A, or crystalline Form C, or crystalline Form E, or crystalline Form F, or crystalline Form 1, or crystalline Form 2, or crystalline Form 8, or crystalline Form 9. In some embodiments, the second solid state form of a compound of Formula (II) is crystalline Form A, or crystalline Form C, or crystalline Form E, or crystalline Form 1, or crystalline Form 2.

In some embodiments, the present disclosure relates to a mixture comprising a majority of crystalline Form D as compared to other solid state forms of a compound of Formula (II).

4. Crystalline Form E

In one aspect, the present disclosure relates to crystalline Form E of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

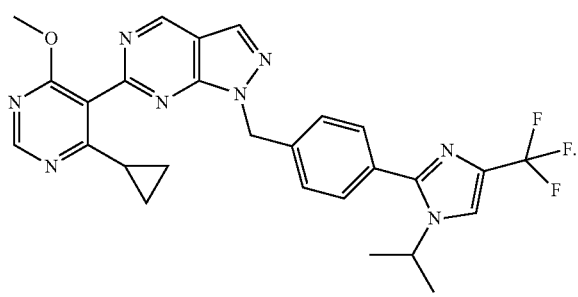

(II)

In some embodiments, crystalline Form E is a solvate. In some embodiments, crystalline Form E is a dichloromethane solvate.

In some embodiments, the melting point of crystalline Form E is about 107° C.

In some embodiments, crystalline Form E is characterized by an XRPD pattern having peaks at 10.6±0.2, 18.7±0.2, and 20.9±0.2 degrees two theta when measured by Cu Kα radiation. In another embodiment, crystalline Form E is characterized by an XRPD pattern having peaks at 10.6±0.2, 18.7±0.2, 20.9±0.2, and 21.2±0.2 degrees two theta when measured by Cu Kα radiation. In another embodiment, crystalline Form E is characterized by an XRPD pattern having peaks at 10.6±0.2, 16.4±0.2, 18.7±0.2, 20.9±0.2, and 21.2±0.2 degrees two theta when measured by Cu Kα radiation. In another embodiment, crystalline Form E is characterized by an XRPD pattern having peaks at 10.6±0.2, 16.4±0.2, 18.7±0.2, 20.9±0.2, 21.2±0.2, and 23.9±0.2 degrees two theta when measured by Cu Kα radiation.

In some embodiments, crystalline Form E is characterized by an XRPD pattern substantially as shown in FIG. 5.

In some embodiments, crystalline Form E is characterized by three or more, four or more, five or more, or six or more XRPD peaks listed in Table 4 below.

TABLE 4

XRPD Peaks for Crystalline Form E

| Pos. [°2Th.] | d-spacing [Å] | Rel. Int. [%] |
|---|---|---|
| 5.33 | 16.58 | 20.28 |
| 9.42 | 9.39 | 15.99 |
| 10.60 | 8.34 | 64.75 |
| 12.49 | 7.09 | 26.42 |
| 13.49 | 6.57 | 35.86 |
| 13.93 | 6.36 | 30.40 |
| 14.34 | 6.18 | 47.06 |
| 15.42 | 5.75 | 9.76 |
| 16.38 | 5.41 | 47.43 |
| 18.75 | 4.73 | 50.46 |
| 19.48 | 4.56 | 16.14 |
| 20.68 | 4.30 | 44.67 |
| 20.92 | 4.25 | 65.86 |
| 21.22 | 4.19 | 100.00 |
| 22.05 | 4.03 | 10.01 |
| 22.80 | 3.90 | 12.60 |
| 23.48 | 3.79 | 27.14 |
| 23.88 | 3.73 | 40.90 |
| 24.50 | 3.63 | 23.90 |
| 25.19 | 3.53 | 21.50 |
| 26.66 | 3.34 | 30.19 |
| 27.12 | 3.29 | 15.91 |
| 28.42 | 3.14 | 13.00 |
| 32.28 | 2.77 | 4.56 |

In some embodiments, crystalline Form E is characterized by an endothermic peak at from about 102° C. to about 112° C., or from about 104° C. to about 110° C., or from about 106° C. to about 108° C., as determined by DSC. In some embodiments, crystalline Form E is characterized by an endothermic peak at about 107° C., as determined by DSC.

In some embodiments, crystalline Form E is characterized by a DSC profile substantially as shown in FIG. 6.

In some embodiments, crystalline Form E is characterized by from an about 13.0 wt % to an about 14.0 wt % loss between room temperature and about 200° C. In some embodiments, crystalline Form E is characterized by from an about 13.2 wt % to an about 13.8 wt % loss between room temperature and about 200° C. In some embodiments, crystalline Form E is characterized by from an about 13.5 wt % loss between room temperature and about 200° C.

In some embodiments, crystalline Form E is characterized by a TGA profile substantially as shown in FIG. 6.

In some embodiments, crystalline Form E is characterized by at least two of the following: a) an XRPD pattern as shown in FIG. 5; b) a DSC profile as shown in FIG. 6; or c) a TGA profile as shown in FIG. 6.

In some embodiments, crystalline Form E is substantially free of other polymorphic forms. In some embodiments, crystalline Form E has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form E and a second solid state form of a compound of Formula (II). In some embodiments, the second solid state form of a compound of Formula (II) is crystalline Form A, or crystalline Form C, or crystalline Form D, or crystalline Form F, or crystalline Form 1, or crystalline Form 2, or crystalline Form 8, or crystalline Form 9. In some embodiments, the second solid state form of a compound of Formula (II) is crystalline Form A, or crystalline Form C, or crystalline Form D, or crystalline Form 1, or crystalline Form 2.

In some embodiments, the present disclosure relates to a mixture comprising a majority of crystalline Form E as compared to other solid state forms of a compound of Formula (II).

5. Crystalline Form F

In one aspect, the present disclosure relates to crystalline Form F of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

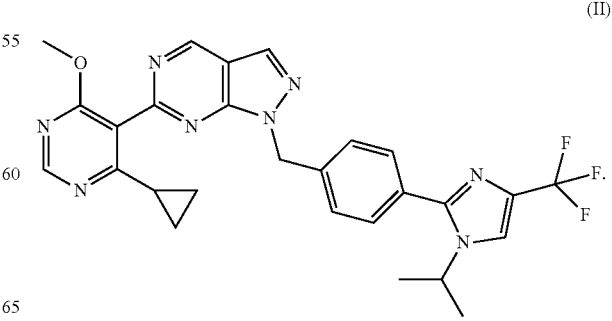

(II)

In some embodiments, crystalline Form F is an anhydrate.

In some embodiments, crystalline Form F is characterized by an XRPD pattern having peaks at 10.7±0.2, 14.3±0.2, and 21.8±0.2 degrees two theta when measured by Cu Kα radiation. In another embodiment, crystalline Form F is characterized by an XRPD pattern having peaks at 10.7±0.2, 14.3±0.2, 21.5±0.2, and 21.8±0.2 degrees two theta when measured by Cu Kα radiation. In another embodiment, crystalline Form F is characterized by an XRPD pattern having peaks at 10.7±0.2, 14.3±0.2, 15.8±0.2, 21.5±0.2, and 21.8±0.2 degrees two theta when measured by Cu Kα radiation. In another embodiment, crystalline Form F is characterized by an XRPD pattern having peaks at 10.7±0.2, 14.3±0.2, 15.8±0.2, 21.5±0.2, 21.8±0.2, and 25.0±0.2 degrees two theta when measured by Cu Kα radiation.

In some embodiments, crystalline Form F is characterized by an XRPD pattern substantially as shown in FIG. 25.

In some embodiments, crystalline Form F is characterized by three or more, four or more, five or more, or six or more XRPD peaks listed in Table 5 below.

TABLE 5a

Select XRPD Peaks for Crystalline Form F

| Pos. [°2Th.] | d-spacing [Å] | Rel. Int. [%] |
|---|---|---|
| 10.72 | 8.23 | 100.00 |
| 12.47 | 7.10 | 19.81 |
| 13.22 | 6.70 | 20.56 |
| 13.90 | 6.37 | 35.64 |
| 14.33 | 6.18 | 72.57 |
| 14.74 | 6.01 | 31.61 |
| 15.24 | 5.81 | 16.43 |
| 15.44 | 5.74 | 6.98 |
| 15.84 | 5.59 | 56.79 |
| 17.11 | 5.18 | 43.13 |
| 17.78 | 4.99 | 20.95 |
| 18.27 | 4.85 | 7.95 |
| 19.17 | 4.63 | 37.89 |
| 19.88 | 4.47 | 48.12 |
| 20.50 | 4.33 | 28.91 |
| 21.07 | 4.22 | 10.77 |
| 21.46 | 4.14 | 72.65 |
| 21.79 | 4.08 | 74.85 |
| 22.37 | 3.98 | 13.10 |
| 22.90 | 3.88 | 14.49 |
| 23.81 | 3.74 | 10.69 |
| 24.49 | 3.64 | 20.15 |
| 25.01 | 3.56 | 64.70 |
| 25.36 | 3.51 | 9.84 |
| 26.10 | 3.41 | 7.06 |
| 26.51 | 3.36 | 33.37 |
| 27.62 | 3.23 | 4.35 |
| 28.84 | 3.10 | 4.06 |
| 29.39 | 3.04 | 4.26 |
| 29.88 | 2.99 | 6.83 |
| 30.66 | 2.92 | 21.82 |
| 32.35 | 2.77 | 9.88 |
| 33.94 | 2.64 | 7.09 |
| 40.95 | 2.20 | 5.21 |

TABLE 5b

XRPD Peaks for Crystalline Form F

| Pos. [°2Th.] | d-spacing [Å] | Rel. Int. [%] |
|---|---|---|
| 7.19 | 12.30 | 2.62 |
| 10.72 | 8.23 | 100.00 |
| 12.47 | 7.10 | 19.81 |
| 12.71 | 6.97 | 3.80 |
| 13.22 | 6.70 | 20.56 |
| 13.90 | 6.37 | 35.64 |
| 14.33 | 6.18 | 72.57 |
| 14.74 | 6.01 | 31.61 |
| 15.24 | 5.81 | 16.43 |
| 15.44 | 5.74 | 6.98 |
| 15.84 | 5.59 | 56.79 |
| 17.11 | 5.18 | 43.13 |
| 17.78 | 4.99 | 20.95 |
| 18.27 | 4.85 | 7.95 |
| 19.17 | 4.63 | 37.89 |
| 19.88 | 4.47 | 48.12 |
| 20.50 | 4.33 | 28.91 |
| 21.07 | 4.22 | 10.77 |
| 21.46 | 4.14 | 72.65 |
| 21.79 | 4.08 | 74.85 |
| 22.37 | 3.98 | 13.10 |
| 22.90 | 3.88 | 14.49 |
| 23.81 | 3.74 | 10.69 |
| 24.49 | 3.64 | 20.15 |
| 25.01 | 3.56 | 64.70 |
| 25.36 | 3.51 | 9.84 |
| 26.10 | 3.41 | 7.06 |
| 26.51 | 3.36 | 33.37 |
| 27.62 | 3.23 | 4.35 |
| 27.89 | 3.20 | 3.24 |
| 28.84 | 3.10 | 4.06 |
| 29.39 | 3.04 | 4.26 |
| 29.88 | 2.99 | 6.83 |
| 30.66 | 2.92 | 21.82 |
| 31.42 | 2.85 | 3.23 |
| 32.35 | 2.77 | 9.88 |
| 32.90 | 2.72 | 2.67 |
| 33.94 | 2.64 | 7.09 |
| 35.53 | 2.53 | 2.42 |
| 36.64 | 2.45 | 1.59 |
| 37.63 | 2.39 | 1.25 |
| 38.57 | 2.33 | 1.67 |
| 39.11 | 2.30 | 1.39 |
| 40.95 | 2.20 | 5.21 |
| 42.17 | 2.14 | 1.51 |
| 44.00 | 2.06 | 2.18 |
| 45.61 | 1.99 | 1.20 |
| 46.75 | 1.94 | 1.44 |
| 47.64 | 1.91 | 0.73 |

In some embodiments, crystalline Form F is characterized by an endothermic peak at from about 153° C. to about 160° C., or from about 154° C. to about 159° C., or from about 155° C. to about 158° C., as determined by DSC. In some embodiments, crystalline Form F is characterized by an endothermic peak at about 157° C., as determined by DSC.

In some embodiments, crystalline Form F is characterized by a DSC profile substantially as shown in FIG. 26.

In some embodiments, crystalline Form F is characterized by at least one of the following: a) an XRPD pattern as shown in FIG. 25; or b) a DSC profile as shown in FIG. 26.

In some embodiments, crystalline Form F is substantially free of other polymorphic forms. In some embodiments, crystalline Form F has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form F and a second solid state form of a compound of Formula (II). In some embodiments, the second solid state form of a compound of Formula (II) is crystalline Form A, or crystalline Form C, or crystalline Form D, or crystalline Form E, or crystalline Form 1, or crystalline Form 2, or crystalline Form 8, or crystalline Form 9.

In some embodiments, the present disclosure relates to a mixture comprising a majority of crystalline Form F as compared to other solid state forms of a compound of Formula (II).

6. Crystalline Form 1

In one aspect, the present disclosure relates to crystalline Form 1 of a hydrochloric acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

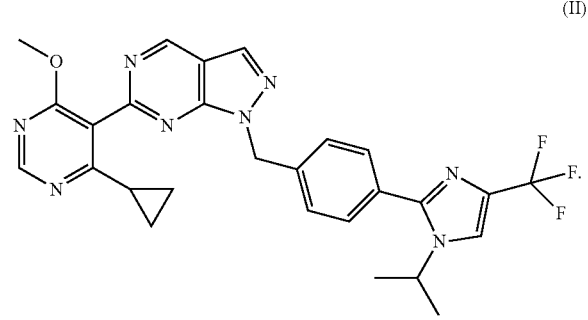 [SMILES: COc1ncnc(C2CC2)c1-c1ncc2cnn(Cc3ccc(-c4nc(C(F)(F)F)cn4C(C)C)cc3)c2n1]

(II)

In some embodiments, crystalline Form 1 is a 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine hydrochloride hydrate.

In some embodiments, the melting point of crystalline Form 1 is from about 140° C. to about 145° C. In some embodiments, the melting point of crystalline Form 1 is from about 140° C. to about 143° C. In some embodiments, the melting point of crystalline Form 1 is about 140.8° C.

In some embodiments, crystalline Form 1 is characterized by an XRPD pattern having peaks at 12.5±0.2, 22.4±0.2, and 23.9±0.2 degrees two theta when measured by Cu Kα radiation. In another embodiment, crystalline Form 1 is characterized by an XRPD pattern having peaks at 12.5±0.2, 17.2±0.2, 22.4±0.2, and 23.9±0.2 degrees two theta when measured by Cu Kα radiation. In another embodiment, crystalline Form 1 is characterized by an XRPD pattern having peaks at 12.5±0.2, 17.2±0.2, 19.7±0.2, 22.4±0.2, and 23.9±0.2 degrees two theta when measured by Cu Kα radiation. In another embodiment, crystalline Form 1 is characterized by an XRPD pattern having peaks at 12.5±0.2, 17.2±0.2, 19.7±0.2, 22.4±0.2, 23.1±0.2, and 23.9±0.2 degrees two theta when measured by Cu Kα radiation.

In some embodiments, crystalline Form 1 is characterized by an XRPD pattern substantially as shown in FIG. 7.

In some embodiments, crystalline Form 1 is characterized by three or more, four or more, five or more, or six or more XRPD peaks listed in Table 6 below.

TABLE 6

| XRPD Peaks for Crystalline Form 1 | | |
|---|---|---|
| Pos. [°2Th.] | d-spacing [Å] | Rel. Int. [%] |
| 7.63 | 11.58 | 12.85 |
| 10.23 | 8.65 | 24.44 |
| 12.53 | 7.07 | 100.00 |
| 13.41 | 6.60 | 25.51 |
| 13.92 | 6.36 | 37.74 |
| 15.40 | 5.75 | 18.89 |
| 16.34 | 5.43 | 22.09 |

TABLE 6-continued

| XRPD Peaks for Crystalline Form 1 | | |
|---|---|---|
| Pos. [°2Th.] | d-spacing [Å] | Rel. Int. [%] |
| 17.20 | 5.16 | 46.14 |
| 17.76 | 4.99 | 26.80 |
| 18.76 | 4.73 | 27.32 |
| 19.66 | 4.52 | 48.32 |
| 22.39 | 3.97 | 48.78 |
| 23.06 | 3.86 | 49.26 |
| 23.93 | 3.72 | 76.96 |
| 26.59 | 3.35 | 26.56 |

In some embodiments, crystalline Form 1 is characterized by an endothermic peak at from about 136° C. to about 146° C., or from about 138° C. to about 144° C., or from about 140° C. to about 143° C., as determined by DSC. In some embodiments, crystalline Form 1 is characterized by an endothermic peak at about 142.1° C., as determined by DSC.

In some embodiments, crystalline Form 1 is characterized by a DSC profile substantially as shown in FIG. 8.

In some embodiments, crystalline Form 1 is characterized by from an about 3.0 wt % to an about 5.0 wt % loss between about 30° C. and about 100° C. In some embodiments, crystalline Form 1 is characterized by from an about 3.5 wt % to an about 4.5 wt % loss between about 30° C. and about 100° C. In some embodiments, crystalline Form 1 is characterized by an about 4.04 wt % loss between about 30° C. and about 100° C.

In some embodiments, crystalline Form 1 is characterized by a TGA profile substantially as shown in FIG. 8.

In some embodiments, crystalline Form 1 is characterized by from an about 12.0 wt % to an about 14.0 wt % loss between room temperature and about 180° C. In some embodiments, crystalline Form 1 is characterized by from an about 12.8 wt % to an about 13.4 wt % loss between room temperature and about 180° C. In some embodiments, crystalline Form 1 is characterized by an about 13.13 wt % loss between room temperature and about 180° C.

In some embodiments, crystalline Form 1 is characterized by at least two of the following: a) an XRPD pattern as shown in FIG. 7; b) a DSC profile as shown in FIG. 8; or c) a TGA profile as shown in FIG. 8.

In some embodiments, crystalline Form 1 is substantially free of other polymorphic forms. In some embodiments, crystalline Form 1 has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form 1 and a second solid state form of a compound of Formula (II). In some embodiments, the second solid state form of a compound of Formula (II) is crystalline Form A, or crystalline Form C, or crystalline Form D, or crystalline Form E, or crystalline Form F, or crystalline Form 2, or crystalline Form 8, or crystalline Form 9. In some embodiments, the second solid state form of a compound of Formula (II) is crystalline Form A, or crystalline Form C, or crystalline Form D, or crystalline Form E, or crystalline Form 2.

In some embodiments, the present disclosure relates to a mixture comprising a majority of crystalline Form 1 as compared to other solid state forms of a compound of Formula (II).

7. Crystalline Form 2

In one aspect, the present disclosure relates to crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

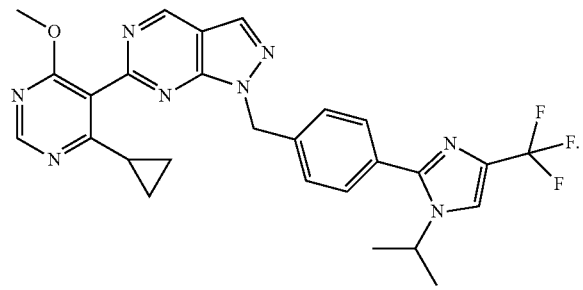

(II)

In some embodiments, crystalline Form 2 is an anhydrate.

In some embodiments, the melting point of crystalline Form 2 is from about 184° C. to about 190° C. In some embodiments, the melting point of crystalline Form 2 is from about 186° C. to about 188° C. In some embodiments, the melting point of crystalline Form 2 is about 187° C.

In some embodiments, crystalline Form 2 is characterized by an XRPD pattern having peaks at 16.6±0.2, 18.7±0.2, and 22.5±0.2 degrees two theta when measured by Cu Kα radiation. In another embodiment, crystalline Form 2 is characterized by an XRPD pattern having peaks at 16.6±0.2, 18.7±0.2, 22.3±0.2, and 22.5±0.2 degrees two theta when measured by Cu Kα radiation. In another embodiment, crystalline Form 2 is characterized by an XRPD pattern having peaks at 16.6±0.2, 18.7±0.2, 22.3±0.2, 22.5±0.2, and 26.0±0.2 degrees two theta when measured by Cu Kα radiation. In another embodiment, crystalline Form 2 is characterized by an XRPD pattern having peaks at 16.6±0.2, 18.7±0.2, 20.8±0.2, 22.3±0.2, 22.5±0.2, and 26.0±0.2 degrees two theta when measured by Cu Kα radiation.

In some embodiments, crystalline Form 2 is characterized by an XRPD pattern substantially as shown in FIG. 9.

In some embodiments, crystalline Form 2 is characterized by three or more, four or more, five or more, or six or more XRPD peaks listed in Table 7 below.

TABLE 7a

| Select XRPD Peaks for Crystalline Form 2 | | |
|---|---|---|
| Pos. [°2Th.] | d-spacing [Å] | Rel. Int. [%] |
| 8.06 | 10.97 | 21.93 |
| 12.12 | 7.30 | 23.48 |
| 13.30 | 6.66 | 9.94 |
| 14.31 | 6.19 | 37.35 |
| 14.95 | 5.93 | 21.37 |
| 15.47 | 5.73 | 12.00 |
| 16.42 | 5.40 | 38.25 |
| 16.58 | 5.35 | 59.48 |
| 17.35 | 5.11 | 18.11 |
| 18.18 | 4.88 | 30.28 |
| 18.72 | 4.74 | 61.10 |
| 19.68 | 4.51 | 5.01 |
| 20.40 | 4.35 | 6.62 |
| 20.80 | 4.27 | 37.19 |
| 22.29 | 3.99 | 95.77 |
| 22.49 | 3.95 | 100.00 |

TABLE 7a-continued

| Select XRPD Peaks for Crystalline Form 2 | | |
|---|---|---|
| Pos. [°2Th.] | d-spacing [Å] | Rel. Int. [%] |
| 23.00 | 3.87 | 21.16 |
| 23.65 | 3.76 | 19.85 |
| 25.96 | 3.43 | 38.67 |
| 26.40 | 3.38 | 7.96 |
| 26.88 | 3.32 | 8.15 |
| 28.95 | 3.08 | 8.97 |
| 30.06 | 2.97 | 6.51 |

TABLE 7b

| XRPD Peaks for Crystalline Form 2 | | |
|---|---|---|
| Pos. [°2Th.] | d-spacing [Å] | Rel. Int. [%] |
| 8.06 | 10.97 | 21.93 |
| 12.12 | 7.30 | 23.48 |
| 13.30 | 6.66 | 9.94 |
| 14.31 | 6.19 | 37.35 |
| 14.95 | 5.93 | 21.37 |
| 15.47 | 5.73 | 12.00 |
| 16.42 | 5.40 | 38.25 |
| 16.58 | 5.35 | 59.48 |
| 17.35 | 5.11 | 18.11 |
| 18.18 | 4.88 | 30.28 |
| 18.72 | 4.74 | 61.10 |
| 19.68 | 4.51 | 5.01 |
| 20.40 | 4.35 | 6.62 |
| 20.80 | 4.27 | 37.19 |
| 22.29 | 3.99 | 95.77 |
| 22.49 | 3.95 | 100.00 |
| 23.00 | 3.87 | 21.16 |
| 23.65 | 3.76 | 19.85 |
| 25.96 | 3.43 | 38.67 |
| 26.40 | 3.38 | 7.96 |
| 26.88 | 3.32 | 8.15 |
| 28.95 | 3.08 | 8.97 |
| 30.06 | 2.97 | 6.51 |
| 31.12 | 2.87 | 2.70 |
| 34.18 | 2.62 | 1.65 |

In some embodiments, crystalline Form 2 is characterized by an endothermic peak at from about 181° C. to about 191° C., or from about 183° C. to about 189° C., or from about 185° C. to about 187° C., as determined by DSC. In some embodiments, crystalline Form 2 is characterized by an endothermic peak at about 186.0° C., as determined by DSC.

In some embodiments, crystalline Form 2 is characterized by a DSC profile substantially as shown in FIG. 10.

In some embodiments, crystalline Form 2 is characterized by from an about 2.5 wt % to an about 3.5 wt % loss between room temperature and about 170° C. In some embodiments, crystalline Form 2 is characterized by from an about 3.0 wt % to an about 3.4 wt % loss between room temperature and about 170° C. In some embodiments, crystalline Form 2 is characterized by an about 3.17 wt % loss between room temperature and about 170° C.

In some embodiments, crystalline Form 2 is characterized by a TGA profile substantially as shown in FIG. 10.

In some embodiments, crystalline Form 2 is characterized by at least two of the following: a) an XRPD pattern as shown in FIG. 9; b) a DSC profile as shown in FIG. 10; or c) a TGA profile as shown in FIG. 10.

In some embodiments, crystalline Form 2 has a unit cell that indexes as monoclinic.

In some embodiments, crystalline Form 2 has a unit cell with an a value of about 11.113 Å, a b value of about 12.356 Å, and a c value of about 24.048 Å. In other embodiments, Form 2 has a unit cell with a volume of about 3223.93 Å$^3$.

The unit cell parameters for crystalline Form 2 are as follows:

| Crystal System | Monoclinic |
|---|---|
| a [Å] | 11.113 |
| b [Å] | 12.356 |
| c [Å] | 24.048 |
| α [deg] | 90 |
| β [deg] | 102.48 |
| γ [deg] | 90 |
| Volume [Å³] | 3223.93 |
| Z CalMolated density [g/cm³] | 4, 1.419 |
| Crystal Size [mm³] | 0.31 × 0.15 × 0.11 |
| Space Group(s) | P2$_{1/c}$ |

In some embodiments, crystalline Form 2 is substantially free of other polymorphic forms. In some embodiments, crystalline Form 2 has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form 2 and a second solid state form of a compound of Formula (II). In some embodiments, the second solid state form of a compound of Formula (II) is crystalline Form A, or crystalline Form C, or crystalline Form D, or crystalline Form E, or crystalline Form F, or crystalline Form 1, or crystalline Form 8, or crystalline Form 9. In some embodiments, the second solid state form of a compound of Formula (II) is crystalline Form A, or crystalline Form C, or crystalline Form D, or crystalline Form E, or crystalline Form 1.

In some embodiments, the present disclosure relates to a mixture comprising a majority of crystalline Form 2 as compared to other solid state forms of a compound of Formula (II).

Crystalline Form 2 exhibits chemical and physical properties that are unexpected and bioavailability properties that are advantageous compared to the free base forms. In particular, as shown in FIG. 21, 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and gentisic acid exhibit significant hydrogen bonding interactions despite being an interaction between a weak base and a weak acid, respectively.

Additionally, as shown in Example 14, crystalline Form 2 surprisingly exhibits increased mouse oral exposure levels as compared to other solid state forms of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II). For example, as shown in Example 14, in some embodiments, crystalline Form 2 (gentisic acid co-crystal) exhibits higher exposure levels at about 300 mg/kg than crystalline Form A (freebase).

8. Crystalline Form 3

In another aspect, the present disclosure relates to crystalline Form 3 of a hydrochloric acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

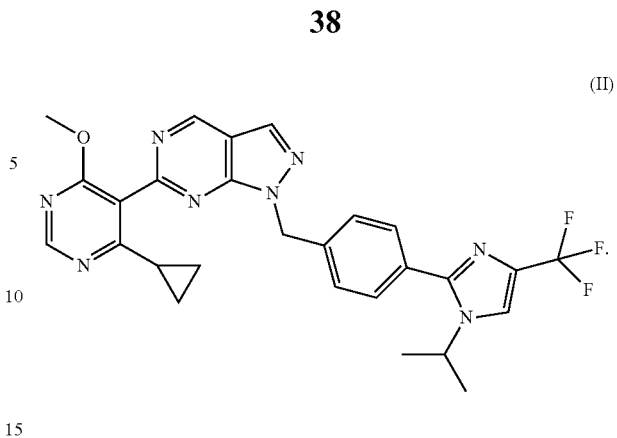

In some embodiments, crystalline Form 3 is characterized by an XRPD pattern substantially as shown in FIG. 15.

9. Crystalline Form 4

In another aspect, the present disclosure relates to crystalline Form 4 of a hydrobromic acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

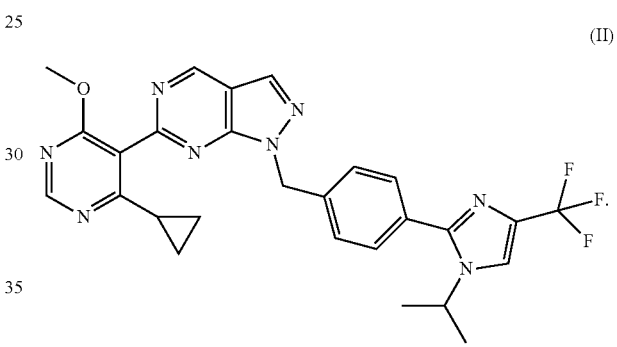

In some embodiments, crystalline Form 4 is characterized by an XRPD pattern substantially as shown in FIG. 16.

10. Crystalline Form 5

In another aspect, the present disclosure relates to crystalline Form 5 of a hydrobromic acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

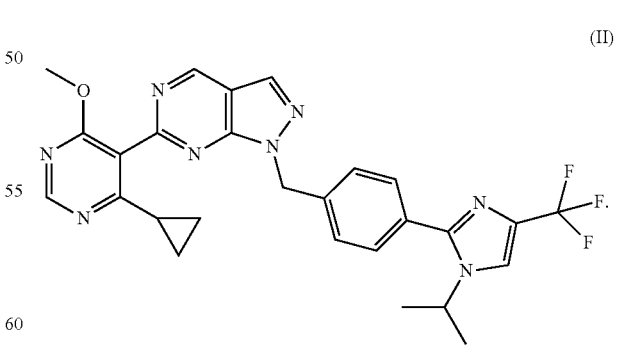

In some embodiments, crystalline Form 5 is characterized by an XRPD pattern substantially as shown in FIG. 17.

11. Crystalline Form 6

In another aspect, the present disclosure relates to crystalline Form 6 of an ethanedisulfonic acid salt of 6-(4- cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

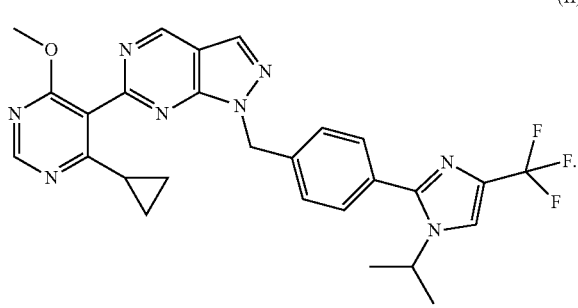
(II)

In some embodiments, crystalline Form 6 is characterized by an XRPD pattern substantially as shown in FIG. 18.

12. Crystalline Form 7

In another aspect, the present disclosure relates to crystalline Form 7 of a methanesulfonic acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

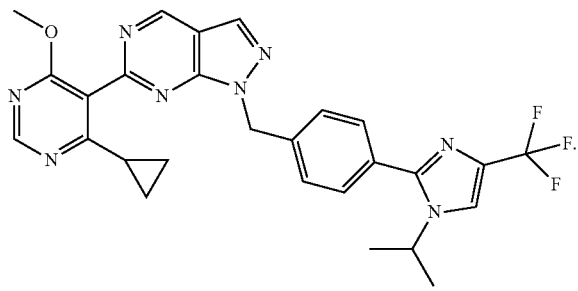
(II)

In some embodiments, crystalline Form 7 is characterized by an XRPD pattern substantially as shown in FIG. 19.

13. Crystalline Form 8

In one aspect, the present disclosure relates to crystalline Form 8 of a benzoic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

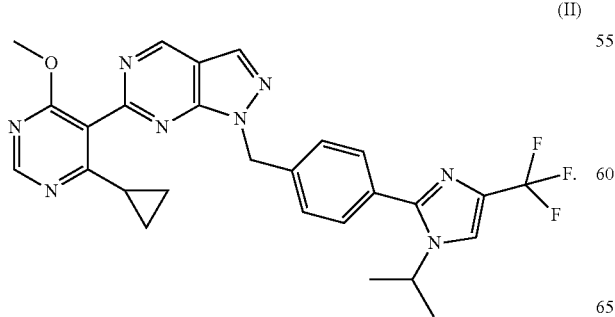
(II)

In some embodiments, crystalline Form 8 is an anhydrate.

In some embodiments, the melting point of crystalline Form 8 is from about 100° C. to about 110° C. In some embodiments, the melting point of crystalline Form 8 is from about 102° C. to about 108° C. In some embodiments, the melting point of crystalline Form 8 is about 105° C.

In some embodiments, crystalline Form 8 is characterized by an XRPD pattern having peaks at 12.1±0.2, 14.2±0.2, and 16.5±0.2 degrees two theta when measured by Cu Kα radiation. In another embodiment, crystalline Form 8 is characterized by an XRPD pattern having peaks at 12.1±0.2, 16.5±0.2, 19.0±0.2, and 21.0±0.2 degrees two theta when measured by Cu Kα radiation. In another embodiment, crystalline Form 8 is characterized by an XRPD pattern having peaks at 12.1±0.2, 14.2±0.2, 16.5±0.2, and 21.0±0.2 degrees two theta when measured by Cu Kα radiation. In another embodiment, crystalline Form 8 is characterized by an XRPD pattern having peaks at 12.1±0.2, 16.5±0.2, 21.0±0.2, 23.0±0.2, and 25.7±0.2 degrees two theta when measured by Cu Kα radiation.

In some embodiments, crystalline Form 8 is characterized by an XRPD pattern substantially as shown in FIG. 29.

In some embodiments, crystalline Form 8 is characterized by three or more, four or more, five or more, or six or more XRPD peaks listed in Table 8 below.

TABLE 8

XRPD Peaks for Crystalline Form 8

| Pos. [°2Th.] | d-spacing [Å] | Rel. Int. [%] |
|---|---|---|
| 7.39 | 11.95 | 25.5 |
| 7.98 | 11.08 | 39.2 |
| 8.44 | 10.47 | 24.9 |
| 10.24 | 8.63 | 29.7 |
| 11.02 | 8.02 | 26.5 |
| 12.13 | 7.29 | 84.4 |
| 12.48 | 7.09 | 46.2 |
| 14.19 | 6.24 | 68.4 |
| 14.66 | 6.04 | 29.9 |
| 15.25 | 5.80 | 20.7 |
| 16.00 | 5.53 | 17.3 |
| 16.52 | 5.36 | 100 |
| 16.83 | 5.26 | 29.3 |
| 17.28 | 5.13 | 29.8 |
| 18.02 | 4.92 | 50.4 |
| 18.38 | 4.82 | 25.3 |
| 18.96 | 4.68 | 90.6 |
| 19.54 | 4.54 | 35.9 |
| 21.04 | 4.22 | 69.8 |
| 21.31 | 4.17 | 35.5 |
| 21.95 | 4.05 | 39.6 |
| 22.36 | 3.97 | 60.1 |
| 22.63 | 3.93 | 39.4 |
| 22.98 | 3.87 | 74.3 |
| 23.18 | 3.83 | 39.9 |
| 23.43 | 3.79 | 33.3 |
| 24.13 | 3.69 | 13.5 |
| 24.70 | 3.60 | 19.2 |
| 25.74 | 3.46 | 78.1 |
| 26.52 | 3.36 | 27.1 |
| 26.78 | 3.33 | 14.9 |
| 27.32 | 3.26 | 11.2 |
| 28.59 | 3.12 | 31.2 |
| 28.84 | 3.09 | 38.9 |
| 29.28 | 3.05 | 15.2 |
| 29.54 | 3.02 | 13.9 |
| 29.92 | 2.98 | 12.3 |
| 30.31 | 2.95 | 16.8 |
| 30.77 | 2.90 | 20.3 |
| 31.03 | 2.88 | 13.8 |
| 31.31 | 2.85 | 13.9 |
| 31.64 | 2.83 | 9.3 |
| 32.91 | 2.72 | 9.5 |

TABLE 8-continued

XRPD Peaks for Crystalline Form 8

| Pos. [°2Th.] | d-spacing [Å] | Rel. Int. [%] |
|---|---|---|
| 33.16 | 2.70 | 13.4 |
| 33.49 | 2.67 | 10.6 |
| 33.99 | 2.64 | 8.8 |
| 34.88 | 2.57 | 9 |
| 35.81 | 2.51 | 7.7 |
| 36.40 | 2.47 | 9.4 |
| 36.64 | 2.45 | 8.4 |
| 37.04 | 2.42 | 8.3 |
| 37.40 | 2.40 | 13.6 |
| 37.66 | 2.39 | 8.3 |
| 38.19 | 2.35 | 12.7 |
| 39.39 | 2.29 | 8 |
| 39.95 | 2.25 | 7.2 |
| 40.82 | 2.21 | 7.4 |
| 41.74 | 2.16 | 7.2 |

In some embodiments, crystalline Form 8 is characterized by an endothermic peak at from about 100° C. to about 110° C., or from about 102° C. to about 108° C., or from about 104° C. to about 106° C., as determined by DSC. In some embodiments, crystalline Form 8 is characterized by an endothermic peak at about 105.3° C., as determined by DSC.

In some embodiments, crystalline Form 8 is characterized by a DSC profile substantially as shown in FIG. 30.

In some embodiments, crystalline Form 8 is characterized by from an about 14 wt % to an about 24 wt % loss between about 120° C. and about 300° C. In some embodiments, crystalline Form 8 is characterized by from an about 16 wt % to an about 20 wt % loss between about 120° C. and about 300° C. In some embodiments, crystalline Form 8 is characterized by from an about 18 wt % to an about 19 wt % loss between about 120° C. and about 300° C. In some embodiments, crystalline Form 8 is characterized by an about 18.8 wt % loss between about 120° C. and about 300° C.

In some embodiments, crystalline Form 8 is characterized by a TG-FTIR profile substantially as shown in FIG. 31.

In some embodiments, crystalline Form 8 is characterized by at least two of the following: a) an XRPD pattern as shown in FIG. 29; b) a DSC profile as shown in FIG. 30; or c) a TG-FTIR profile as shown in FIG. 31.

In some embodiments, crystalline Form 8 has a unit cell that indexes as monoclinic.

In some embodiments, crystalline Form 8 has a unit cell with an a value of about 10.61070(10) Å, a b value of about 12.39940(10) Å, and a c value of about 24.15170(10) Å. In other embodiments, Form 8 has a unit cell with a volume of about 3114.74(4) Å³.

The unit cell parameters for crystalline Form 8 are as follows:

| Crystal System | Monoclinic |
|---|---|
| a [Å] | 10.61070(10) |
| b [Å] | 12.39940(10) |
| c [Å] | 24.15170(10) |
| α [deg] | 90 |
| β [deg] | 101.4110(10) |
| γ [deg] | 90 |
| Volume [Å³] | 3114.74(4) |
| Z, CalMolated density [g/cm³] | 4, 1.400 |
| Crystal Size [mm³] | 0.047 × 0.043 × 0.033 |
| Space Group(s) | P2$_{1/n}$ |

In some embodiments, crystalline Form 8 is substantially free of other polymorphic forms. In some embodiments, crystalline Form 8 has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form 8 and a second solid state form of a compound of Formula (II). In some embodiments, the second solid state form of a compound of Formula (II) is crystalline Form A, or crystalline Form C, or crystalline Form D, or crystalline Form E, or crystalline Form F, or crystalline Form 1, or crystalline Form 2, or crystalline Form 9.

In some embodiments, the present disclosure relates to a mixture comprising a majority of crystalline Form 8 as compared to other solid state forms of a compound of Formula (II).

14. Crystalline Form 9

In one aspect, the present disclosure relates to crystalline Form 9 of a salicylic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

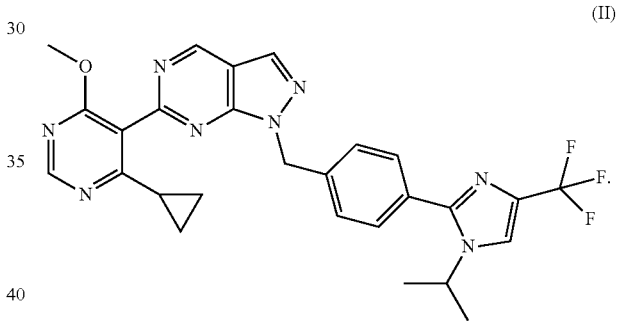

(II)

In some embodiments, crystalline Form 9 is an anhydrate.

In some embodiments, crystalline Form 9 is characterized by an XRPD pattern having peaks at 11.0±0.2, 16.5±0.2, and 25.3±0.2 degrees two theta when measured by Cu Kα radiation. In another embodiment, crystalline Form 9 is characterized by an XRPD pattern having peaks at 11.0±0.2, 16.5±0.2, 17.3±0.2, and 25.3±0.2 degrees two theta when measured by Cu Kα radiation.

In some embodiments, crystalline Form 9 is characterized by an XRPD pattern substantially as shown in FIG. 33.

In some embodiments, crystalline Form 9 is characterized by three or more, four or more, five or more, or six or more XRPD peaks listed in Table 9 below.

TABLE 9

XRPD Peaks for Crystalline Form 9

| Pos. [°2Th.] | d-spacing [Å] | Rel. Int. [%] |
|---|---|---|
| 8.00 | 11.04 | 22.7 |
| 9.84 | 8.98 | 12.6 |
| 10.25 | 8.62 | 13.4 |
| 10.97 | 8.06 | 72.1 |
| 12.16 | 7.27 | 44.6 |
| 13.21 | 6.70 | 11.4 |

TABLE 9-continued

XRPD Peaks for Crystalline Form 9

| Pos. [°2Th.] | d-spacing [Å] | Rel. Int. [%] |
|---|---|---|
| 14.30 | 6.19 | 28.3 |
| 14.71 | 6.02 | 17.6 |
| 15.34 | 5.77 | 14.7 |
| 15.76 | 5.62 | 14 |
| 16.08 | 5.51 | 11.2 |
| 16.47 | 5.38 | 70.7 |
| 17.25 | 5.14 | 60.9 |
| 17.67 | 5.02 | 27.2 |
| 18.06 | 4.91 | 26.8 |
| 18.78 | 4.72 | 37.9 |
| 19.07 | 4.65 | 21.2 |
| 19.68 | 4.51 | 20.8 |
| 20.86 | 4.26 | 37.1 |
| 21.08 | 4.21 | 18.9 |
| 21.61 | 4.11 | 14.2 |
| 21.87 | 4.06 | 11.9 |
| 22.14 | 4.01 | 23.9 |
| 22.36 | 3.97 | 33.6 |
| 22.70 | 3.91 | 18.9 |
| 23.01 | 3.86 | 36.7 |
| 23.31 | 3.81 | 19 |
| 23.56 | 3.77 | 22 |
| 23.87 | 3.72 | 8.9 |
| 24.22 | 3.67 | 12.8 |
| 24.49 | 3.63 | 7.7 |
| 24.89 | 3.58 | 11.5 |
| 25.31 | 3.52 | 100 |
| 25.96 | 3.43 | 34.7 |
| 26.40 | 3.37 | 9.8 |
| 26.61 | 3.35 | 8.9 |
| 27.13 | 3.28 | 6.1 |
| 28.07 | 3.18 | 12.1 |
| 28.42 | 3.14 | 11.8 |
| 28.74 | 3.10 | 41.6 |
| 28.94 | 3.08 | 24.2 |
| 29.30 | 3.05 | 7.6 |
| 29.50 | 3.03 | 6.6 |
| 29.96 | 2.98 | 11.4 |
| 30.40 | 2.94 | 9 |
| 30.67 | 2.91 | 22.9 |
| 30.88 | 2.89 | 13.9 |
| 31.27 | 2.86 | 8.1 |
| 31.92 | 2.80 | 6.1 |
| 32.78 | 2.73 | 6 |
| 33.12 | 2.70 | 7.7 |
| 33.37 | 2.68 | 6.2 |
| 33.70 | 2.66 | 10.4 |
| 34.02 | 2.63 | 4.3 |
| 34.91 | 2.57 | 4.8 |
| 35.23 | 2.55 | 5 |
| 35.54 | 2.52 | 5.9 |
| 35.81 | 2.51 | 5.5 |
| 36.33 | 2.47 | 5.4 |
| 36.72 | 2.45 | 6.7 |
| 37.10 | 2.42 | 5.9 |
| 37.47 | 2.40 | 7.3 |
| 38.06 | 2.36 | 10.1 |
| 38.60 | 2.33 | 4.6 |
| 39.33 | 2.29 | 5 |
| 39.69 | 2.27 | 5.3 |
| 40.01 | 2.25 | 13 |
| 40.65 | 2.22 | 5 |
| 40.90 | 2.20 | 4.2 |
| 41.35 | 2.18 | 4.2 |

In some embodiments, crystalline Form 9 is characterized by a $^1$H NMR profile substantially as shown in FIG. 34.

In some embodiments, crystalline Form 9 is characterized by at least one of the following: a) an XRPD pattern as shown in FIG. 33; or b) $^1$H NMR profile as shown in FIG. 34.

In some embodiments, crystalline Form 9 has a unit cell that indexes as monoclinic.

In some embodiments, crystalline Form 9 has a unit cell with an a value of about 10.8387(11) Å, a b value of about 12.3761(12) Å, and a c value of about 24.242(2) Å. In other embodiments, Form 9 has a unit cell with a volume of about 3173.1(5) Å$^3$.

The unit cell parameters for crystalline Form 9 are as follows:

| Crystal System | Monoclinic |
|---|---|
| a [Å] | 10.8387(11) |
| b [Å] | 12.3761(12) |
| c [Å] | 24.242(2) |
| α [deg] | 90 |
| β [deg] | 102.631(5) |
| γ [deg] | 90 |
| Volume [Å$^3$] | 3173.1(5) |
| Z, CalMolated density [g/cm$^3$] | 4, 1.408 |
| Crystal Size [mm$^3$] | 0.08 × 0.06 × 0.05 |
| Space Group(s) | P2$_{1/c}$ |

In some embodiments, crystalline Form 9 is substantially free of other polymorphic forms. In some embodiments, crystalline Form 9 has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form 9 and a second solid state form of a compound of Formula (II). In some embodiments, the second solid state form of a compound of Formula (II) is crystalline Form A, or crystalline Form C, or crystalline Form D, or crystalline Form E, or crystalline Form F, or crystalline Form 1, or crystalline Form 2, or crystalline Form 8.

In some embodiments, the present disclosure relates to a mixture comprising a majority of crystalline Form 9 as compared to other solid state forms of a compound of Formula (II).

B. Compound of Formula (III)

In one aspect, the present disclosure relates to a solid state form of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III):

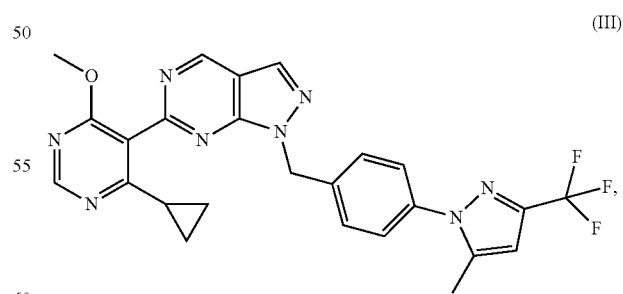

(III)

or a pharmaceutically acceptable salt thereof.

In some embodiments, the solid state form is an amorphous form of a compound of Formula (III). In some embodiments, the amorphous form is a hydrate, anhydrate, or solvate thereof. In some embodiments, the amorphous form is substantially free of other polymorphic forms. In some embodiments, the amorphous form has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In some embodiments, the present disclosure relates to a mixture comprising a majority of the amorphous form as compared to other solid state forms of a compound of Formula (III).

In some embodiments, the solid state form is a crystalline form of a compound of Formula (III). In some embodiments, the crystalline form is a hydrate, anhydrate, or solvate thereof.

In some embodiments, the solid state form of a compound of Formula (III) is selected from the group consisting of:
 a) crystalline Form A1, wherein Form A1 is characterized by an XRPD pattern having peaks at 16.1±0.2, 16.7±0.2, and 24.8±0.2 degrees two theta; and
 b) crystalline Form B1, wherein Form B1 is characterized by an XRPD pattern having peaks at 12.9±0.2, 14.5±0.2, and 22.6±0.2 degrees two theta.

In some embodiments, the solid state form is a pharmaceutically acceptable salt or co-crystal of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III). In some embodiments, the pharmaceutically acceptable salt or co-crystal is formed between 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) and a pharmaceutically acceptable acid.

In some embodiments, the pharmaceutically acceptable acid is selected from the group consisting of 1-hydroxy-2-naphthoic acid, 4-aminosalicylic acid, ascorbic acid, adipic acid, L-aspartic acid, benzene sulfonic acid, benzoic acid, trans-cinnamic acid, citric acid, ethanedisulfonic acid, fumaric acid, galactaric acid, gentisic acid, gluconic acid, D-glucuronic acid, glutamic acid, glutaric acid, glycolic acid, hexanoic acid, hippuric acid, hydrobromic acid, hydrochloric acid, lactic acid, maleic acid, L-malic acid, malonic acid, R-mandelic acid, methanesulfonic acid, mucic acid, naphthalene sulfonic acid, nicotinic acid, oxalic acid, palmitic acid, p-toluene sulfonic acid, phosphoric acid, propionic acid, saccharin, salicylic acid, stearic acid, succinic acid, sulfuric acid, L-tartaric acid, vanillic acid, vanillin, ethyl maltol, gallic acid, gallic acid ethyl ester, 4-hydroxybenzoic acid, 4-hydroxybenzoic acid methyl ester, 3,4,5-trihydroxybenzoic acid, nicotinamide, L-proline, and D-sorbitol. In some embodiments, the pharmaceutically acceptable acid is selected from the group consisting of hydrochloric acid, hydrobromic acid, ethanedisulfonic acid, methanesulfonic acid, gentisic acid, benzoic acid, salicylic acid, and gallic acid. In some embodiments, the pharmaceutically acceptable acid is selected from the group consisting of hydrochloric acid, hydrobromic acid, ethanedisulfonic acid, methanesulfonic acid, and gentisic acid. In some embodiments, the pharmaceutically acceptable acid is a benzoic acid derivative. In some embodiments, the pharmaceutically acceptable acid is a benzoic acid derivative substituted with one or more hydroxy groups. In some embodiments, the pharmaceutically acceptable acid is a benzoic acid derivative substituted with one hydroxy group. In some embodiments, the benzoic acid derivative substituted with one hydroxy group is salicylic acid. In some embodiments, the pharmaceutically acceptable acid is a benzoic acid derivative substituted with two hydroxy groups. In some embodiments, the benzoic acid derivative substituted with two hydroxy groups is gentisic acid. In some embodiments, the pharmaceutically acceptable acid is a benzoic acid derivative substituted with three hydroxy groups. In some embodiments, the benzoic acid derivative substituted with three hydroxy groups is gallic acid. In some embodiments, the benzoic acid derivative is selected from the group consisting of salicylic acid, gentisic acid, and gallic acid. In some embodiments, the pharmaceutically acceptable acid is hydrochloric acid. In some embodiments, the pharmaceutically acceptable acid is gentisic acid. In some embodiments the, the pharmaceutically acceptable acid is benzoic acid. In some embodiments, the pharmaceutically acceptable acid is salicylic acid. In some embodiments the pharmaceutically acceptable acid is gallic acid.

In some embodiments, the pharmaceutically acceptable salt of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) is an amorphous form. In some embodiments, the amorphous form is substantially free of other polymorphic forms. In some embodiments, the amorphous form has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In some embodiments, the pharmaceutically acceptable salt or co-crystal of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) is a crystalline form.

In some embodiments, the pharmaceutically acceptable salt or co-crystal of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) is a hydrate, anhydrate, or solvate thereof.

The sections below discuss solid state forms of a compound of Formula (III) that have been identified and selected properties of those solid state forms.

1. Crystalline Form A1

In one aspect, the present disclosure relates to crystalline Form A1 of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III):

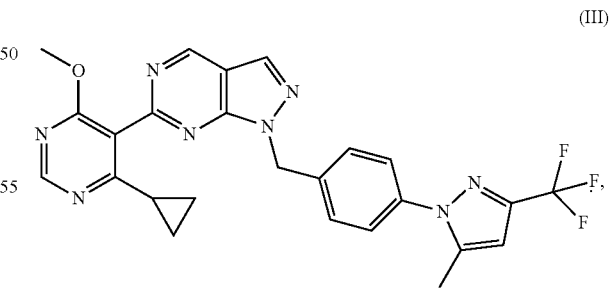

(III)

In some embodiments, crystalline Form A1 is an anhydrate.

In some embodiments, the melting point of crystalline Form A1 is from about 148° C. to about 152° C. In some embodiments, the melting point of crystalline Form A1 is from about 150° C. to about 152° C. In some embodiments, the melting point of crystalline Form A1 is about 150.5° C.

In some embodiments, crystalline Form A1 is characterized by an XRPD pattern having peaks at 16.1±0.2, 16.7±0.2, and 24.8±0.2 degrees two theta when measured by Cu Kα radiation. In another embodiment, crystalline Form A1 is characterized by an XRPD pattern having peaks at 16.1±0.2, 16.7±0.2, 22.2±0.2, and 24.8±0.2 degrees two theta when measured by Cu Kα radiation. In another embodiment, crystalline Form A1 is characterized by an XRPD pattern having peaks at 16.1±0.2, 16.7±0.2, 20.6±0.2, 22.2±0.2, and 24.8±0.2 degrees two theta when measured by Cu Kα radiation. In another embodiment, crystalline Form A1 is characterized by an XRPD pattern having peaks at 8.1±0.2, 16.1±0.2, 16.7±0.2, 20.6±0.2, 22.2±0.2, and 24.8±0.2 degrees two theta when measured by Cu Kα radiation.

In some embodiments, crystalline Form A1 is characterized by an XRPD pattern substantially as shown in FIG. 11.

In some embodiments, crystalline Form A1 is characterized by three or more, four or more, five or more, or six or more XRPD peaks listed in Table 10 below.

TABLE 10a

XRPD Peaks for Crystalline Form A1

| Pos. [°2Th.] | d-spacing [Å] | Rel. Int. [%] |
|---|---|---|
| 8.09 | 10.93 | 22.58 |
| 12.30 | 7.20 | 4.82 |
| 12.96 | 6.83 | 6.73 |
| 13.97 | 6.34 | 8.89 |
| 16.15 | 5.49 | 100.00 |
| 16.66 | 5.32 | 55.77 |
| 17.11 | 5.18 | 34.30 |
| 18.08 | 4.91 | 19.54 |
| 18.95 | 4.68 | 7.76 |
| 19.90 | 4.46 | 10.05 |
| 20.59 | 4.31 | 36.39 |
| 22.18 | 4.01 | 37.56 |
| 24.30 | 3.66 | 23.74 |
| 24.81 | 3.59 | 43.37 |
| 25.64 | 3.47 | 10.28 |
| 27.61 | 3.23 | 4.36 |
| 28.15 | 3.17 | 6.48 |
| 32.72 | 2.74 | 2.99 |

In some embodiments, crystalline Form A1 is characterized by an endothermic peak at from about 146° C. to about 154° C., or from about 148° C. to about 152° C., or from about 150° C. to about 152° C., as determined by DSC. In some embodiments, crystalline Form A1 is characterized by an endothermic peak at about 150.5° C., as determined by DSC.

In some embodiments, crystalline Form A1 is characterized by a DSC profile substantially as shown in FIG. 12.

In some embodiments, crystalline Form A1 is characterized by from an about 0.90 wt % to an about 1.0 wt % loss between room temperature and about 120° C. In some embodiments, crystalline Form A1 is characterized by from an about 0.92 wt % to an about 0.98 wt % loss between room temperature and about 120° C. In some embodiments, crystalline Form A1 is characterized by from an about 0.95 wt % loss between room temperature and about 120° C.

In some embodiments, crystalline Form A1 is characterized by a TGA profile substantially as shown in FIG. 12.

In some embodiments, crystalline Form A1 is characterized by at least two of the following: a) an XRPD pattern as shown in FIG. 11; b) a DSC profile as shown in FIG. 12; or c) a TGA profile as shown in FIG. 12.

In some embodiments, crystalline Form A1 has a unit cell that indexes as monoclinic.

In some embodiments, crystalline Form A1 has a unit cell with an a value of about 12.545 Å, a b value of about 8.640 Å, and a c value of about 21.660 Å. In other embodiments, Form A has a unit cell with a volume of about 2336.13 Å³.

The unit cell parameters for crystalline Form A1 are as follows:

| Crystal System | Monoclinic |
|---|---|
| a [Å] | 12.545 |
| b [Å] | 8.640 |
| c [Å] | 21.660 |
| α [deg] | 90 |
| β [deg] | 95.66 |
| γ [deg] | 90 |
| Volume [Å³] | 2336.13 |
| Z CalMolated density [g/cm³] | 4, 1.440 |
| Crystal Size [mm³] | 0.11 × 0.04 × 0.03 |
| Space Group(s) | P2$_{1/c}$ |

In some embodiments, crystalline Form A1 is substantially free of other polymorphic forms. In some embodiments, crystalline Form A1 has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%. In some embodiments, crystalline Form A1 has a polymorphic purity of at least 80%.

In another aspect, the present disclosure relates to a mixture comprising crystalline Form A1 and a second solid state form of a compound of Formula (III). In some embodiments, the second solid state form of a compound of Formula (III) is crystalline Form B1.

In some embodiments, the present disclosure relates to a mixture comprising a majority of crystalline Form A1 as compared to other solid state forms of a compound of Formula (III).

2. Crystalline Form B1

In one aspect, the present disclosure relates to crystalline Form B1 of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III):

(III)

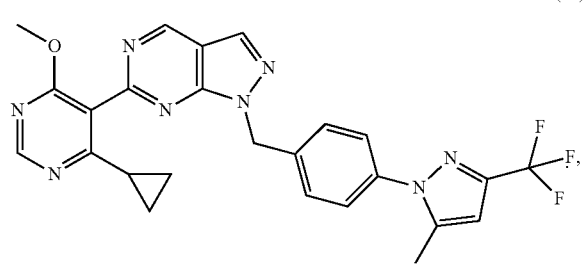

In some embodiments, crystalline Form B1 is an anhydrate.

In some embodiments, the melting point of crystalline Form B1 is from about 160° C. to about 164° C. In some embodiments, the melting point of crystalline Form B1 is from about 161° C. to about 163° C. In some embodiments, the melting point of crystalline Form B1 is about 162.1° C.

In some embodiments, crystalline Form B1 is characterized by an XRPD pattern having peaks at 12.9±0.2, 14.5±0.2, and 22.6±0.2 degrees two theta when measured by Cu Kα radiation. In another embodiment, crystalline Form B1 is characterized by an XRPD pattern having peaks at 12.9±0.2, 14.5±0.2, 16.7±0.2, and 22.6±0.2 degrees two theta when measured by Cu Kα radiation. In another embodiment, crystalline Form B1 is characterized by an XRPD pattern having peaks at 12.9±0.2, 14.5±0.2, 16.7±0.2, 22.6±0.2, 24.2±0.2 degrees two theta when measured by Cu Kα radiation. In another embodiment, crystalline Form B1 is characterized by an XRPD pattern having peaks at 12.9±0.2, 14.5±0.2, 16.7±0.2, 20.7±0.2, 22.6±0.2, 24.2±0.2 degrees two theta when measured by Cu Kα radiation.

In some embodiments, crystalline Form B1 is characterized by an XRPD pattern substantially as shown in FIG. 13.

In some embodiments, crystalline Form B1 is characterized by three or more, four or more, five or more, or six or more XRPD peaks listed in Table 11 below.

TABLE 11

XRPD Peaks for Crystalline Form B1

| Pos. [°2Th.] | d-spacing [Å] | Rel. Int. [%] |
|---|---|---|
| 8.01 | 11.03 | 11.74 |
| 12.90 | 6.86 | 12.61 |
| 14.48 | 6.12 | 11.39 |
| 16.05 | 5.52 | 100.00 |
| 16.66 | 5.32 | 30.88 |
| 17.10 | 5.19 | 41.89 |
| 18.04 | 4.92 | 25.85 |
| 19.93 | 4.45 | 18.66 |
| 20.67 | 4.30 | 33.18 |
| 22.12 | 4.02 | 26.81 |
| 22.57 | 3.94 | 26.19 |
| 23.25 | 3.83 | 8.24 |
| 24.17 | 3.68 | 37.94 |
| 24.74 | 3.60 | 56.78 |
| 25.74 | 3.46 | 10.79 |
| 27.38 | 3.26 | 5.60 |

In some embodiments, crystalline Form B1 is characterized by an endothermic peak at from about 156° C. to about 166° C., or from about 159° C. to about 163° C., or from about 160° C. to about 162° C., as determined by DSC. In some embodiments, crystalline Form B1 is characterized by an endothermic peak at about 161.2° C., as determined by DSC.

In some embodiments, crystalline Form B1 is characterized by a DSC profile substantially as shown in FIG. 14.

In some embodiments, crystalline Form B1 is characterized by from an about 1.0 wt % to an about 2.0 wt % loss between room temperature and about 120° C. In some embodiments, crystalline Form B1 is characterized by from an about 1.2 wt % to an about 1.8 wt % loss between room temperature and about 120° C. In some embodiments, crystalline Form B1 is characterized by an about 1.58 wt % loss between room temperature and about 120° C.

In some embodiments, crystalline Form B1 is characterized by a TGA profile substantially as shown in FIG. 14.

In some embodiments, crystalline Form B1 is characterized by at least two of the following: a) an XRPD pattern as shown in FIG. 13; b) a DSC profile as shown in FIG. 14; or c) a TGA profile as shown in FIG. 14.

In some embodiments, crystalline Form B1 is substantially free of other polymorphic forms. In some embodiments, crystalline Form B1 has a polymorphic purity of at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%.

In another aspect, the present disclosure relates to a mixture comprising crystalline Form B1 and a second solid state form of a compound of Formula (III). In some embodiments, the second solid state form of a compound of Formula (III) is crystalline Form A1.

In some embodiments, the present disclosure relates to a mixture comprising a majority of crystalline Form B1 as compared to other solid state forms of a compound of Formula (III).

III. Pharmaceutical Compositions

Solid state forms of the compound of Formula (I), 6-(4-cyclopropyl-6-methoxypyrimidin-5-yl)-1-(4-(1-isopropyl-4-(trifluoromethyl)-1H-imidazol-2-yl)benzyl)-1H-pyrazolo [3,4-d]pyrimidine of Formula (II), and 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III), as disclosed herein, and mixtures thereof, can be administered to a mammal in the form of a raw chemical without any other components present, or Compounds of the Disclosure can also be administered to a mammal as part of a pharmaceutical composition containing the compound combined with a suitable pharmaceutically acceptable carrier (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Standard pharmaceutical carriers and their formulations are described in Remington's Pharmaceutical Sciences, Mack Publishing Co., Easton, Pa., 19th ed. 1995.

Solid state forms of the compound of Formula (I), the compound of Formula (II), and the compound of Formula (III), as disclosed herein, and mixtures thereof, may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form A of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form C of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form D of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form E of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form F of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 1 of the hydrochloric acid salt of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 2 of the gentisic acid co-crystal of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 3 of the hydrochloric acid salt of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 4 of the hydrobromic acid salt of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 5 of the hydrobromic acid salt of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 6 of the ethanedisulfonic acid salt of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 7 of the methanesulfonic acid salt of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 8 of the benzoic acid cocrystal of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form 9 of the salicylic acid cocrystal of the compound of Formula (II) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form A1 of the compound of Formula (III) may be administered to subjects via the oral, parenteral (such as subcutaneous, intravenous, intramuscular, intrasternal and infusion techniques), rectal, intranasal, topical or transdermal (e.g., through the use of a patch) routes.

In some embodiments, crystalline Form B1 of the compound of Formula (III) may be administered to subjects via the oral, parenteral (such as subcutaneous, intravenous, intramuscular, intrasternal and infusion techniques), rectal, intranasal, topical or transdermal (e.g., through the use of a patch) routes.

In another aspect, the present disclosure relates to a solid dosage form comprising one or more of the solid state forms of the compound of Formula (I), the compound of Formula (II), and the compound of Formula (III), as disclosed herein, and one or more pharmaceutically acceptable carriers or diluents. Solid dosage forms can include, but are not limited to, tablets, capsules, pills, granules, powders, sachets, chewables, and films.

In some embodiments, the present disclosure provides a solid dosage form comprising a compound of Formula (I), a compound of Formula (II), or a compound for Formula (III), or a pharmaceutically acceptable salt or solvate thereof, wherein the solid dosage form is for use in a method for treating cancer.

In another aspect, the present disclosure relates to a pharmaceutical composition comprising one or more of the solid state forms of the compound of Formula (I), the compound of Formula (II), and the compound of Formula (III), as disclosed herein, and one or more pharmaceutically acceptable carriers or diluents.

In some embodiments, the pharmaceutical composition comprises crystalline Form A of the compound of Formula (II). In some embodiments, the pharmaceutical composition comprises crystalline Form C of the compound of Formula (II). In some embodiments, the pharmaceutical composition comprises crystalline Form D of the compound of Formula (II). In some embodiments, the pharmaceutical composition comprises crystalline Form E of the compound of Formula (II). In some embodiments, the pharmaceutical composition comprises crystalline Form F of the compound of Formula (II).

In some embodiments, the pharmaceutical composition comprises crystalline Form 1 of the hydrochloric acid salt of the compound of Formula (II). In some embodiments, the pharmaceutical composition comprises crystalline Form 2 of the gentisic acid co-crystal of the compound of Formula (II). In some embodiments, the pharmaceutical composition comprises crystalline Form 3 of the hydrochloric acid salt of the compound of Formula (II). In some embodiments, the pharmaceutical composition comprises crystalline Form 4 of the hydrobromic acid salt of the compound of Formula (II). In some embodiments, the pharmaceutical composition comprises crystalline Form 5 of the hydrobromic acid salt of the compound of Formula (II). In some embodiments, the pharmaceutical composition comprises crystalline Form 6 of the ethanedisulfonic acid salt of the compound of Formula (II). In some embodiments, the pharmaceutical composition comprises crystalline Form 7 of the methanesulfonic acid salt of the compound of Formula (II). In some embodiments, the pharmaceutical composition comprises crystalline Form 8 of the benzoic acid cocrystal of the compound of Formula (II). In some embodiments, the pharmaceutical composition comprises crystalline Form 9 of the salicylic acid cocrystal of the compound of Formula (II). In some embodiments, the pharmaceutical composition comprises an amorphous form of the compound of Formula (II).

In some embodiments, the pharmaceutical composition comprises a mixture of two or more solid state forms of the compound of Formula (II).

In some embodiments, the pharmaceutical composition comprises crystalline Form A1 of the compound of Formula (III). In some embodiments, the pharmaceutical composition comprises crystalline Form B1 of the compound of Formula (III). In some embodiments, the pharmaceutical composition comprises an amorphous form of the compound of Formula (III).

In some embodiments, the pharmaceutical composition comprises a mixture of two or more solid state forms of the compound of Formula (III).

In some embodiments, the pharmaceutical composition is an orally acceptable dosage form comprising one or more of crystalline Forms A, C, D, E, F, 1, 2, 3, 4, 5, 6, 7, 8, and 9 and amorphous form of a compound of Formula (II).

In some embodiments, the pharmaceutical composition is an orally acceptable dosage form comprising one or more of crystalline Forms A1 and B1, and amorphous form of a compound of Formula (III).

In some embodiments, the orally acceptable dosage form can include, but is not limited to, capsules, tablets, aqueous suspensions, and solutions.

For oral administration, known carriers can be included in the pharmaceutical composition. For example, microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia, can be included in a tablet. Additionally, lubricating agents such as magnesium stearate, sodium lauryl sulfate and talc are often useful for tableting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

In some embodiments, the pharmaceutical composition is a parenteral formulation comprising one or more of crystalline Forms A, C, D, E, F, 1, 2, 3, 4, 5, 6, 7, 8, and 9 and amorphous form of a compound of Formula (II).

In some embodiments, the pharmaceutical composition is a parenteral formulation comprising one or more of crystalline Forms A1 and B1, and amorphous form of a compound of Formula (III).

For parenteral administration, solutions containing a solid state form of a compound of Formula (I), a compound of Formula (II), or a compound of Formula (III) can be prepared in either sesame or peanut oil, in aqueous propylene glycol, or in sterile water or saline. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

In some embodiments, the pharmaceutical composition may be prepared as liquid suspension or solution using a liquid, such as an oil, water, an alcohol, and combinations of these.

In some embodiments, the pharmaceutical composition may be prepared as a sterile injectable, which may be aqueous or oleaginous suspensions. These suspensions may be formulated according to techniques known in the art.

In some embodiments, the pharmaceutical composition may be administered in the form of suppositories for rectal administration.

In some embodiments, the pharmaceutical composition may also be administered topically, especially when the target of treatment includes areas or organs readily accessible by topical application, including diseases of the eye, the skin, or the lower intestinal tract. Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment, lotion, or cream containing the active component suspended or dissolved in one or more carriers.

In some embodiments, the pharmaceutical composition may also be administered ophthalmically and formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

In some embodiments, the pharmaceutical composition may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, the pharmaceutical compositions to be used for in vivo administration can be sterile. This is readily accomplished by filtration through, e.g., sterile filtration membranes.

Pharmaceutical compositions within the scope of the present disclosure include all compositions where a solid state form of a compound of Formula (I), a compound of Formula (II), or a compound for Formula (III) is combined with one or more pharmaceutically acceptable carriers or diluents. In one embodiment, a solid state form of the compound of Formula (I), the compound of Formula (II), or the compound for Formula (III) is present in the composition in an amount that is effective to achieve its intended therapeutic purpose.

Pharmaceutical compositions of the present disclosure can be administered to any patient that may experience the beneficial effects of a solid state form of a compound of Formula (I), a compound of Formula (II), or a compound for Formula (III). Foremost among such patients are mammals, e.g., humans and companion animals, although the disclosure is not intended to be so limited. In one embodiment, the patient is a human.

In another aspect, the present disclosure relates to kits which comprise a solid state form of a compound of Formula (I), a compound of Formula (II), or a compound for Formula (III) packaged in a manner that facilitates their use to practice methods of the present disclosure. In one embodiment, the kit includes a solid state form of a compound of Formula (I), a compound of Formula (II), or a compound for Formula (III) (or a composition thereof) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration. In some embodiments, the present disclosure provides a kit which comprises a solid state form of a compound of Formula (I), a compound of Formula (II), or a compound for Formula (III), or a pharmaceutically acceptable salt or solvate thereof, and instructions for administering the compound, or a pharmaceutically acceptable salt or solvate thereof, to a patient having cancer.

In some embodiments, the present disclosure provides a pharmaceutical composition comprising a solid state form of a compound of Formula (I), a compound of Formula (II), or a compound for Formula (III), or a pharmaceutically acceptable salt or solvate thereof, and a pharmaceutically acceptable carrier or diluent, wherein the pharmaceutical composition is for use in a method for treating cancer.

IV. Methods of Treatment

Solid state forms of the compound of Formula (I), 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II), and 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III), as disclosed herein, and mixtures thereof, may be used to inhibit the activity of a USP1 protein. For example, in some embodiments, a method of inhibiting a USP1 protein comprises contacting the USP1 protein with a solid state form of a compound of Formula (I), a compound of Formula (II), a compound of Formula (III), or combinations thereof. The contacting can occur in vitro or in vivo.

In some embodiments, a solid state form of a compound of Formula (I), a compound of Formula (II), or a compound of Formula (III) can be used to treat a "USP1 protein mediated disorder." A USP1 protein mediated disorder is any pathological condition in which a USP1 protein is known to play a role. In some embodiments, a USP1 protein mediated disorder is a proliferative disease such as cancer.

Various methods of treating diseases and disorders with the solid state forms of a compound of Formula (I), a compound of Formula (II), or a compound of Formula (III) are provided herein. Exemplary diseases and disorders that may be treated with the solid state forms include, but are not limited to, cancer.

In some embodiments, methods of treating cancer with the solid state forms of a compound of Formula (I), a compound of Formula (II), or a compound of Formula (III) are provided. Such methods comprise administering to a subject with cancer a therapeutically effective amount of a Compound of a solid state form of a compound of Formula (I), a compound of Formula (II), or a compound of Formula (III).

In some embodiments, the cancer to be treated with a solid state form disclosed herein is selected from a hematological cancer, a lymphatic cancer, and a DNA repair pathway deficient cancer. In some embodiments, the cancer to be treated is a cancer that comprises cancer cells with a mutation in a gene encoding p53. In some embodiments, the cancer to be treated is a cancer that comprises cancer cells with a loss of function mutation in a gene encoding p53.

In some embodiments, the cancer to be treated with a solid state form disclosed herein is selected from non-small cell lung cancer (NSCLC), osteosarcoma, ovarian cancer, and breast cancer. In some embodiments, the cancer is ovarian cancer or breast cancer. In some embodiments, the cancer is ovarian cancer. In some embodiments, the cancer is breast cancer. In some embodiments, the cancer is a triple negative breast cancer.

In some embodiments, the cancer to be treated with a solid state form disclosed herein is selected from the group consisting of bone cancer, including osteosarcoma and chondrosarcoma; brain cancer, including glioma, glioblastoma, astrocytoma, medulloblastoma, and meningioma; soft tissue cancer, including rhabdoid and sarcoma; kidney cancer; bladder cancer; skin cancer, including melanoma; and lung cancer, including non-small cell lung cancer.

In some embodiments, the present disclosure provides a method for treating cancer comprising administering one or more of the solid state forms disclosed herein to a patient in need thereof. In some embodiments, the present disclosure provides a method for treating cancer comprising administering one or more of the pharmaceutical compositions disclosed herein to a patient in need thereof. In some embodiments, the present disclosure provides a method for treating cancer comprising administering one or more of the solid dosage forms disclosed herein to a patient in need thereof.

In some embodiments, the present disclosure provides a method for treating cancer comprising administering to a patient in need thereof a solid state form as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof. In some embodiments, the present disclosure provides a method for treating cancer comprising administering to a patient in need thereof crystalline Form A. In some embodiments, the present disclosure provides a method for treating cancer comprising administering to a patient in need thereof crystalline Form F. In some embodiments, the present disclosure provides a method for treating cancer comprising administering to a patient in need thereof crystalline Form 1. In some embodiments, the present disclosure provides a method for treating cancer comprising administering to a patient in need thereof crystalline Form 2. In some embodiments, the present disclosure provides a method for treating cancer comprising administering to a patient in need thereof crystalline Form 8. In some embodiments, the present disclosure provides a method for treating cancer comprising administering to a patient in need thereof crystalline Form 9. In some embodiments, the present disclosure provides a method for treating cancer comprising administering to a patient in need thereof crystalline Form A1. In some embodiments, the present disclosure provides a method for treating cancer comprising administering to a patient in need thereof crystalline Form B1.

In some embodiments, the present disclosure provides a method for treating breast cancer comprising administering to a patient in need thereof a solid state form as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof. In some embodiments, the present disclosure provides a method for treating breast cancer comprising administering to a patient in need thereof crystalline Form A. In some embodiments, the present disclosure provides a method for treating breast cancer comprising administering to a patient in need thereof crystalline Form F. In some embodiments, the present disclosure provides a method for treating breast cancer comprising administering to a patient in need thereof crystalline Form 1. In some embodiments, the present disclosure provides a method for treating breast cancer comprising administering to a patient in need thereof crystalline Form 2. In some embodiments, the present disclosure provides a method for treating breast cancer comprising administering to a patient in need thereof crystalline Form 8. In some embodiments, the present disclosure provides a method for treating breast cancer comprising administering to a patient in need thereof crystalline Form 9. In some embodiments, the present disclosure provides a method for treating breast cancer comprising administering to a patient in need thereof crystalline Form A1. In some embodiments, the present disclosure provides a method for treating breast cancer comprising administering to a patient in need thereof crystalline Form B1.

In some embodiments, the present disclosure provides a method for treating ovarian cancer comprising administering to a patient in need thereof a solid state form as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof. In some embodiments, the present disclosure provides a method for treating ovarian cancer comprising administering to a patient in need thereof crystalline Form A. In some embodiments, the present disclosure provides a method for treating ovarian cancer comprising administering to a patient in need thereof crystalline Form F. In some embodiments, the present disclosure provides a method for treating ovarian cancer comprising administering to a patient in need thereof crystalline Form 1. In some embodiments, the present disclosure provides a method for treating ovarian cancer comprising administering to a patient in need thereof crystalline Form 2. In some embodiments, the present disclosure provides a method for treating ovarian cancer comprising administering to a patient in need thereof crystalline Form 8. In some embodiments, the present disclosure provides a method for treating ovarian cancer comprising administering to a patient in need thereof crystalline Form 9. In some embodiments, the present disclosure provides a method for treating ovarian cancer comprising administering to a patient in need thereof crystalline Form A1. In some embodiments, the present disclosure provides a method for treating ovarian cancer comprising administering to a patient in need thereof crystalline Form B1.

Various methods of treating cancer with a compound of Formula (I), a compound of Formula (II), or a compound of Formula (III) are provided herein. In some embodiments, a therapeutically effective amount of a compound of Formula (I), a compound of Formula (II), or a compound of Formula (III) is administered to a subject with cancer, wherein the cancer comprises cancer cells with elevated levels of RAD18. In some embodiments, the elevated levels of RAD18 are elevated RAD18 protein levels. In some embodiments, the elevated levels of RAD18 are elevated RAD18 mRNA levels. In some embodiments, elevated levels of RAD18 (e.g., RAD18 protein and/or RAD18 mRNA) have been detected (e.g., in a cancer sample obtained from the subject) prior to the administration. That is, in some embodiments, a subject's cancer has been tested for RAD18 protein or mRNA prior to beginning treatment with a USP1 inhibitor.

In some embodiments, such methods for treating cancer comprise (a) identifying a cancer in a subject as a USP1 inhibitor-sensitive cancer and then (b) administering a therapeutically effective amount of a solid state form of a compound of Formula (I), a compound of Formula (II), or a compound of Formula (III) to the subject.

In some embodiments, such methods comprise (a) detecting levels of RAD18 (e.g., RAD18 protein and/or RAD18 mRNA) in cancer cells (e.g., in a cancer sample obtained from the subject) and then (b) administering a therapeutically effective amount of a compound of Formula (I), a compound of Formula (II), or a compound of Formula (III) to a subject having a cancer comprising cells with elevated levels of RAD18.

In some embodiments, such methods comprise administering to a subject with triple negative breast cancer a therapeutically effective amount of a compound of Formula (I), a compound of Formula (II), or a compound of Formula (III).

In some embodiments, a compound of Formula (I), a compound of Formula (II), or a compound of Formula (III) is used to treat a cancer, wherein the cancer is a homologous-recombination deficient cancer. In some embodiments, a compound of Formula (I), a compound of Formula (II), or a compound of Formula (III) is used to treat a cancer, wherein the cancer comprises cancer cells with a mutation in a gene encoding p53. In some embodiments, a compound of Formula (I), a compound of Formula (II), or a compound of Formula (III) is used to treat a cancer, wherein the cancer comprises cancer cells with a loss of function mutation in a gene encoding p53. In some embodiments, a compound of Formula (I), a compound of Formula (II), or a compound of Formula (III) is used to treat a cancer that does not have a defect in the homologous recombination pathway.

In some embodiments, a compound of Formula (I), a compound of Formula (II), or a compound of Formula (III) is used to treat a cancer, wherein the cancer is a BRCA1 mutant cancer. In some embodiments, a compound of Formula (I), a compound of Formula (II), or a compound of Formula (III) is used to treat a cancer, wherein the cancer is a BRCA2 mutant cancer. In some embodiments, a compound of Formula (I), a compound of Formula (II), or a compound of Formula (III) is used to treat a cancer, wherein the cancer is a BRCA1 mutant cancer and a BRCA2 mutant cancer. In some embodiments, the cancer is not a BRCA1 mutant cancer or a BRCA2 mutant cancer. In some embodiments, the cancer is a BRCA1 deficient cancer. In some embodiments, the cancer is a BRCA2 deficient cancer. In some embodiments, the cancer is a BRCA1 deficient cancer and a BRCA2 mutant cancer.

In some embodiments, a compound of Formula (I), a compound of Formula (II), or a compound of Formula (III) is used to treat a cancer, wherein the cancer is a PARP inhibitor resistant cancer. In some embodiments, a compound of Formula (I), a compound of Formula (II), or a compound of Formula (III) is used to treat a cancer, wherein the cancer is a PARP inhibitor resistant BRCA1-deficient cancer.

In some embodiments, the cancer is a BRCA1 and/or BRCA2 mutant cancer, wherein the cancer comprises cells with elevated levels of RAD18, e.g., wherein the elevated levels of RAD18 are at least as high as the RAD18 protein and/or mRNA levels in ES2 cells or wherein the elevated levels of RAD18 are higher than the RAD18 protein and/or mRNA levels in HEP3B217 cells. In some embodiments, a triple negative breast cancer is a BRCA1 and/or BRCA2 mutant cancer.

In some instances, the cancer is a solid cancer. In some instances, the cancer is a hematological/lymphatic cancer. In some instances, the cancer is a DNA repair pathway deficient cancer. In some instances, the cancer is a homologous-recombination deficient cancer. In some instances, the cancer comprises cancer cells with a mutation in a gene encoding p53. In some instances, the cancer comprises cancer cells with a loss of function mutation in a gene encoding p53. In some instances, the cancer is selected from the group consisting of non-small cell lung cancer (NSCLC), osteosarcoma, ovarian cancer, and breast cancer (including triple negative breast cancer). In some instances, the cancer is ovarian cancer or breast cancer (including triple negative breast cancer). In some instances, the cancer is ovarian cancer. In some instances, the cancer is breast cancer (including triple negative breast cancer).

In some embodiments, a compound of Formula (I), a compound of Formula (II), or a compound of Formula (III) is used in combination with one or more additional therapeutic agents to treat cancer. It has been reported that p53 status determines PARP inhibitor sensitization by ionizing radiation in multiple BRCA1 and HR-proficient tumor types (Sizemore et al., *Mol. Cancer Res.* 16: 1092-1102 (2018)). As shown below, p53 mutant cancers and BRCA mutant cancers have increased sensitivity to USP1 inhibitors. Accordingly, in some embodiments, a compound of Formula (I), a compound of Formula (II), or a compound of Formula (III) is used in combination with a PARP inhibitor to treat cancer.

In some embodiments, the present disclosure provides a use of one or more of the solid state forms disclosed herein for the manufacture of a medicament for treating cancer. In some embodiments, the present disclosure provides a use of one or more of the pharmaceutical compositions disclosed herein for the manufacture of a medicament for treating cancer. In some embodiments, the present disclosure provides a use of one or more of the solid dosage forms disclosed herein for the manufacture of a medicament for treating cancer.

In some embodiments, the present disclosure provides a use of one or more solid state forms as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof, for the manufacture of a medicament for treating cancer. In some embodiments, the present disclosure provides a use of crystalline Form A for the manufacture of a medicament for treating cancer. In some embodiments, the present disclosure provides a use of crystalline Form F for the manufacture of a medicament for treating cancer. In some embodiments, the present disclosure provides a use of crystalline Form 1 for the manufacture of a medicament for treating cancer. In some embodiments, the present disclosure provides a use of crystalline Form 2 for the manufacture of a medicament for treating cancer. In some embodiments, the present disclosure provides a use of crystalline Form 8 for the manufacture of a medicament for treating cancer. In some embodiments, the present disclosure provides a use of crystalline Form 9 for the manufacture of a medicament for treating cancer. In some embodiments, the present disclosure provides a use of crystalline Form A1 for the manufacture of a medicament for treating cancer. In some embodiments, the present disclosure provides a use of crystalline Form B1 for the manufacture of a medicament for treating cancer.

In some embodiments, the present disclosure provides a use of one or more solid state forms as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof, for the manufacture of a medicament for treating breast cancer. In some embodiments, the present disclosure provides a use of crystalline Form A for the manufacture of a medicament for treating breast cancer. In some embodiments, the present disclosure provides a use of crystalline Form F for the manufacture of a medicament for treating breast cancer. In some embodiments, the present disclosure provides a use of crystalline Form 1 for the manufacture of a medicament for treating breast cancer. In some embodiments, the present disclosure provides a use of crystalline Form 2 for the manufacture of a medicament for treating breast cancer. In some embodiments, the present disclosure provides a use of crystalline Form 8 for the manufacture of a medicament for treating breast cancer. In some embodiments, the present disclosure provides a use of crystalline Form 9 for the manufacture of a medicament for treating breast cancer. In some embodiments, the present disclosure provides a use of crystalline Form A1 for the manufacture of a medicament for treating breast cancer. In some embodiments, the present disclosure provides a use of crystalline Form B1 for the manufacture of a medicament for treating breast cancer.

In some embodiments, the present disclosure provides a use of one or more solid state forms as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof, for the manufacture of a medicament for treating ovarian cancer. In some embodiments, the present disclosure provides a use of crystalline Form A for the manufacture of a medicament for treating ovarian cancer. In some embodiments, the present disclosure provides a use of crystalline Form F for the manufacture of a medicament for treating ovarian cancer. In some embodiments, the present disclosure provides a use of crystalline Form 1 for the manufacture of a medicament for treating ovarian cancer. In some embodiments, the present disclosure provides a use of crystalline Form 2 for the manufacture of a medicament for treating ovarian cancer. In some embodiments, the present disclosure provides a use of crystalline Form 8 for the manufacture of a medicament for treating ovarian cancer. In some embodiments, the present disclosure provides a use of crystalline Form 9 for the manufacture of a medicament for treating ovarian cancer. In some embodiments, the present disclosure provides a use of crystalline Form A1 for the manufacture of a medicament for treating ovarian cancer. In some embodiments, the present disclosure provides a use of crystalline Form B1 for the manufacture of a medicament for treating ovarian cancer.

In some embodiments, the present disclosure provides a solid state form of a compound of Formula (I), a compound of Formula (II), or a compound for Formula (III), or a pharmaceutically acceptable salt or solvate thereof, wherein the solid state form is for use in a method for treating cancer.

In some embodiments, the present disclosure provides a solid state forms as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof, for use in a method for treating cancer. In some embodiments, the present disclosure provides crystalline Form A for use in a method for treating cancer. In some embodiments, the present disclosure provides crystalline Form F for use in a method for treating cancer. In some embodiments, the present disclosure provides crystalline Form 1 for use in a method for treating cancer. In some embodiments, the present disclosure provides crystalline Form 2 for use in a method for treating cancer. In some embodiments, the present disclosure provides crystalline Form 8 for use in a method for treating cancer. In some embodiments, the present disclosure provides crystalline Form 9 for use in a method for treating cancer. In some embodiments, the present disclosure provides crystalline Form A1 for use in a method for treating cancer. In some embodiments, the present disclosure provides crystalline Form B1 for use in a method for treating cancer.

In some embodiments, the present disclosure provides a solid state forms as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9 crystalline Form A1, crystalline Form B1, and mixtures thereof, for use in a method for treating breast cancer. In some embodiments, the present disclosure provides crystalline Form A for use in a method for treating breast cancer. In some embodiments, the present disclosure provides crystalline Form F for use in a method for treating breast cancer. In some embodiments, the present disclosure provides crystalline Form 1 for use in a method for treating breast cancer. In some embodiments, the present disclosure provides crystalline Form 2 for use in a method for treating breast cancer. In some embodiments, the present disclosure provides crystalline Form 8 for use in a method for treating breast cancer. In some embodiments, the present disclosure provides crystalline Form 9 for use in a method for treating breast cancer. In some embodiments, the present disclosure provides crystalline Form A1 for use in a method for treating breast cancer. In some embodiments, the present disclosure provides crystalline Form B1 for use in a method for treating breast cancer.

In some embodiments, the present disclosure provides a solid state forms as disclosed herein, or a pharmaceutically acceptable salt thereof, selected from the group consisting of crystalline Form A, crystalline Form C, crystalline Form D, crystalline Form E, crystalline Form F, crystalline Form 1, crystalline Form 2, crystalline Form 3, crystalline Form 4, crystalline Form 5, crystalline Form 6, crystalline Form 7, crystalline Form 8, crystalline Form 9, crystalline Form A1, crystalline Form B1, and mixtures thereof, for use in a method for treating ovarian cancer. In some embodiments, the present disclosure provides crystalline Form A for use in a method for treating ovarian cancer. In some embodiments, the present disclosure provides crystalline Form F for use in a method for treating ovarian cancer. In some embodiments, the present disclosure provides crystalline Form 1 for use in a method for treating ovarian cancer. In some embodiments, the present disclosure provides crystalline Form 2 for use in a method for treating ovarian cancer. In some embodiments, the present disclosure provides crystalline Form 8 for use in a method for treating ovarian cancer. In some embodiments, the present disclosure provides crystalline Form 9 for use in a method for treating ovarian cancer. In some embodiments, the present disclosure provides crystalline Form A1 for use in a method for treating ovarian cancer. In some embodiments, the present disclosure provides crystalline Form B1 for use in a method for treating ovarian cancer.

V. Methods of Preparation

In one aspect, the present disclosure relates to methods for preparing a solid state form of a compound of Formula (I), a compound of Formula (II), or a compound of Formula (III).

In some embodiments, the method comprises:
a) adding a suitable amount of a compound of Formula (I), a compound of Formula (II), or a compound of Formula (III) to a suitable amount of a suitable solvent system to obtain a suspension;
b) stirring the suspension; and
c) collecting the solid product from step b).

In some embodiments, a suitable pharmaceutically acceptable acid is added during step a).

In some embodiments, the suitable solvent system is selected from the group consisting of acetonitrile, acetone, cyclohexane, dichloromethane, dimethylacetamide, dimethyl sulfoxide, ethanol, ethyl acetate, isopropyl alcohol, isopropyl acetate, methanol, methyl ethyl ketone, 4-methyl-2-pentanone, methyl tert-butyl ether, 2-methyl tetrahydrofuran, n-heptane, n-methyl pyrrolidone, tetrahydrofuran, toluene, water, and mixtures thereof. In some embodiments, the suitable solvent system is selected from the group consisting of ethyl acetate, n-heptane, and mixtures thereof.

In some embodiments, the method comprises:
a) dissolving a suitable amount of a compound of Formula (I), a compound of Formula (II), or a compound of Formula (III) in a suitable amount of a suitable solvent to make a solution;
b) adding a suitable amount of a suitable anti-solvent;
c) adding seed crystals of a solid state form of a compound of Formula (I), a compound of Formula (II), or a compound of Formula (III);
d) stirring the resulting suspension; and
e) collecting the solid product produced from step d).

In some embodiments, the method further comprises adding a suitable pharmaceutically acceptable acid during step a).

In some embodiments, the method further comprises adding a suitable anti-solvent after step c) and before step d).

In some embodiments, the suitable solvent and anti-solvent are selected from the group consisting of acetonitrile, acetone, cyclohexane, dichloromethane, dimethylacetamide, dimethyl sulfoxide, ethanol, ethyl acetate, isopropyl alcohol, isopropyl acetate, methanol, methyl ethyl ketone, 4-methyl-2-pentanone, methyl tert-butyl ether, 2-methyl tetrahydrofuran, n-heptane, n-methyl pyrrolidone, tetrahydrofuran, toluene, water, and mixtures thereof. In some embodiments, the suitable solvent and anti-solvent are selected from the group consisting of ethyl acetate, n-heptane, and mixtures thereof. In some embodiments, the suitable solvent is ethyl acetate. In some embodiments, the suitable anti-solvent is n-heptane.

In some embodiments, the compound of Formula (I), the compound of Formula (II), or the compound of Formula (III) is added to the suitable solvent system at a temperature of from about room temperature to about 100° C., or from about room temperature to about 75° C., or from about room temperature to about 50° C., or from about room temperature to about 40° C. In some embodiments, the compound of Formula (I), the compound of Formula (II), or the compound of Formula (III) is added to the suitable solvent system at about room temperature.

In some embodiments, the present disclosure relates to a method for preparing crystalline Form 2 of a gentisic acid co-crystal of a compound of Formula (II), the method comprising:
a) adding a suitable amount of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine and gentisic acid to a suitable amount of a suitable solvent system at room temperature to obtain a suspension;
b) stirring the suspension from step a); and
c) collecting the solid product from step b).

In some embodiments, the suitable solvent system is selected from the group consisting of ethyl acetate, n-heptane, and mixtures thereof.

In some embodiments, the present disclosure relates to a method for preparing crystalline Form 2 of a gentisic acid co-crystal of a compound of Formula (II), the method comprising:
a) dissolving a suitable amount of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine and gentisic acid in a suitable amount of a suitable solvent at room temperature to make a solution;
b) adding a suitable amount of a suitable anti-solvent;
c) adding seed crystals of crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II);
d) stirring the resulting suspension; and
e) collecting the solid product produced from step d).

In some embodiments, the method further comprises adding a suitable anti-solvent after step c) and before step d).

In some embodiments, the suitable solvent is ethyl acetate. In some embodiments, the suitable anti-solvent is n-heptane.

In one aspect, the present disclosure relates to Crystalline Form A of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form C of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form D of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form E of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect the present disclosure related to Crystalline Form F of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form 1 of a hydrochloric acid salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form 8 of a benzoic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form 9 of a salicylic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) prepared by any of the methods disclosed herein.

In another aspect, the present disclosure relates to Crystalline Form A1 of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) prepared by any of the methods disclosed herein.

In another aspect, the present disclosure relates to Crystalline Form B1 of 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) prepared by any of the methods disclosed herein.

EXAMPLES

A. Abbreviations and Acronyms

| | |
|---|---|
| XRPD | X-ray Powder Diffraction |
| PLM | Polarized Light Microscopy |
| TGA | Thermogravimetric Analysis |
| DSC | Differential Scanning Calorimetry |
| S/AS | Solvent/Anti-solvent |
| RT | Room/ambient Temperature |

-continued

| | |
|---|---|
| RH | Relative Humidity |
| ACN | Acetonitrile |
| CHCl3 | Chloroform |
| DCM | Dichloromethane |
| DMAc | N,N-dimethylacetamide |
| DMSO | Dimethyl sulfoxide |
| EtOAc | Ethyl acetate |
| EtOH | Ethanol |
| H2O | Water |
| IPA | Isopropyl alcohol |
| IPAc | Isopropyl acetate |
| MeOH | Methanol |
| MEK | Methyl ethyl ketone |
| MIBK | 4-methyl-2-pentanone (methyl-iso-butyl ketone) |
| MTBE | Methyl-tert-butyl ether |
| NMP | N-methyl-2-pyrrolidone |
| THF | Tetrahydrofuran |
| 2-MeTHF | 2-Methyltetrahydrofuran |
| $C_{max}$ | Maximum observed plasma concentration |
| $T_{max}$ | Time to reach $C_{max}$ |
| $AUC_{last}$ | Area under plasma concentration-time curve from time zero to time of last measurable concentration |
| $T_{1/2}$ | Half-life |
| NOD/SCID | Mice homozygous for the severe combined immune deficiency spontaneous mutation $Prkdc^{scid}$ |

B. Experimental Methods

Instrumental Conditions

X-ray powder diffraction (XRPD) patterns were measured on an X'Pert 3 X-ray powder diffractometer using Cu-kα radiation. Each sample was spread on the middle of a zero-background silicon holder. The tube voltage and amperage were set to 45 kV and 40 mA, respectively. A two-theta (2θ°) continuous scan at 46.7 seconds/step from 3° to 40° 2θ was used. XRPD analysis conditions are shown in the table below.

| Parameters | Reflection Mode |
|---|---|
| Model | X' Pert3 |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | ⅛° |
| Scan mode | Continuous |
| Scan range (°2TH) | 3°-40° |
| Scan step time (s) | 46.7 |
| Step size (°2TH) | 0.0263 |
| Test time | 5 min 4 s |

For the characterization of crystalline Form F, XRPD patterns were measured on an PANanlytical & Xpert³ X-ray powder diffractometer using Cu-kα radiation. Each sample was spread on the middle of a zero-background silicon holder. The tube voltage and amperage were set to 45 kV and 40 mA, respectively. A two-theta (2θ°) continuous scan at 20.96 seconds/step from 2° to 50° 2θ was used. XRPD analysis conditions are shown in the table below.

| Parameters | Reflection Mode |
|---|---|
| Model | PANalytical X' Pert³ |
| X-Ray wavelength | Cu, kα, Kα1 (Å): 1.54060, Kα2 (Å): 1.54443 Kα2/Kα1 intensity ratio: 0.50 |
| X-Ray tube setting | 45 kV, 40 mA |
| Divergence slit | 0.2177° |
| Scan mode | Continuous |
| Scan range (°2TH) | 2°-50° |
| Scan step time (s) | 20.9550 |
| Step size (°2TH) | 0.0167 |

Thermogravimetric analysis (TGA) data was collected using a TA Q5000 and Discovery TGA 5500 TGA from TA Instruments. TGA analysis conditions are shown in the table below.

| Parameters | TGA |
|---|---|
| Method | Ramp |
| Sample pan | Aluminum, open |
| Temperature | RT-350° C. |
| Heating rate | 10° C./min |
| Purge gas | $N^2$ |

Differential scanning calorimetry (DSC) data was collected using a TA Q2000 DSC from TA Instruments. DSC analysis conditions are shown in the table below.

| Parameters | DSC |
|---|---|
| Method | Ramp |
| Sample pan | Aluminum, crimped |
| Temperature | 25° C.-300° C. |
| Heating rate | 2, 10, 20° C./min |
| Purge gas | $N^2$ |

For the characterization of crystalline Form F, DSC data was collected using a Perkin Elmer DSC 4000. DSC analysis conditions are shown in the table below.

| Parameters | DSC |
|---|---|
| Method | Ramp |
| Sample pan | Aluminum, crimped |
| Temperature | 25° C.-350° C. |
| Heating rate | 10° C./min |
| Purge gas | $N^2$ |

Polarized light microscopy (PLM) images were captured with a ZEISS Scope A1 microscope.

Example 1: Preparation and Characterization of Crystalline Form A

A. Preparation of the Compound of Formula (II)

6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine was prepared according to the procedures disclosed in U.S. Provisional Patent Application Nos. 62/783,014; 62/799,423; and 62/868,616.

To an ice cooled solution of 6-(4-cyclopropyl-6-methoxypyrimidin-5-yl)-1-(4-(4-(trifluoromethyl)-1H-imidazol-2-yl)benzyl)-1H-pyrazolo[3,4-d]pyrimidine (1 eq) in dimethylformamide (5 mL) was added sodium hydride (60% dispersion in mineral oil) (1.2 eq) portion wise, and the reaction mixture was stirred at same temperature for 10 min. To the resulting reaction mixture was added a 2-iodopropane (1.20 eq) and stirring was continued at room temperature for 16 hours. Progress of the reaction was monitored by thin layer chromatography (TLC) and liquid chromatography-mass spectrometry (LCMS). After completion, the reaction mixture was diluted with water (50 mL) and extracted with ethyl acetate (2×200 mL). The combined organic layer was dried over anhydrous sodium sulfate, filtered, and concentrated under reduced pressure. The crude compounds were purified by preparatory high performance liquid chromatography (HPLC) to afford 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II). The purified compound was then recrystallized in heptane and ethyl acetate using methods known to those skilled in the art.

B. Characterization 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II), obtained as discussed above, was subjected to)(RFD, TGA, and DSC analysis using the conditions discussed above. The resulting XRPD pattern, DSC profile, and TGA profile are shown in FIGS. 1-2, respectively, and the XRPD peaks are shown in Table 1, above.

Based on the XRPD pattern shown in FIG. 1 and the XRPD peaks shown in Table 1, as well as the crystal structure and DSC and TGA profiles, 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II), obtained as discussed above, was determined to be a crystalline hydrate and was named crystalline Form A.

C. Crystal Structure Determination

About 2.9 mg of crystalline Form A was added to a 3 mL glass vial with 0.5 mL DCM/n-heptane (1:4, v/v) solvent mixture. The mixture was then shaken by an ultrasonic cleaner to accelerate dissolution. The resulting suspension was filtered and the obtained clear solution was transferred to a clean 4-mL shell vial (44.6 mm×14.65 mm). The shell vial was sealed by a PE-Plug with one pinhole. The shell vial was then placed in a fume hood at room temperature for slow evaporation. After 1 day of slow evaporation, block-like crystals were observed.

A suitable single crystal with good diffraction quality was selected from the block-like crystal samples and was wrapped with Paratone-N (an oil based cryoprotectant). The crystal was mounted on a mylar loop in a random orientation and immersed in a stream of nitrogen at 120 K. Preliminary examination and data collection were performed on a Rigaku XtaLAB Synergy R (CuKα radiation, λ, =1.54184 Å) diffractometer and analyzed with the CrysAlisPro (V1.171.40.19a, Rigaku, 2018) software package. Cell parameters and an orientation matrix for data collection were retrieved and refined (T-vector Dirax algorithm) by CrysAlisPro (V1.171.40.19a, Rigaku, 2018) software using the setting angles of 49260 reflections in the range 3.563°<θ<75.668°. The data were collected to a minimum diffraction angle (θ) of 3.591° and a maximum diffraction angle (θ) of 76.011° at 120 K. The final point group completeness is 100%. The mean I/σ of the data is 69.7 and the highest resolution is truncated at 0.79 Å.

Frames were integrated with CrysAlisPro (V1.171.40.19a, Rigaku, 2018). A total of 57,364 reflections were collected, of which 5292 were unique. Lorentz and polarization corrections were applied to the data. An empirical absorption correction was performed using CrysAlisPro (V1.171.40.19a, Rigaku, 2018) using spherical harmonics implemented in SCALE3 ABSPACK. The absorption coefficient μ of this material is 0.883 mm-1 at this wavelength (λ=1.542 Å) and the minimum and maximum transmissions are 0.94414 and 1.0000, respectively. The agreement factor for the averaging was 5.19% based on intensity.

The structure was solved in the space group $P2_1/c$ with the ShelXT structure solution program using Intrinsic Phasing and refined with ShelXL (Version 2018/3) refinement package using full-matrix least-squares on $F^2$ contained in OLEX2. All non-hydrogen atoms were refined anisotropically. The hydrogen atoms were calculated geometrically and refined using the riding model.

A calculated XRPD pattern was generated for copper ("Cu") radiation using Mercury program and the atomic coordinates, space group, and unit cell parameters from the single crystal structure. Crystal structure representations were generated by Olex2 and Diamond. The atomic thermal displacement ellipsoids drawing was generated by ORTEP-III.

A suitable single crystal was separated from the block-like crystals and selected for single-crystal X-ray diffraction data collection. The crystal system of the single crystal was monoclinic and the space group is $P2_1/c$. Crystallographic data and the refinement parameters are shown in Table 12.

TABLE 12

| Crystallographic data of crystalline Form A | |
|---|---|
| Empirical formula | $C_{27}H_{25}F_3N_8O \cdot 0.42(H_2O)$ |
| Formula weight | 541.75 |
| Temperature | 119.99(10)K |
| Wavelength | CuKα (λ = 1.54184 Å) |
| Crystal system, space group | Monoclinic, $P2_{1/c}$ |
| Unit cell dimensions | a = 12.05400(10) Å |
| | b = 8.77450(10) Å |
| | c = 24.83660(10) Å |
| | α = 90° |
| | β = 97.6260(10)° |
| | γ = 90° |
| Volume | 2603.68(4) Å$^3$ |
| Z, CalMolated density | 4, 1.382 g/cm$^3$ |
| Absorption coefficient | 0.883 mm$^{-1}$ |
| F(000) | 1128.0 |
| Crystal size | 0.12 × 0.11 × 0.1 mm$^3$ |
| 2 Theta range for data collection | 7.182 to 152.022 |
| Limiting indices | −13 ≤ h ≤ 15 |
| | −10 ≤ k ≤ 11 |
| | −31 ≤ l ≤ 31 |
| Reflections collected/ | 57364/5292 [$R_{int}$ = 0.0519, |
| Independent reflections | $R_{sigma}$ = 0.0143] |
| Refinement method | Full-matrix least-squares on $F^2$ |
| Completeness | 100% |
| Data/restraints/parameters | 5292/16/408 |
| Goodness-of-fit on $F^2$ | 1.084 |
| Final R indices [I ≥ 2sigma(I)] | $R_1$ = 0.0463, w$R_2$ = 0.1142 |
| Final R indices [all data] | $R_1$ = 0.0467, w$R_2$ = 0.1144 |
| Largest diff. peak and hole | 0.50/−0.41 e · Å$^{-3}$ |

As shown in FIG. 20, the asymmetric unit of the single crystal structure is comprised of one freebase compound of Formula (II) molecule and a non-integer number of water molecules, which suggested that crystalline Form A is hydrate. The number of water molecule in the asymmetric unit was freely refined to be 0.42, according to the thermal parameters.

Example 2: Preparation and Characterization of Crystalline Form C

A. Preparation

A suitable amount of crystalline Form A of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) was purged with nitrogen gas ($N_2$) for 20 minutes at 30° C. to form a new crystalline form.

B. Characterization

The new crystalline Form was subjected to XRPD analysis using the conditions discussed above. The resulting XRPD pattern is shown in FIG. 3, and the XRPD peaks are shown in Table 2, above. Based on the XRPD pattern shown in FIG. 3 and the XRPD peaks shown in Table 2, the new crystalline form was determined to be an anhydrate and was named crystalline Form C.

Example 3: Preparation and Characterization of Crystalline Form D

A. Preparation

A suitable amount of crystalline Form C of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) was heated to 150° C. under nitrogen gas to form a new crystalline form.

B. Characterization

The new crystalline Form was subjected to XRPD analysis using the conditions discussed above. The resulting XRPD pattern is shown in FIG. 4, and the XRPD peaks are shown in Table 3, above. Based on the XRPD pattern shown in FIG. 4 and the XRPD peaks shown in Table 3, the new crystalline form was determined to be an anhydrate and was named crystalline Form D.

Example 4: Preparation and Characterization of Crystalline Form E

A. Preparation

Approximately 20 mg of crystalline Form A of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) was placed in a 3 mL vial. The 3 mL vial was then placed in a 20 mL vial with approximately 4 mL of DCM. The 20 mL vial was sealed and kept at room temperature for 10 days. After 10 days, the resulting solution was allowed to evaporate at room temperature to obtain solid material.

B. Characterization

The resulting solid material was subjected to XRPD, TGA, and DSC analysis using the conditions discussed above. The resulting XRPD pattern, DSC profile, and TGA profile are shown in FIGS. 5-6, respectively, and the XRPD peaks are shown in Table 4, above.

Based on the XRPD pattern shown in FIG. 5 and the XRPD peaks shown in Table 4, as well as the DSC and TGA profiles, the obtained solid material was determined to be a crystalline DCM solvate and was named crystalline Form E.

Example 5: Preparation and Characterization of Crystalline Form 1

A. Preparation

Approximately 20 mg of crystalline Form A was mixed in a 1:1 ratio with hydrochloric acid in an HPLC vial. 0.5 mL of EtOAc/n-heptane (1:1, v/v) was then added to form a suspension, which was stirred at about 1000 rpm at room temperature for about 3 days. The resulting solid material was isolated by centrifugation and dried under vacuum at room temperature.

B. Characterization

The resulting solid material was subjected to XRPD, TGA, and DSC analysis using the conditions discussed above. The resulting XRPD pattern, DSC profile, and TGA profile are shown in FIGS. 7-8, respectively, and the XRPD peaks are shown in Table 6, above.

Based on the XRPD pattern shown in FIG. 7 and the XRPD peaks shown in Table 6, as well as the DSC and TGA profiles, the obtained solid material was determined to be a crystalline hydrate of an HCl salt of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and was named crystalline Form 1.

Example 6: Preparation and Characterization of Crystalline Form 2

A. Preparation

Method A: Approximately 40 mg of crystalline Form A and 11.6 mg of gentisic acid were combined with 0.5 mL EtOAc/n-Heptane to obtain a suspension. The suspension was stirred at room temperature for 2 days, and the solid material was isolated by vacuum filtration and dried under vacuum at room temperature. The resulting solid material can be used as "seeds" to prepare crystalline Form 1 at larger scales.

Method B: Approximately 500 mg of crystalline Form A and 11.6 mg of gentisic acid were combined with 7 mL EtOAc to obtain a solution. 5.0 mL n-heptane was then added dropwise, along with 10.2 mg of gentisic acid co-crystal "seeds" prepared according to method A, and finally 8.0 mL n-heptane to obtain a suspension. The suspension was stirred at room temperature for two days. The resulting solid material was isolated by vacuum filtration and dried under vacuum at room temperature.

B. Characterization

The resulting solid material was subjected to XRPD, TGA, and DSC analysis using the conditions discussed above. The resulting XRPD pattern, DSC profile, and TGA profile are shown in FIGS. 9-10, respectively, and the XRPD peaks are shown in Table 7, above.

Based on the XRPD pattern shown in FIG. 9 and the XRPD peaks shown in Table 7, as well as the crystal structure and DSC and TGA profiles, the obtained solid material was determined to be a crystalline anhydrate of a gentisic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and was named crystalline Form 2.

C. Crystal Structure Determination

About 3.0 mg of crystalline Form 2 was added to a 3 mL glass vial with 0.5 mL THF/n-heptane (2:5, v/v) solvent mixture. The mixture was then shaken by an ultrasonic cleaner to accelerate dissolution. The resulting suspension was filtered and the obtained clear solution was transferred to a clean 4-mL shell vial (44.6 mm×14.65 mm). The shell vial was sealed by a PE-Plug with one pinhole. The shell vial was then placed in a fume hood at room temperature for slow evaporation. After 6 days of slow evaporation, block-like crystals were observed.

A suitable single crystal with good diffraction quality was selected out from the block-like crystal sample and was wrapped with Paratone-N (an oil based cryoprotectant). The crystal was mounted on a mylar loop in a random orientation and immersed in a stream of nitrogen at 120 K. Preliminary examination and data collection were performed on a Rigaku XtaLAB Synergy R (CuKα radiation, λ, =1.54184 Å) diffractometer and analyzed with the CrysAlisPro (V1.171.40.19a, Rigaku, 2018) software package. Cell parameters and an orientation matrix for data collection were retrieved and refined (T-vector Dirax algorithm) by CrysAlisPro (V1.171.40.19a, Rigaku, 2018) software using the setting angles of 50053 reflections in the range 3.539°<θ<75.936°. The data were collected to a minimum diffraction angle (θ) of 3.765° and a maximum diffraction angle (θ) of 76.018° at 120 K. The final point group completeness is 100%. The mean I/a of the data is 75.8 and the highest resolution is truncated at 0.79 Å.

Frames were integrated with CrysAlisPro (V1.171.40.19a, Rigaku, 2018). A total of 58850 reflections were collected, of which 6566 were unique. Lorentz and polarization corrections were applied to the data. An empirical absorption correction was performed using CrysAlisPro (V1.171.40.19a, Rigaku, 2018) using spherical harmonicas implemented in SCALE3 ABSPACK. The absorption coefficient μ of this material is 0.927 mm$^{-1}$ at this wavelength (λ=1.542 Å) and the minimum and maximum transmissions are 0.75213 and 1.0000, respectively. The agreement factor for the averaging was 3.94% based on intensity.

The structure was solved in the space group P2$_1$/c with the ShelXT structure solution program using Intrinsic Phasing and refined with ShelXL (Version 2018/3) refinement package using full-matrix least-squares on F$^2$ contained in OLEX2. All non-hydrogen atoms were refined anisotropically. The hydrogen atoms (H2) connected with the oxygen atoms (O2) was determined and refine freely based on the Fourier Map. Other hydrogen atoms were calculated geometrically and refined using the riding model.

A calculated XRPD pattern was generated for copper ("Cu") radiation using Mercury program and the atomic coordinates, space group, and unit cell parameters from the single crystal structure. Crystal structure representations were generated by Olex2 and Diamond. The thermal ellipsoids drawing was generated by ORTEP-III.

A suitable single crystal was separated and selected out from the block-like crystals and selected for single-crystal x-ray diffraction data collection. The crystal system of the single crystal was determined to be monoclinic and the space group was determined to be P2$_1$/c. Crystallographic data and the refinement parameters are listed in Table 13.

TABLE 13

| Crystallographic data of crystalline Form 2 | |
|---|---|
| Empirical formula | $C_{34}H_{31}F_3N_8O_5$ |
| Formula weight | 688.67 |
| Temperature | 120.00(10)K |
| Wavelength | CuKα (λ = 1.54184 Å) |
| Crystal system, space group | Monoclinic, P2$_{1/c}$ |
| Unit cell dimensions | a = 11.11290(10) Å |
| | b = 12.35560(10) Å |
| | c = 24.0484(2) Å |
| | α = 90° |
| | β = 102.4840(10)° |
| | γ = 90° |
| Volume | 3223.93(5) Å$^3$ |
| Z, CalMolated density | 4, 1.419 g/cm$^3$ |
| Absorption coefficient | 0.927 mm$^{-1}$ |
| F(000) | 1432.0 |
| Crystal size | 0.31 × 0.15 × 0.11 mm$^3$ |
| 2 Theta range for data collection | 7.53 to 152.036 |

TABLE 13-continued

| Crystallographic data of crystalline Form 2 | |
|---|---|
| Limiting indices | −13 ≤ h ≤ 13 |
| | −15 ≤ k ≤ 14 |
| | −30 ≤ l ≤ 29 |
| Reflections collected/ | 58850/6566 [R$_{int}$ = 0.0394, |
| Independent reflections | R$_{sigma}$ = 0.0132] |
| Refinement method | Full-matrix least-squares on F$^2$ |
| Completeness | 100% |
| Data/restraints/parameters | 6566/20/500 |
| Goodness-of-fit on F$^2$ | 1.160 |
| Final R indices [I ≥ 2sigma(I)] | R$_1$ = 0.0426, wR$_2$ = 0.0973 |
| Final R indices [all data] | R$_1$ = 0.0427, wR$_2$ = 0.0976 |
| Largest diff. peak and hole | 0.27/−0.23 e · Å$^{-3}$ |

As shown in FIG. 21, the asymmetric unit of the single crystal structure is comprised of one neutral compound of Formula (II) molecule and one gentisic acid neutral molecule, which indicated that crystalline Form 2 was actually a co-crystal of the starting compound with gentisic acid.

Example 7: Preparation and Characterization of Crystalline Form 3

A. Preparation

Approximately 20 mg of crystalline Form A was mixed with hydrochloric acid in a 1:2 molar ratio (Form A/acid) in an HPLC vial. 0.5 mL of MTBE was then added to form a suspension, which was magnetically stirred (~1000 rpm) at RT for about 3 days. The resulting solid material was dried at room temperature under vacuum.

B. Characterization

The resulting solid material was subjected to XRPD analysis using the conditions discussed above. The resulting XRPD pattern is shown in FIG. 15. The new crystalline form was named crystalline Form 3.

Example 8: Preparation and Characterization of Crystalline Form 4

A. Preparation

Approximately 20 mg of crystalline Form A was mixed with hydrobromic acid in a 1:1 molar ratio (Form A/acid) in an HPLC vial. 0.5 mL of MTBE was then added to form a suspension, which was magnetically stirred (~1000 rpm) at RT for about 3 days. The resulting solid material was dried at room temperature under vacuum.

B. Characterization

The resulting solid material was subjected to XRPD analysis using the conditions discussed above. The resulting XRPD pattern is shown in FIG. 16. The new crystalline form was named crystalline Form 4.

Example 9: Preparation and Characterization of Crystalline Form 5

A. Preparation

Approximately 20 mg of crystalline Form A was mixed with hydrobromic acid in a 1:1 molar ratio (Form A/acid) in an HPLC vial. 0.5 mL of EtOAc/n-Heptane (1:1, v/v) was then added to form a suspension, which was magnetically stirred (~1000 rpm) at RT for about 3 days. The resulting solid material was dried at room temperature under vacuum.

B. Characterization

The resulting solid material was subjected to XRPD analysis using the conditions discussed above. The resulting XRPD pattern is shown in FIG. 17. The new crystalline form was named crystalline Form 5.

Example 10: Preparation and Characterization of Crystalline Form 6

A. Preparation

Approximately 20 mg of crystalline Form A was mixed with ethanedisulfonic acid in a 1:1 molar ratio (Form A/acid) in an HPLC vial. 0.5 mL of Acetone/n-Heptane (1:4, v/v) was then added to form a suspension, which was magnetically stirred (~1000 rpm) at RT for about 3 days. The resulting solid material was dried at room temperature under vacuum.

B. Characterization

The resulting solid material was subjected to XRPD analysis using the conditions discussed above. The resulting XRPD pattern is shown in FIG. 18. The new crystalline form was named crystalline Form 6.

Example 11: Preparation and Characterization of Crystalline Form 7

A. Preparation

Approximately 20 mg of crystalline Form A was mixed with methanesulfonic acid in a 1:1 molar ratio (Form A/acid) in an HPLC vial. 0.5 mL of Acetone/n-Heptane (1:4, v/v) was then added to form a suspension, which was magnetically stirred (~1000 rpm) at RT for about 3 days. The resulting solid material was dried at room temperature under vacuum.

B. Characterization

The resulting solid material was subjected to XRPD analysis using the conditions discussed above. The resulting XRPD pattern is shown in FIG. 19. The new crystalline form was named crystalline Form 7.

Example 12: Preparation and Characterization of Crystalline Form A1

A. Preparation

Purified 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) was prepared according to the procedures disclosed in U.S. Provisional Patent Application Nos. 62/783,014; 62/799,423; and 62/868,616. The purified compound was then recrystallized in hexane and isopropanol using methods known to those skilled in the art.

B. Characterization 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III) obtained as discussed above, was subjected to XRPD, TGA, and DSC analysis using the conditions discussed above. The resulting XRPD pattern, DSC profile, and TGA profile are shown in FIGS. 11-12, respectively, and the XRPD peaks are shown in Table 10, above.

Based on the XRPD pattern shown in FIG. 11 and the XRPD peaks shown in Table 7, as well as the crystal structure and DSC and TGA profiles, 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III), obtained as discussed above, was determined to be a crystalline anhydrate and was named crystalline Form A1.

C. Crystal Structure Determination

Approximately 4.8 mg of crystalline Form A1 was added into a 3 mL glass vial with 0.5 mL EtOH/n-heptane (1:3, v/v) solvent mixture. After being shaken by an ultrasonic cleaner to accelerate dissolution, the suspension was filtered and the obtained clear solution was transferred to a clean 4 mL shell vial (44.6 mm×14.65 mm). The shell vial was sealed by PE-Plug with one pinhole. The shell vial was then placed in a fume hood at room temperature for slow evaporation. After 5 days of slow evaporation, thin rod-like crystals were observed.

A suitable single crystal with good diffraction quality was selected from the thin rod-like crystal sample and was wrapped with Paratone-N (an oil based cryoprotectant). The crystal was mounted on a mylar loop in a random orientation and immersed in a stream of nitrogen at 120 K. Preliminary examination and data collection were performed on a Rigaku XtaLAB Synergy R (CuKα radiation, λ, =1.54184 Å) diffractometer and analyzed with the CrysAlisPro (V1.171.40.19a, Rigaku, 2018) software package. Cell parameters and an orientation matrix for data collection were retrieved and refined (T-vector Dirax algorithm) by CrysAlisPro (V1.171.40.19a, Rigaku, 2018) software using the setting angles of 24455 reflections in the range $3.516°<\theta<75.351°$. The data were collected to a minimum diffraction angle (θ) of 3.541° and a maximum diffraction angle (θ) of 75.982° at 120 K. The final point group completeness is 100%. The mean I/σ of the data is 71.4 and the highest resolution is truncated at 0.79 Å.

Frames were integrated with CrysAlisPro (V1.171.40.19a, Rigaku, 2018). A total of 52006 reflections were collected, of which 4790 were unique. Lorentz and polarization corrections were applied to the data. An empirical absorption correction was performed using CrysAlisPro (V1.171.40.19a, Rigaku, 2018) using spherical harmonicsas implemented in SCALE3 ABSPACK. The absorption coefficient μ of this material is 0.932 $mm^{-1}$ at this wavelength (λ=1.542 Å) and the minimum and maximum transmissions are 0.72018 and 1.0000, respectively. Intensities of equivalent reflections were averaged, the agreement factor for the averaging was 3.24% based on intensity.

The structure was solved in the space group $P2_1/c$ with the ShelXT structure solution program using Intrinsic Phasing and refined with ShelXL (Version 2018/3) refinement package using full-matrix least-squares on $F^2$ contained in OLEX2. All non-hydrogen atoms were refined anisotropically. The hydrogen atoms were calculated geometrically and refined using the riding model.

The calculated XRPD pattern was generated for Cu radiation using Mercury program and the atomic coordinates, space group, and unit cell parameters from the single crystal structure. The crystal structure representations were generated by Olex2 and Diamond. The atomic thermal displacement ellipsoids drawing was generated by ORTEP-III.

A suitable single crystal was separated out from the thin rod-like crystals and selected for single-crystal X-ray diffraction data collection. The crystal system of the single crystal was determined to be monoclinic and the space group was $P2_1/c$. Crystallographic data and the refinement parameters are listed in Table 14.

TABLE 14

Crystallographic data of crystalline Form A1

| | |
|---|---|
| Empirical formula | $C_{25}H_{21}F_3N_8O$ |
| Formula weight | 506.50 |

TABLE 14-continued

Crystallographic data of crystalline Form A1

| | |
|---|---|
| Temperature | 120.01(10)K |
| Wavelength | CuKα (λ = 1.54184 Å) |
| Crystal system, space group | Monoclinic, P2$_{1/c}$ |
| Unit cell dimensions | a = 12.54460(7) Å |
| | b = 8.63964(5) Å |
| | c = 21.66044(12) Å |
| | α = 90° |
| | β = 95.6607(5)° |
| | γ = 90° |
| Volume | 2336.13(2) Å$^3$ |
| Z, CalMolated density | 4, 1.440 g/cm$^3$ |
| Absorption coefficient | 0.932 mm$^{-1}$ |
| F(000) | 1048.0 |
| Crystal size | 0.11 × 0.04 × 0.03 mm$^3$ |
| 2 Theta range for data collection | 7.082 to 151.964 |
| Limiting indices | −11 ≤ h ≤ 15 |
| | −10 ≤ k ≤ 10 |
| | −27 ≤ l ≤ 27 |
| Reflections collected/ | 52006/4790 [R$_{int}$ = 0.0324, |
| Independent reflections | R$_{sigma}$ = 0.0140] |
| Refinement method | Full-matrix least-squares on F$^2$ |
| Completeness | 100% |
| Data/restraints/parameters | 4790/0/336 |
| Goodness-of-fit on F$^2$ | 1.054 |
| Final R indices [I ≥ 2sigma(I)] | R$_1$ = 0.0434, wR$_2$ = 0.1085 |
| Final R indices fall data] | R$_1$ = 0.0460, wR$_2$ = 0.1114 |
| Largest diff. peak and hole | 0.35/−0.35 e · Å$^{-3}$ |

As shown in FIG. 22, the asymmetric unit of the single crystal structure was comprised of only one compound of Formula (III) molecule, which suggested that crystalline Form A1 is an anhydrate.

Example 13: Preparation and Characterization of Crystalline Form B1

A. Preparation

Approximately 20 mg of crystalline Form A1 was suspended in 0.5 mL of EtOAc/n-Heptane (1:2, v/v) in an HPLC vial and magnetically stirred (~1000 rpm) at RT for about 3 days. The resulting solid material was dried at room temperature under vacuum.

B. Characterization

The resulting solid material was subjected to XRPD, TGA, and DSC analysis using the conditions discussed above. The resulting XRPD pattern, DSC profile, and TGA profile are shown in FIGS. 13-14, respectively, and the XRPD peaks are shown in Table 11, above.

Based on the XRPD pattern shown in FIG. 13 and the XRPD peaks shown in Table 8, as well as the DSC and TGA profiles, the obtained solid material was determined to be a crystalline anhydrate and was named crystalline Form B1.

Example 14: Mouse Pharmacokinetic Studies

Mouse pharmacokinetic (PK) studies were conducted using Crystalline Form A of 6-(4-cyclopropyl-6-methoxy-pyrimidin-5-yl)-1-(4-(1-isopropyl-4-(trifluoromethyl)-1H-imidazol-2-yl)benzyl)-1H-pyrazolo[3,4-d]pyrimidine, as disclosed herein, Crystalline Form 2 of a gentisic acid co-crystal of 6-(4-cyclopropyl-6-methoxypyrimidin-5-yl)-1-(4-(1-isopropyl-4-(trifluoromethyl)-1H-imidazol-2-yl)ben-zyl)-1H-pyrazolo[3,4-d]pyrimidine, as disclosed herein, and Crystalline Form 8 of a benzoic acid co-crystal of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine, as disclosed herein.

The PK studies consisted of single dose oral exposure studies, which were conducted in female NOD/SCID mice (approximately 6 to 8 weeks, and 20-30 g at the time of study) using a compound dose of 300 mg/kg and a dosing volume of 10 mL/kg. The mice were fasted overnight prior to dosing. Animals had free access to food and water post-dosing.

Blood was sampled serially from the dorsal metatarsal vein at pre-dose, 0.25, 0.5, 1, 2, 4, 8, 24, 48 (crystalline Form 2 only), and 72 hours (crystalline Form 2 only) post PO dosing. Approximately 0.03 mL blood was collected at each time point and centrifuged at 4000 G for 5 minutes at 4° C. to provide plasma. The plasma samples were then stored in a freezer at −75±15° C. prior to LC-MS/MS analysis.

Concentrations of each compound in the plasma samples were then analyzed using an LC-MS/MS method. WinNonlin (Phoenix™, version 6.1) or other similar software was used for PK calculations. The following PK parameters were calculated, whenever possible from the plasma concentration versus time data: $C_{max}$, $T_{max}$, $T_{1/2}$, $AUC_{inf}$, and $AUC_{last}$. The PK data were described using descriptive statistics such as mean with standard deviation.

The results for crystalline form A are shown in Table 15 below and in FIG. 23.

TABLE 15

Summary of Crystalline Form A PK Parameters

| PK Parameters | Unit | Mouse 7 | Mouse 8 | Mouse 9 | Mean | SD | CV(%) |
|---|---|---|---|---|---|---|---|
| $T_{1/2}$ | h | NA | 6.79 | 18.6 | 12.7 | NA | NA |
| $T_{max}$ | h | 8.00 | 4.00 | 4.00 | 5.33 | 2.31 | 43.3 |
| $C_{max}$ | ng/mL | 4450 | 2890 | 3750 | 3697 | 781 | 21.1 |
| $AUC_{last}$ | h * ng/mL | 72653 | 40678 | 68658 | 60663 | 17422 | 28.7 |

The results for crystalline Form 2 are shown in Table 16 below and in FIG. 24.

TABLE 16

Summary of Crystalline Form 2 PK Parameters

| PK Parameters | Unit | Mouse 7 | Mouse 8 | Mouse 9 | Mean | SD | CV(%) |
|---|---|---|---|---|---|---|---|
| $T_{1/2}$ | h | 4.03 | 4.22 | 4.27 | 4.17 | 0.13 | 3.12 |
| $T_{max}$ | h | 8.00 | 12.0 | 12.0 | 10.7 | 2.3 | 21.7 |

TABLE 16-continued

Summary of Crystalline Form 2 PK Parameters

| PK Parameters | Unit | Mouse 7 | Mouse 8 | Mouse 9 | Mean | SD | CV(%) |
|---|---|---|---|---|---|---|---|
| $C_{max}$ | ng/mL | 28800 | 28900 | 29000 | 28900 | 100 | 0.346 |
| $AUC_{last}$ | h * ng/mL | 827348 | 835713 | 594288 | 752450 | 137036 | 18.2 |

Example 15: Preparation and Characterization of Crystalline Form F

A. Preparation

A mixture of Formula II (1 g) in 50% acetone/water (10 vol) was heated to reflux and held at that temperature for at least 30 minutes. The resulting clear solution was then cooled to room temperature and stirred overnight. The resulting slurry was filtered and dried to provide Form F (800 mg) as a white solid.

B. Characterization

The resulting white solid material was subjected to XRPD and DSC analysis using the conditions discussed above. The resulting XRPD pattern and DSC profile are shown in FIGS. 25 and 26, respectively, and the XRPD peaks are shown in Table 5.

Based on the XRPD pattern shown in FIG. 25 and the XRPD peaks shown in Table 5, as well as the DSC profile shown in FIG. 26, the obtained solid material was determined to be a crystalline anhydrate and was named crystalline Form F.

Example 16: Additional Co-Crystal Screens

Additional co-crystal screens were carried out to identify further solid state forms of Formula (II).

A. Instrumentation

Differential scanning calorimetry (DSC) was carried out with a TA Instruments Q2000 instrument (closed aluminum sample pan aluminum sample pan with a pinhole in the lid, heating rate 20 K/min). The melting point is understood as the peak maximum.

Light microscopy was performed on a Leitz Orthoplan polarized microscope part #130880, generally a 10×10 magnification was applied.

X-ray powder diffraction (XRPD) was carried out with a Stoe Stadi P diffractometer equipped with a Mythen1K detector operating with Cu-Kα1 radiation. The measurements with this instrument were performed in transmission at a tube voltage of 40 kV and 40 mA tube power. A curved Ge monochromator allows testing with Cu-Kα1 radiation. The following parameters were set: 0.02° 2θ step size, 12 s step time, 1.5-50.5° 2θ scanning range, and 1° 2θ detector step (detector mode in step scan). For a typical sample preparation about 10 mg of sample was placed between two acetate foils and mounted into a Stoe transmission sample holder. The sample was rotated during the measurement. All sample preparation and measurement was done in an ambient air atmosphere.

TG-FTIR measurements were carried out with a Netzsch Thermo-Microblanace TG209 coupled to a Bruker FTIR Spectrometer Vector 22 (sample pans with a pinhole, $N_2$ atmosphere, heating rate 10° C./min to 300 or 350° C.).

B. Starting Material

The starting material was a freebase form of Formula (II).

Salt and Cocrystal Screens

Cocrystal screening experiments with Formula II were carried out with adipic acid, benzoic acid, ethyl maltol, gallic acid (3,4,5-trihydroxybenzoic acid), gallic acid ethyl ester, 4-hydroxy benzoic acid, 4-hydroxy benzoic acid methyl ester, nicotinic acid, nicotinamide, L-proline, saccharin, salicylic acid, D-sorbitol, and succinic acid. The experimental parameters and results for the cocrystal screening experiments are listed in Table 17.

TABLE 17

Summary of co-crystal screening experiments and results

| Experiment | Description | Characterization | Result |
|---|---|---|---|
| 1 | Material as received: Formula (II). | XRPD | Free base |
| 2 | 1.0 ml acetic acid added to 80 mg of Formula (II). Clear solution obtained, then let solvent evaporate slowly in air at r.t. | Visual inspection | Glassy residue, amorphous. |
| 3 | 100 mg of Formula (II) and 120 mg of adipic acid (1:4 eq) were dissolved together in THF (8 mL), then 6 mL of heptane were added. A light turbidity formed, and the suspension was agitated for 3 days. The mixture was sonicated for two minutes and filtered. The resulting white solid was submitted to XRPD. | XRPD | Free base + free adipic acid |
| 4 | 80 mg of Formula (II) and 20 mg of benzoic acid (1:1.1 eq) were ground together in a ball mill for 10 min with 50 μL of ethyl acetate as solvent. The resulting white solid was submitted to XRPD. | XRPD | Free base + free benzoic acid |
| 5 | 80 mg of Formula (II) and 80 mg of benzoic acid (1:4.4 eq) were dissolved together in EtOAc (1 mL), then 4 mL of heptane were added. A light turbidity formed, and the suspension was agitated for 3 days. The mixture was sonicated for two minutes and filtered. The resulting white solid was submitted to XRPD. | XRPD | Crystalline, benzoic acid cocrystal. 1:1 API:BNZ according to NMR |
| 6 | 80 mg of Formula (II) and 20 mg of benzoic acid (1:1.1 eq) were dissolved together in EtOAc | XRPD | Free base |

TABLE 17-continued

Summary of co-crystal screening experiments and results

| Experiment | Description | Characterization | Result |
|---|---|---|---|
|  | (0.5 mL), then 3 mL of heptane were added. A light turbidity formed, and the suspension was agitated for 1 day. The mixture was filtered. The resulting white solid was submitted to XRPD. | | |
| 7 | 540 mg of Formula (II) dissolved in 10 ml isopropanol. Produced a stock solution of benzoic acid in isopropanol (1.8890 g in 14 ml ~ 1M). Then 4.0 ml of the benzoic acid stock solution was added to the solution with the API and some isopropanol was slowly evaporated using a slight nitrogen purge. After two days a thick suspension was obtained which was diluted with 2 ml heptane and 2 ml isopropanol. The solid was then separated by filtration and submitted for XRPD. | XRPD | Mixture of free base and benzoic acid cocrystal. |
| 8 | 600 mg of Formula (II) and 600 mg of benzoic acid (1:4.4 eq) were dissolved together in EtOAc (5 mL), 19 mL of heptane were added slowly (over 2-3 minutes). A light turbidity formed, and the suspension was agitated for 1 day. The day after white solid was present on the walls, the mixture was sonicated for 1-2 minutes and filtered. The resulting white solid was submitted to XRPD. Ca. 700 mg of white product was recovered. | XRPD | Benzoic acid cocrystal. 1:1 |
| 9 | 700 mg of Formula (II) and 700 mg of benzoic acid (1:4.4 eq) were dissolved together in EtOAc (5mL), 20 mL of heptane were added slowly (over 2-3 minutes). A light turbidity formed, and the suspension was stirred overnight at room temperature. After overnight stirring the suspension was filtered and the resulting white solid was submitted for XRPD and further characterizations after drying at r.t. for about 30 minutes. Ca. 700 mg of white product was recovered. | XRPD | Benzoic acid cocrystal. 1:1 Purity = 99.78% |
| 10 | Prepared a stock solution with 4-hydroxbenzoic acid (4HB) in acetone (268 mg in 2.0 ml acetone ~ 1.0M) | Visual inspection | No crystalline product obtained. |
| 11 | The remaining amount of the 4HB stock solution (~1.78 ml) was diluted with 3.0 ml heptane. This led to a precipitate that was dissolved by adding 1.0 ml of acetone; thus a nearly saturated solution was obtained which was added to about 100 mg of Formula (II). | Visual inspection | No crystalline product obtained. |
| 12 | To 60 mg of Formula (II) was added 120 mg of D-panthenol and one ml acetone. A clear solution was obtained to which 4 ml heptane was added; however, this led to a sticky mass/emulsion that did not crystallize. | Visual inspection | No crystalline product obtained. |
| 13 | 80 mg of Formula (II) and 26 mg of ethyl maltol (1:1.1 eq) were ground in a ball mill for 10 min with 50 μL of ethyl acetate as solvent and solid product was submitted for XRPD. | XRPD | Free base + Ethyl maltol |
| 15 | 1.0 ml of a stock solution of gallic acid in acetone (0.23M) mixed with a stock solution of Formula (II) in acetone (0.1M) the allow the solvent to evaporate in air at r.t. Since just a glassy residue was obtained, the residue was again dissolved in 5.0 ml acetone and 5.0 ml heptane was added. No precipitate was observed; thus the solvents were allowed to evaporate again from an open vial; however, no crystalline product was obtained. | Visual inspection | No crystalline product obtained. |
| 16 | 278 mg of Formula (II) (0.5 mmol) dissolved in 5.0 acetone, and 330 mg of gallic acid (2.0 mmol) dissolved in 5.0 ml acetone. Then added 1.5 m of the gallic acid solution to the free drug substance solution and let solvent evaporate slowly from open vial at r.t. However, a glassy residue was obtained. To the glassy residue was added 1 ml water and 1 ml isopropanol. A suspension with crystalline material was obtained which was filtered and the solid product submitted for XRPD. | XRPD | Free base |
| 17 | 300 mg of Formula (II) (0.5 mmol) and 430 mg of gallic acid (2.0 mmol) were dissolved together in 5.0 of EtOH. A thick suspension was obtained at the beginning, but heating gently (ca. 50° C.), all dissolved. The solution was let evaporate for three days, a suspension with crystalline material was | XRPD | Gallic acid |

TABLE 17-continued

Summary of co-crystal screening experiments and results

| Experiment | Description | Characterization | Result |
|---|---|---|---|
|  | obtained which was filtered and the solid product submitted for XRPD. | | |
| 18 | 80 mg of Formula (II) and 20 mg of glutaric acid (1:1.1 eq) were ground together in a ball mill for 10 min with 50 μL of acetone as solvent. The resulting white solid was submitted to XRPD. | XRPD | Free base + free glutaric acid |
| 19 | 100 mg D,L-mandelic acid was added to 50 mg of Formula (II) and 1.0 ml acetone was added. A clear solution was obtained to which 4 ml heptane was added. After stirring for four days most of the solid material stuck to the glass wall. Therefore all was dissolved by adding 10 TBME and the solvents were allowed to evaporate under nitrogen. | Visual inspection | No crystalline product obtained. |
| 20 | 80 mg of Formula (II) and 80 mg of 4-hydroxybenzoic acid methyl ester (1:3:5 eq) were dissolved in 4.0 ml acetone. Then 6 ml heptane was added but no precipitate was observed. After addition of 22 ml heptane, in total, a suspension was obtained from which the solid product was separated by filtration and submitted to XRPD. | XRPD: | XRPD shows a mixture of MHB and free base. |
| 21 | 80 mg of Formula (II) and 20 mg of nicotinic acid (1:1.2 eq) were ground in a ball mill for 10 min with 60 μL of MeOH as the solvent. The resulting white solid was submitted to XRPD. | XRPD | Possible MeOH solvate + free nicotinic acid |
| 22 | 80 mg of Formula (II) and 20 mg of nicotinamide (1:1.2 eq) were ground in a ball mill for 10 min with 60 μL of MeOH as the solvent. The resulting white solid was submitted to XRPD. | XRPD | Possible MeOH solvate + free nicotinamide |
| 23 | 50 mg of Formula (II) were dissolved in 1 mL of a saturated solution of nicotinamide (ca. 0.25M) in acetone, the mixture was transparent. The solution was concentrated overnight until dryness. The resulting white solid was submitted to XRPD. | XRPD | Free base + free nicotinamide |
| 24 | 80 mg of Formula (II) and 20 mg of nicotinamide (1:1.1 eq) were dissolved together in EtOAc (0.5 mL), then 3 mL of heptane were added. A precipitate appeared. The mixture was filtered. The resulting white solid was submitted to XRPD. | XRPD | Free base + free nicotinamide |
| 25 | 80 mg of Formula (II) and 20 mg of proline (1:1.1 eq) were ground in a ball mill for 10 min with 60 μL of MeOH as the solvent. The resulting white solid was submitted to XRPD. | XRPD | Possible MeOH solvate + free proline |
| 26 | 100 mg of Formula (II) and 160 mg of saccharine (1:4 eq) were dissolved together in Acetone (4 mL), then 4 mL of heptane were added and the solution became cloudy. The mixture was stirred for 3 days at r.t. Filtered and submitted to XRPD. | XRPD | Free base + free saccharine |
| 27 | 50 mg of Formula (II) and 100 mg of salicylic acid (1:4.4 eq) were dissolved in EtOAc (2 mL), and then 16 mL of heptane was added. A light turbidity formed, and the suspension was agitated for 3 days. The mixture was sonicated for two minutes and filtered. The resulting white solid was submitted to XRPD. | XRPD | Crystalline, possible salicylic acid co-crystal with some excess of salicylic acid. |
| 28 | The XRPD pattern showed that an excess of salicylic was present, thus the solid product was washed with i-PrOH (3 mL), filtered again and submitted to XRPD and NMR. | XRPD | Salicylic acid co-crystal still with some excess of salicylic acid. TG-FTIR suggests solvent free form. |
| 29 | 157 mg of Formula (II) dissolved in 3.0 ml isopropanol (heated to dissolve). Produced a stock solution of salicylic acid in isopropanol (~1.1M) and added 1.0 ml of this solution to the drug substance solution. Seeded with SP273-SAL-P1-w and stirred at r.t. Let slowly evaporate part of the solvent (about one ml was evaporated after three days) then filtered and submitted solid for XRPD. | XRPD | Salicylic acid cocrystal. 1:1 |
| 30 | 80 mg of Formula (II) and 30 mg of sorbitol (1:1.2 eq) were ground in a ball mill for 10 min with 60 | XRPD | Possible MeOH |

TABLE 17-continued

Summary of co-crystal screening experiments and results

| Experiment | Description | Characterization | Result |
|---|---|---|---|
|  | μL of MeOH as solvent. The resulting white solid was submitted to XRPD. |  | solvate + free sorbitol |
| 31 | 40 mg of Formula (II) were dissolved in 1 mL of a saturated solution of sorbitol (ca. 0.05M) in EtOH at 75° C., the mixture was transparent. The solution was concentrated overnight, few crystals appeared at the walls (very little substance), concentrated another 24 h, the solution evaporated completely leaving a white solid. The resulting white solid was submitted to XRPD. | XRPD | Free base + free sorbitol |
| 32 | 50 mg of Formula (II) and 100 mg of succinic acid (1:5 eq) were dissolved together in acetone (4 mL) heating at 35° C. All dissolved. The clear solution was stirred for 1 day. The day after a suspension appeared. Filtered and submitted to XRPD. | XRPD | Succinic acid, no cocrystal formation. |

Example 17: Characterization of Crystalline Form 8

A. Characterization

The benzoic acid cocrystal from experiment 5 in Table 17 was analyzed via

XRPD, DSC, and TG-FTIR analysis using the aforementioned conditions. The resulting XRPD pattern, DSC profile, and TG-FTIR profile are shown in FIGS. 29-31, respectively, and the XRPD peaks are shown in Table 8.

Based on the XRPD pattern shown in FIG. 29 as well as the DSC and TGA profiles, the obtained solid material was determined to be a benzoic acid cocrystal and was named crystalline Form 8.

B. Crystal Structure Determination

About 82.4 mg of Formula (II) benzoic acid co-crystal starting material was added into a 3-mL glass vial with the addition of 2.0 mL EtOAc/n-hexane (1:6, v/v) solvent mixture. The suspension was magnetically stirred (1000 rpm) at RT for 5 days and filtered by 0.45 μm PTFE membrane. Then 0.5 mL of the clear filtrate was transferred to a clean 4-mL shell vial (44.6 mm×14.65 mm). The shell vial was sealed by PE-Plug with one pinhole and placed in a fume hood at room temperature for slow evaporation. After 14 days' slow evaporation, block-like crystals were obtained.

A suitable single crystal with good diffraction quality was selected out from the block-like crystal sample and was wrapped with Paratone-N (an oil based cryoprotectant). The crystal was mounted on a mylar loop in a random orientation and immersed in a stream of nitrogen at 120 K. Preliminary examination and data collection were performed on a Rigaku XtaLAB Synergy R (Cu/K$_\alpha$, X-ray radiation, λ, =1.54184 Å) diffractometer and analyzed with the CrysAlisPro (V1.171.40.67a, Rigaku, 2019) software package.

Cell parameters and an orientation matrix for data collection were retrieved and refined (T-vector Dirax algorithm) by CrysAlisPro (V1.171.40.67a, Rigaku, 2019) software using the setting angles of 37110 reflections in the range 3.716°<θ<75.227°. The data were collected to a minimum diffraction angle (θ) of 3.734° and a maximum diffraction angle (θ) of 76.055° at 120 K. The completeness is 100%. The mean I/a of the data is 64.1 and the highest resolution is truncated at 0.79 Å.

Frames were integrated with CrysAlisPro (V1.171.40.67a, Rigaku, 2019). A total of 66366 reflections were collected, of which 6371 were unique. Lorentz and polarization corrections were applied to the data. An empirical absorption correction was performed using CrysAlisPro (V1.171.40.67a, Rigaku, 2019) using spherical harmonicas implemented in SCALE3 ABSPACK. The absorption coefficient μ of this material is 0.882 mm$^{-1}$ at this wavelength (λ=1.542 Å) and the minimum and maximum transmissions are 0.7464 and 1.0000, respectively. Intensities of equivalent reflections were averaged. The agreement factor for the averaging was 3.65% based on intensity.

The structure was solved in the space group P2$_1$/n with the ShelXT (Sheldrick, G. M. Acta Cryst. 2015, A71, 3-8) structure solution program using Intrinsic Phasing and refined with ShelXL (Version 2018/3) refinement package (Sheldrick, G. M. Acta Cryst. 2015, C71, 3-8) using full-matrix least-squares on F$^2$ contained in OLEX2 (Dolomanov, O. V., Bourhis, L. J., Gildea, R. J, Howard, J. A. K. & Puschmann, H. J. Appl. Cryst. 2009, 42, 339-341). All non-hydrogen atoms were refined anisotropically. The hydrogen atoms (H2) connected with the oxygen atoms (O2) was determined and refined freely based on the Fourier Map. Other hydrogen atoms were calculated geometrically and refined using the riding model.

The calculated XRPD pattern was generated for Cu radiation using Mercury program (Macrae, C. F., Edgington, P. R., McCabe, P., Pidcock, E., Shields, G. P., Taylor, R., Towler, M. & van de Streek, J. J. Appl. Cryst. 2006, 39, 453-457) and the atomic coordinates, space group, and unit cell parameters from the single crystal structure.

The crystal structure representations were generated by Olex2 and Diamond (Brandenburg, K. DIAMOND, 1999, Crystal Impact GbR, Bonn, Germany). The thermal ellipsoids drawing was generated by ORTEP-III (L. J. Farrugia. J. Appl. Cryst. 2012, 45, 849-854).

A suitable single crystal was separated and selected out from the block-like crystals and selected for single-crystal x-ray diffraction data collection. The crystal system of the single crystal was determined to be monoclinic and the space group was determined to be P2$_1$/n. Crystallographic data and refinement parameters are shown in Table 18.

TABLE 18

Crystallographic data of crystalline Form 8

| | |
|---|---|
| Empirical formula | C$_{34}$H$_{31}$F$_3$N$_8$O$_3$ |
| Formula weight | 656.67 |
| Temperature | 120.00(10) K |
| Wavelength | CuKα (λ = 1.54184 Å) |
| Crystal system, space group | Monoclinic, P2$_1$/n |
| Unit cell dimensions | a = 10.61070(10) Å |

TABLE 18-continued

Crystallographic data of crystalline Form 8

| | |
|---|---|
| | b = 12.39940(10) Å |
| | c = 24.15170(10) Å |
| | α = 90° |
| | β = 101.4110(10)° |
| | γ = 90° |
| Volume | 3114.74(4) Å$^3$ |
| Z, CalMolated density | 4, 1.440 g/cm$^3$ |
| Absorption coefficient | 0.882 mm$^{-1}$ |
| F(000) | 1368.0 |
| Crystal size | 0.047 × 0.043 × 0.033 mm$^3$ |
| 2 Theta range for data collection | 7.012 to 110.646 |
| Limiting indices | −12 ≤ h ≤ 13 |
| | −15 ≤ k ≤ 15 |
| | −29 ≤ l ≤ 30 |
| Reflections collected/Independent reflections | 66366/6371 [$R_{int}$ = 0.0365, $R_{sigma}$ = 0.0156] |
| Refinement method | Full-matrix least-squares on F$^2$ |
| Completeness | 100% |
| Data/restraints/parameters | 6371/0/440 |
| Goodness-of-fit on F$^2$ | 1.046 |
| Final R indices [I ≥ 2sigma(I)] | $R_1$ = 0.0417, $wR_2$ = 0.1067 |
| Final R indices [all data] | $R_1$ = 0.0446, $wR_2$ = 0.1088 |
| Largest diff. peak and hole | 0.64/−0.25 e · Å$^{-3}$ |

As shown in FIG. 32, the asymmetric unit of the single crystal structure was comprised of one neutral Formula (II) molecule and one neutral benzoic acid molecule, which indicated that the crystal is a benzoic acid cocrystal of Formula (II).

Example 18: Characterization of Crystalline Form 9

A. Characterization

The salicylic acid cocrystal from experiment 29 in Table 17 was analyzed via XRPD and $^1$H NMR analysis using the aforementioned conditions. The resulting XRPD and $^1$H NMR patterns are shown in FIGS. 33-34, respectively.

Based on the XRPD pattern shown in FIG. 33 as well as the $^1$H NMR profile (FIG. 34), the obtained solid material was determined to be a salicylic acid cocrystal and was named crystalline Form 9.

A. Crystal Structure Determination

About 3.2 mg of Formula (II) salicylic acid cocrystal was added into a 3-mL glass vial with the additional of 0.5 mL acetone/n-heptane (1:8, v/v) solvent mixture. Ultrasonication was applied to accelerate dissolution of solid sample, after which the suspension was filtered by a filter (0.45 μm PTFR membrane). Then the clear filtrate was transferred to a clean 4-mL shell vial (44.6 mm×14.65 mm). The shell vial was sealed by PE-Plug with one pinhole. The shell vial was placed in a fume hood at room temperature for slow evaporation. After 2 days' slow evaporation, rod-like crystals were observed.

A suitable single crystal with good diffraction quality was selected out from the rod-like crystal sample and was wrapped with Paratone-N (an oil based cryoprotectant). The crystal was mounted on a mylar loop in a random orientation and immersed in a stream of nitrogen at 184 K. Preliminary examination and data collection were performed on a Bruker D8 Venture (METALJET Ga X-ray source, PHOTON II) diffractometer and analyzed with the APEX3 software package.

Cell parameters and an orientation matrix for data collection were retrieved and refined by SAINT (Version: 8.37A) software using the setting angles of 9918 reflections in the range 3.252°<θ<54.786°. The data were collected to a minimum diffraction angle (θ) of 3.506° and a maximum diffraction angle (θ) of 55.323° at 184 K. The completeness is 99.84%. The mean I/σ of the data is 13.0 and the highest resolution is truncated at 0.82 Å.

Frames were integrated with SAINT (Version: 8.37A). A total of 38333 reflections were collected, of which 6058 were unique. Lorentz and polarization corrections were applied to the data. An absorption correction was performed using SADABS (Version: 2016/2) with multi-scan method. The absorption coefficient μ of this material is 0.579 mm-1 at this wavelength (=1.34139 Å) and the minimum and maximum transmissions are 0.5107 and 0.7508, respectively. The agreement factor for the averaging was 12.23% based on intensity.

The structure was solved in the space group P2$_1$/c with the ShelXT$^1$ structure solution program using Intrinsic Phasing and refined with ShelXL$^2$ (Version 2018/3) refinement package using full-matrix least-squares on F$^2$ contained in OLEX2. All non-hydrogen atoms were refined anisotropically. The hydrogen atoms (H2) connected with the oxygen atoms (O2) was determined and refined freely based on the Fourier Map. Other hydrogen atoms were calculated geometrically and refined using the riding model.

The calculated XRPD pattern was generated for Cu radiation using Mercury program and the atomic coordinates, space group, and unit cell parameters from the single crystal structure. The crystal structure representations were generated by Olex2 and Diamond.

A suitable single crystal was separated and selected out from the block-like crystals and selected for single-crystal x-ray diffraction data collection. The crystal system of the single crystal was determined to be monoclinic and the space group was determined to be P2$_1$/c. Crystallographic data and the refinement parameters are listed in Table 19.

TABLE 19

Crystallographic data of crystalline Form 9

| | |
|---|---|
| Empirical formula | C$_{34}$H$_{31}$F$_3$N$_8$O$_4$ |
| Formula weight | 672.67 |
| Temperature | 184.08 K |
| Wavelength | CuKα (λ = 1.34139 Å) |
| Crystal system, space group | Monoclinic, P2$_1$/c |
| Unit cell dimensions | a = 10.8387(11) Å |
| | b = 12.3761(12) Å |
| | c = 24.242(2) Å |
| | α = 90° |
| | β = 102.631(5)° |
| Volume | 3173.1(5) Å$^3$ |
| Z, CalMolated density | 4, 1.408 g/cm$^3$ |
| Absorption coefficient | 0.579 mm$^{-1}$ |
| F(000) | 1400.0 |
| Crystal size | 0.08 × 0.06 × 0.05 mm$^3$ |
| 2 Theta range for data collection | 7.012 to 110.646 |
| Limiting indices | −12 ≤ h ≤ 13 |
| | −15 ≤ k ≤ 14 |
| | −29 ≤ l ≤ 29 |
| Reflections collected/Independent reflections | 38333/6058 [$R_{int}$ = 0.1223, $R_{sigma}$ = 0.0767] |
| Refinement method | Full-matrix least-squares on F$^2$ |

TABLE 19-continued

Crystallographic data of crystalline Form 9

| | |
|---|---|
| Completeness | 100% |
| Data/restraint/parameters | 6058/0/454 |
| Goodness-of-fit on $F^2$ | 1.048 |
| Final R indices [I ≥ 2sigma(I)] | $R_1$ = 0.0644, $wR_2$ = 0.1585 |
| Final R indices [all data] | $R_1$ = 0.1065, $wR_2$ = 0.1867 |
| Largest diff. peak and hole | 0.44/−0.35 e · Å$^{-3}$ |

As shown in FIG. 35, the asymmetric unit of the single crystal structure was comprised of one neutral Formula (II) molecule and a neutral salicylic acid molecule, which indicated that the crystal is a salicylic acid cocrystal of Formula (II).

Example 19: Mouse Pharmacokinetic Studies

Mouse pharmacokinetic (PK) studies were conducted using Crystalline Form 8 of 6-(4-cyclopropyl-6-methoxy-pyrimidin-5-yl)-1-(4-(1-isopropyl-4-(trifluoromethyl)-1H-imidazol-2-yl)benzyl)-1H-pyrazolo[3,4-d]pyrimidine, as disclosed herein.

The PK studies consisted of single dose oral exposure studies, which were conducted in female NOD/SCID mice (approximately 6 to 8 weeks, and 20-30 g at the time of study) using a compound dose of 300 mg/kg and a dosing volume of 10 mL/kg. The mice were fasted overnight prior to dosing. Animals had free access to food and water post-dosing.

Blood was sampled serially from the dorsal metatarsal vein at pre-dose, 0.25, 0.5, 1, 2, 4, 8, and 24 hours post PO dosing. Approximately 0.03 mL blood was collected at each time point and centrifuged at 4000 G for 5 minutes at 4° C. to provide plasma. The plasma samples were then stored in a freezer at −75±15° C. prior to LC-MS/MS analysis.

Concentrations of compound in the plasma samples were then analyzed using an LC-MS/MS method. WinNonlin (Phoenix™, version 6.1) or other similar software was used for PK calculations. The following PK parameters were calculated, whenever possible from the plasma concentration versus time data: $C_{max}$, $T_{max}$, $T_{1/2}$, $AUC_{inf}$ and $AUC_{last}$. The PK data were described using descriptive statistics such as mean with standard deviation.

The results for crystalline Form 8 are shown in Table 20 below and in FIG. 36.

TABLE 20

Summary of Crystalline Form 8 PK Parameters

| PK Parameters | Unit | Mouse 10 | Mouse 11 | Mouse 12 | Mean | SD | CV(%) |
|---|---|---|---|---|---|---|---|
| $T_{1/2}$ | h | NA | 11.4 | 2.08 | 6.8 | NA | NA |
| $T_{max}$ | h | 8.00 | 0.500 | 2.00 | 3.50 | 3.97 | 113 |
| $C_{max}$ | ng/mL | 8810 | 18200 | 17300 | 14770 | 5181 | 35.1 |
| $AUC_{last}$ | h * ng/mL | 144793 | 167910 | 233433 | 182045 | 45980 | 25.3 |

Example 20: Distribution of Crystalline Form 2 in Mouse Brain and Plasma

Female NOD SCID mice of an age between 6-8 weeks and a body weight range of 18-22 g were purchased from Beijing Anikeeper Biotech Co, Ltd. Animals were habituated to the environment for at least 7 days prior to study initiation. Mice were dosed with Crystalline Form 2 at either 100 mg/kg or 300 mg/kg dose levels via oral gavage for 28 days. After 24 hours following 27 doses of compound, three mice were euthanized via $CO_2$. After four hours following 28 doses of compound, three mice were euthanized via $CO_2$. At each time point the whole brain was collected. In addition, approximately 0.03 mL of blood was collected at each time point and centrifuged at 4000 G for 5 minutes at 4° C. to provide plasma. Samples were then stored in a freezer at −75±15° C. prior to LC-MS/MS analysis. Concentrations of compound in brain homogenates (ng/g) and plasma (ng/ml) were then analyzed using an LC-MS/MS method. The PK data were described using descriptive statistics such as mean with standard deviation.

As shown in Table 20 and FIG. 37, measurable drug level was observed in the brain tissue. There was no apparent accumulation of the drug in the brain after repeated dosing.

TABLE 20

Summary of brain penetration of crystalline Form 2 in NOD SCID mice

| | Crystalline Form 2 | |
|---|---|---|
| Parameters | 4 h (Day 28) | 24 h (Day 28) |
| 100 mg/kg | | |
| Brain Conc. (ng/g) | 1525 ± 559 | 19.5 |
| Plasma Conc. (ng/mL) | 5040 ± 694 | 178 ± 165 |
| B/P Ratio | 0.306 ± 00.125 | 0.091 ± 0.014 |
| 300 mg/kg | | |
| Brain Conc. (ng/g) | 6500 ± 1050 | 66.1 ± 81.7 |
| Plasma Conc. (ng/mL) | 15333 ± 2318 | 667 ± 852 |
| B/P Ratio | 0.424 ± 0.018 | 0.102 ± 0.007 |

Example 21. Distribution of Crystalline Form 2 in Rat Brain and Plasma

Male and female Sprague Dawley rats were purchased from Beijing Anikeeper Biotech Co, Ltd. Animals were habituated to the environment prior to study initiation. Rats were dosed with single dose of 100 mg/kg crystalline Form 2 via oral gavage. The rats were fasted overnight prior to dosing. Animals had access to food from 2 hours post dose and free access to water throughout the study. Approximately 0.2 mL of blood was sampled via jugular vein at each time point and centrifuged at 4000 G for 5 minutes at 4° C. to provide plasma. Samples were then stored in a freezer at −75±15° C. prior to LC-MS/MS analysis. Whole brain was collected after hemoperfusion and snap frozen on dry ice prior to storage at −75±15° C. Prior to LC-MS/MS analysis whole brains were weighed and homogenized with water by tissue weight (g) to water volume (ml) ratio 1:3 before analysis. Actual concentration is the measured value multiplied by the dilution factor. The PK data were described using descriptive statistics such as mean with standard deviation.

As shown in Table 21 and FIG. 38, measurable drug level was observed in the brain tissue. A similar elimination profile was also observed between plasma and brain tissue, suggesting a rapid equilibrium between systemic circulation and brain tissue.

TABLE 21

Summary of brain penetration of crystalline Form 2 in SD male and female rats

| Parameters | Crystalline Form 2 | |
| --- | --- | --- |
| | Plasma | Brain |
| Male | | |
| $C_{max}$ (ng/mL or ng/g) | 5297 | 3903 |
| $t_{max}$ (h) | 8.00 | 8.00 |
| $t_{1/2}$ (h) | 9.13 | 7.43 |
| $AUC_{0-\infty}$ (ng · h/mL or ng · h/g) | 101618 | 60596 |
| B/P Conc. Ratio at $t_{max}$ | 0.731 | |
| Female | | |
| $C_{max}$ (ng/mL or ng/g) | 9760 | 5613 |
| $t_{max}$ (h) | 8.00 | 8.00 |
| $t_{1/2}$ (h) | 16.9 | 12.8 |
| $AUC_{0-\infty}$ (ng · h/mL or ng · h/g) | 266414 | 120933 |
| B/P Conc. Ratio at $t_{max}$ | 0.580 | |

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

We claim:

1. A solid state form of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II):

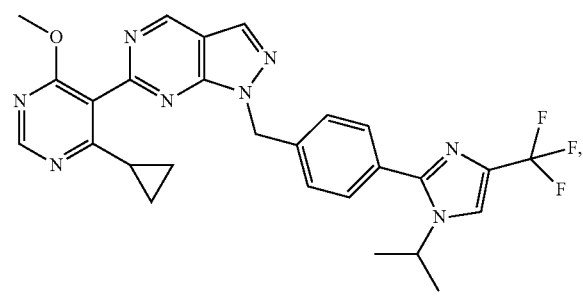

(II)

or a pharmaceutically acceptable salt thereof.

2. The solid state form of claim 1, wherein the solid state form is a pharmaceutically acceptable co-crystal formed between 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and a pharmaceutically acceptable acid.

3. The solid state form of claim 2, wherein the pharmaceutically acceptable acid is gentisic acid.

4. The solid state form of claim 3, wherein the gentisic acid co-crystal is crystalline Form 2 characterized by an XRPD pattern having peaks at 16.6±0.2, 18.7±0.2, and 22.5±0.2 degrees two theta.

5. The solid state form of claim 3, characterized by an endothermic peak at about 186.0° C., as determined by DSC.

6. The solid state form of claim 3, characterized by an about 3.17 wt % loss between room temperature and about 170° C., as determined by TGA.

7. The solid state form of claim 3, characterized by at least one of the following:
   a) an XRPD pattern as shown in FIG. 9;
   b) a DSC profile as shown in FIG. 10; or
   c) a TGA profile as shown in FIG. 10.

8. A mixture comprising the solid state form of claim 3 and a second solid state form of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II).

9. The solid state form of 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) of claim 2 selected from the group consisting of:
   a) crystalline Form A, wherein Form A is characterized by an XRPD pattern having peaks at 14.3±0.2, 21.5±0.2, and 21.8±0.2 degrees two theta;
   b) crystalline Form C, wherein Form C is characterized by an XRPD pattern having peaks at 14.2±0.2, 17.0±0.2, and 19.1±0.2 degrees two theta;
   c) crystalline Form D, wherein Form D is characterized by an XRPD pattern having peaks at 13.9±0.2, 15.2±0.2, and 19.3±0.2 degrees two theta;
   d) crystalline Form E, wherein Form E is characterized by an XRPD pattern having peaks at 10.6±0.2, 18.7±0.2, and 20.9±0.2 degrees two theta; and
   e) crystalline Form F, wherein Form F is characterized by an XRPD pattern having peaks at 10.7±0.2, 14.3±0.2, and 21.8±0.2 degrees two theta;
or combinations thereof.

10. The solid state form of claim 9, wherein the solid state form is crystalline Form A, and
   wherein the solid state form is characterized by at least one of the following:
      a) an XRPD pattern as shown in FIG. 1;
      b) an endothermic peak at about 165° C., as determined by DSC;
      c) a DSC profile as shown in FIG. 2;
      d) an about 0.93 wt % loss between room temperature and about 150° C., as determined by TGA; or
      e) a TGA profile as shown in FIG. 2.

11. The solid state form of claim 9, wherein the solid state form is crystalline Form C, and
   wherein the solid state form is characterized by an XRPD pattern as shown in FIG. 3.

12. The solid state form of claim 9, wherein the solid state form is crystalline Form D, and
   wherein the solid state form is characterized by an XRPD pattern as shown in FIG. 4.

13. The solid state form of claim 9, wherein the solid state form is crystalline Form E, and wherein the solid state form is characterized by at least one of the following:
a) an XRPD pattern as shown in FIG. 5;
b) an endothermic peak at about 107° C., as determined by DSC;
c) a DSC profile as shown in FIG. 6;
d) an about 13.5 wt % loss between room temperature and about 200° C., as determined by TGA; or
e) a TGA profile as shown in FIG. 6.

14. The solid state form of claim 9, wherein the solid state form is crystalline Form F, and
wherein the solid state form is characterized by one of the following:
a) an XRPD pattern as shown in FIG. 25;
b) an endothermic peak at about 157° C., as determined by DSC; or
c) a DSC profile as shown in FIG. 26.

15. The solid state form of claim 1, wherein the solid state form is a pharmaceutically acceptable salt formed between 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula (II) and a pharmaceutically acceptable acid.

16. The solid state form of claim 15, wherein the pharmaceutically acceptable salt is a hydrochloric acid salt; and wherein the hydrochloric acid salt is crystalline Form 1 characterized by an XRPD pattern having peaks at 12.5±0.2, 22.4±0.2, and 23.9±0.2 degrees two theta.

17. The solid state form of claim 2, wherein the pharmaceutically acceptable acid is benzoic acid, and
wherein the benzoic acid co-crystal is crystalline Form 8 characterized by an XRPD pattern having peaks at 12.1±0.2, 14.2±0.2, and 16.5±0.2 degrees two theta.

18. The solid state form of claim 2, wherein the pharmaceutically acceptable acid is salicylic acid, and
wherein the salicylic acid co-crystal is crystalline Form 9 characterized by an XRPD pattern having peaks at 11.0±0.2, 16.5±0.2, 17.3±0.2 and 25.3±0.2 degrees two theta.

19. A pharmaceutical composition comprising the solid state form of claim 1 and one or more pharmaceutically acceptable carriers or diluents.

20. A pharmaceutical composition comprising the solid state form of claim 3 and one or more pharmaceutically acceptable carriers or diluents.

21. A pharmaceutical composition comprising the solid state form of claim 4 and one or more pharmaceutically acceptable carriers or diluents.

22. The pharmaceutical composition of claim 19, which is an oral solid dosage form.

23. The pharmaceutical composition of claim 22, wherein the solid dosage form is selected from a tablet, a capsule, a pill, granules, a powder, a sachet, a chewable, and a film.

24. The pharmaceutical composition of claim 20, which is an oral solid dosage form.

25. The pharmaceutical composition of claim 24, wherein the solid dosage form is selected from a tablet, a capsule, a pill, granules, a powder, a sachet, a chewable, and a film.

26. The pharmaceutical composition of claim 21, which is an oral solid dosage form.

27. The pharmaceutical composition of claim 26, wherein the solid dosage form is selected from a tablet, a capsule, a pill, granules, a powder, a sachet, a chewable, and a film.

* * * * *

UNITED STATES PATENT AND TRADEMARK OFFICE
CERTIFICATE OF CORRECTION

PATENT NO. : 11,718,624 B2
APPLICATION NO. : 17/512802
DATED : August 8, 2023
INVENTOR(S) : Liu et al.

It is certified that error appears in the above-identified patent and that said Letters Patent is hereby corrected as shown below:

In the Specification

In Column 17, Line 55, delete "using)" and insert -- using --, therefor.

In Column 17, Line 56, delete "(RFD," and insert -- XRPD, --, therefor.

In Column 67, Line 22, delete "to)(RFD," and insert -- to XRPD, --, therefor.

In the Claims

In Column 90, Claim 9, Line 29, delete "2" and insert -- 1 --, therefor.

Signed and Sealed this
Twentieth Day of February, 2024

Katherine Kelly Vidal
*Director of the United States Patent and Trademark Office*